United States Patent
Ng et al.

(10) Patent No.: US 11,596,757 B2
(45) Date of Patent: *Mar. 7, 2023

(54) INTERCHANGEABLE MASK ASSEMBLY

(71) Applicant: ResMed Pty Ltd, Bella Vista (AU)

(72) Inventors: Eva Ng, Sydney (AU); Robert Edward Henry, Sydney (AU); Philip Rodney Kwok, Sydney (AU); Karthikeyan Selvarajan, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/355,540

(22) Filed: Jun. 23, 2021

(65) Prior Publication Data
US 2021/0316101 A1 Oct. 14, 2021

Related U.S. Application Data

(63) Continuation of application No. 16/216,115, filed on Dec. 11, 2018, now Pat. No. 11,052,211, which is a
(Continued)

(51) Int. Cl.
*A61M 16/00* (2006.01)
*A61M 16/06* (2006.01)
*A61M 16/08* (2006.01)

(52) U.S. Cl.
CPC ........ *A61M 16/0622* (2014.02); *A61M 16/06* (2013.01); *A61M 16/065* (2014.02);
(Continued)

(58) Field of Classification Search
CPC ........ A61M 16/00; A61M 16/06–0694; A61M 16/0816; A61M 2202/0085;
(Continued)

(56) References Cited

U.S. PATENT DOCUMENTS 428,592 A 5/1890 Chapman
443,191 A 12/1890 Illing
(Continued)

FOREIGN PATENT DOCUMENTS

AU 91/77110 11/1991
AU 94/64816 12/1994
(Continued)

OTHER PUBLICATIONS

Further Examination Report dated Aug. 28, 2017 issued in New Zealand Application No. 719679 (2 pages).
(Continued)

*Primary Examiner* — Victoria Murphy
*Assistant Examiner* — Tyler A Raubenstraw
(74) *Attorney, Agent, or Firm* — Nixon & Vanderhye P.C.

(57) ABSTRACT

A system of breathing arrangements for delivering breathable gas to a patient includes at least first and second cushion components, e.g., full-face, nasal, nasal prongs, nose tip, and/or a combination of any of the above, including a nasal or full-face cushion and nasal prongs/nozzles combination, etc., that are different from one another in at least one aspect, and a common frame assembly configured to support each of the first and second cushion components. Various embodiments are directed to a full-face or nasal mask used with a frame having lateral connector portions having a stiffening member. The mask assembly may include a nose height adjustment device for the height of the cushion, or a cushion adjustment member by which the position of the cushion may be adjusted relative to the frame. The mask assembly may include a chin strap assembly.

9 Claims, 22 Drawing Sheets

Related U.S. Application Data continuation of application No. 15/841,488, filed on Dec. 14, 2017, now Pat. No. 10,183,138, which is a continuation of application No. 14/289,158, filed on May 28, 2014, now Pat. No. 9,962,510, which is a continuation of application No. 12/083,779, filed as application No. PCT/AU2006/001570 on Oct. 24, 2006, now abandoned.

(60) Provisional application No. 60/729,746, filed on Oct. 25, 2005.

(52) U.S. Cl.
CPC .... *A61M 16/0605* (2014.02); *A61M 16/0611* (2014.02); *A61M 16/0633* (2014.02); *A61M 16/0638* (2014.02); *A61M 16/0683* (2013.01); *A61M 16/0616* (2014.02); *A61M 16/0644* (2014.02); *A61M 16/0666* (2013.01); *A61M 16/0672* (2014.02); *A61M 16/0694* (2014.02); *A61M 16/0816* (2013.01)

(58) Field of Classification Search
CPC ...... A61M 2205/42; A61M 2202/0225; A61M 16/0622; A61M 16/0605; A61M 16/0611; A61M 16/0633; A61M 16/0638; A61M 16/065; A61M 16/0683; A61M 16/0616; A61M 16/0644; A61M 16/0672; A61M 16/0694; A61M 16/0666; A62B 18/02; A62B 18/025
See application file for complete search history.

(56) References Cited

U.S. PATENT DOCUMENTS

| | | |
|---|---|---|
| 781,516 A | 1/1905 | Guthrie |
| 812,706 A | 2/1906 | Warbasse |
| 1,081,745 A * | 12/1913 | Johnston ............... A61M 16/18 128/203.25 |
| 1,125,542 A | 1/1915 | Humphries |
| 1,176,886 A | 3/1916 | Ermold |
| 1,192,186 A | 7/1916 | Greene |
| 1,206,045 A | 11/1916 | Smith |
| 1,229,050 A | 6/1917 | Donald |
| 1,282,527 A | 10/1918 | Bidonde |
| 1,362,766 A | 12/1920 | McGargill |
| 1,445,010 A | 2/1923 | Feinberg |
| 1,610,793 A | 12/1926 | Kaufman |
| 1,632,449 A | 6/1927 | McKesson |
| 1,653,572 A | 12/1927 | Jackson |
| 1,710,160 A | 4/1929 | Gibbs |
| 1,873,160 A | 8/1932 | Sturtevant |
| 1,926,027 A | 9/1933 | Biggs |
| 2,011,733 A | 8/1935 | Shindel |
| 2,104,016 A | 1/1938 | Biggs |
| 2,123,353 A | 7/1938 | Catt |
| 2,127,136 A | 8/1938 | Pobirs |
| 2,130,555 A | 9/1938 | Malcom |
| 2,133,699 A | 10/1938 | Heidbrink |
| 2,166,164 A | 7/1939 | Lehmberg |
| 2,245,658 A | 6/1941 | Erickson |
| 2,245,969 A | 6/1941 | Francisco et al. |
| 2,248,477 A | 7/1941 | Lombard |
| 2,254,854 A | 9/1941 | O'Connell |
| 2,317,608 A | 4/1943 | Heidbrink |
| 2,353,643 A | 7/1944 | Bulbulian |
| 2,371,965 A | 3/1945 | Lehmberg |
| 2,376,871 A | 5/1945 | Fink |
| 2,382,364 A | 8/1945 | Yant |
| 2,415,846 A | 2/1947 | Randall |
| 2,428,451 A | 10/1947 | Emerson |
| 2,433,565 A | 12/1947 | Korman |
| 2,438,058 A | 3/1948 | Kincheloe |
| 2,473,518 A | 6/1949 | Garrard et al. |
| D156,060 S | 11/1949 | Wade |
| D161,337 S | 12/1950 | Hill |
| 2,540,567 A | 2/1951 | Bennett |
| 2,578,621 A | 12/1951 | Yant |
| 2,590,006 A | 3/1952 | Gordon |
| 2,625,155 A | 1/1953 | Engelder |
| 2,641,253 A | 6/1953 | Engelder |
| 2,693,178 A | 11/1954 | Gilroy |
| 2,706,983 A | 4/1955 | Matheson et al. |
| 2,749,910 A | 6/1956 | Faulconer, Jr. |
| RE24,193 E | 8/1956 | Emerson |
| 2,820,651 A | 1/1958 | Phillips |
| 2,837,090 A | 6/1958 | Bloom et al. |
| 2,868,196 A | 1/1959 | Stampe |
| 2,875,757 A | 3/1959 | Galleher, Jr. |
| 2,875,759 A | 3/1959 | Galleher, Jr. |
| 2,881,444 A | 4/1959 | Fresh et al. |
| 2,882,895 A | 4/1959 | Galeazzi |
| 2,902,033 A | 9/1959 | Galleher, Jr. |
| 2,917,045 A | 12/1959 | Schildknecht et al. |
| 2,931,356 A | 4/1960 | Schwarz |
| D188,084 S | 5/1960 | Garelick |
| 2,939,458 A | 6/1960 | Lundquist |
| 3,013,556 A | 12/1961 | Galleher, Jr. |
| 3,042,035 A | 7/1962 | Coanda |
| 3,117,574 A | 1/1964 | Replogle |
| 3,182,659 A | 5/1965 | Blount |
| 3,189,027 A | 6/1965 | Bartlett, Jr. |
| 3,193,624 A | 7/1965 | Webb et al. |
| 3,238,943 A | 3/1966 | Holley |
| 3,288,138 A | 11/1966 | Sachs |
| 3,315,672 A | 4/1967 | Cunningham et al. |
| 3,315,674 A | 4/1967 | Bloom et al. |
| 3,330,273 A | 7/1967 | Bennett |
| 3,330,274 A | 7/1967 | Bennett |
| 3,362,420 A | 1/1968 | Blackburn et al. |
| 3,363,833 A | 1/1968 | Laerdal |
| 3,545,436 A | 12/1970 | Holloway |
| 3,556,122 A | 1/1971 | Laerdal |
| 3,580,051 A | 5/1971 | Blevins |
| 3,670,726 A | 3/1972 | Mahon et al. |
| 3,682,171 A | 8/1972 | Dali et al. |
| 3,700,000 A | 10/1972 | Hesse et al. |
| 3,720,235 A | 3/1973 | Schrock |
| 3,725,953 A | 4/1973 | Johnson et al. |
| 3,739,774 A | 6/1973 | Gregory |
| 3,750,333 A | 8/1973 | Vance |
| 3,752,157 A | 8/1973 | Malmin |
| 3,754,552 A | 8/1973 | King |
| 3,796,216 A | 3/1974 | Schwarz |
| 3,799,164 A | 3/1974 | Rollins |
| D231,803 S | 6/1974 | Huddy |
| 3,830,230 A | 8/1974 | Chester |
| 3,861,385 A | 1/1975 | Carden |
| 3,902,486 A | 9/1975 | Guichard |
| 3,905,361 A | 9/1975 | Hewson et al. |
| 3,910,261 A | 10/1975 | Ragsdale et al. |
| 3,938,614 A | 2/1976 | Ahs |
| 3,972,321 A | 8/1976 | Proctor |
| 3,978,854 A | 9/1976 | Mills, Jr. |
| 4,006,744 A | 2/1977 | Steer |
| 4,062,357 A | 12/1977 | Laerdal |
| 4,069,516 A | 1/1978 | Watkins, Jr. |
| 4,077,404 A | 3/1978 | Elam |
| D248,497 S | 7/1978 | Slosek |
| D250,131 S | 10/1978 | Lewis et al. |
| 4,120,302 A | 10/1978 | Ziegler |
| 4,142,527 A | 3/1979 | Garcia |
| 4,153,051 A | 5/1979 | Shippert |
| 4,156,426 A | 5/1979 | Gold |
| 4,167,185 A | 9/1979 | Lewis |
| 4,201,205 A | 5/1980 | Bartholomew |
| 4,226,234 A | 10/1980 | Gunderson |
| 4,231,363 A | 11/1980 | Grimes |
| 4,233,972 A | 11/1980 | Hauff et al. |
| 4,239,038 A | 12/1980 | Holmes |
| 4,245,632 A | 1/1981 | Houston |
| 4,248,218 A | 2/1981 | Fischer |

(56) References Cited

U.S. PATENT DOCUMENTS

| | | |
|---|---|---|
| 4,263,908 A | 4/1981 | Mizerak |
| 4,264,743 A | 4/1981 | Maruyama et al. |
| 4,265,239 A | 5/1981 | Fischer, Jr. et al. |
| 4,266,540 A | 5/1981 | Panzik et al. |
| 4,267,845 A | 5/1981 | Robertson, Jr. et al. |
| 4,273,124 A | 6/1981 | Zimmerman |
| D262,322 S | 12/1981 | Mizerak |
| 4,304,229 A | 12/1981 | Curtin |
| 4,312,359 A | 1/1982 | Olson |
| 4,328,797 A | 5/1982 | Rollins et al. |
| 4,337,767 A | 7/1982 | Yahata |
| 4,347,205 A | 8/1982 | Stewart |
| 4,354,488 A | 10/1982 | Bartos |
| 4,367,735 A | 1/1983 | Dali |
| 4,367,816 A | 1/1983 | Wilkes |
| 4,369,284 A | 1/1983 | Chen |
| 4,402,316 A | 9/1983 | Gadberry |
| 4,406,283 A | 9/1983 | Bir |
| 4,412,537 A | 11/1983 | Tiger |
| 4,414,973 A | 11/1983 | Matheson et al. |
| 4,417,575 A | 11/1983 | Hilton et al. |
| 4,422,456 A | 12/1983 | Teip |
| 4,446,576 A | 5/1984 | Hisataka |
| 4,449,526 A | 5/1984 | Elam |
| 4,454,880 A | 6/1984 | Muto et al. |
| 4,454,881 A | 6/1984 | Huber et al. |
| 4,455,675 A | 6/1984 | Bose et al. |
| 4,458,679 A | 7/1984 | Ward |
| 4,467,799 A | 8/1984 | Steinberg |
| 4,493,614 A | 1/1985 | Chu et al. |
| 4,522,639 A | 6/1985 | Ansite et al. |
| 4,548,200 A | 10/1985 | Wapner |
| 4,549,542 A | 11/1985 | Chein |
| 4,558,710 A | 12/1985 | Eichler |
| 4,572,323 A | 2/1986 | Randall |
| 4,587,967 A | 5/1986 | Chu et al. |
| 4,593,688 A | 6/1986 | Payton |
| 4,601,465 A | 7/1986 | Roy |
| D285,496 S | 9/1986 | Berman |
| 4,616,647 A | 10/1986 | McCreadie |
| 4,617,637 A | 11/1986 | Chu et al. |
| 4,622,964 A | 11/1986 | Flynn |
| 4,630,604 A | 12/1986 | Montesi |
| 4,641,645 A | 2/1987 | Tayebi |
| 4,641,647 A | 2/1987 | Behan |
| D289,238 S | 4/1987 | Arthur, Jr. |
| 4,655,213 A | 4/1987 | Rapoport et al. |
| 4,660,555 A | 4/1987 | Payton |
| 4,665,570 A | 5/1987 | Davis |
| 4,671,267 A | 6/1987 | Stout |
| 4,671,271 A | 6/1987 | Bishop et al. |
| 4,674,134 A | 6/1987 | Lundin |
| 4,676,241 A | 6/1987 | Webb et al. |
| 4,677,975 A | 7/1987 | Edgar et al. |
| 4,677,977 A | 7/1987 | Wilcox |
| 4,686,977 A | 8/1987 | Cosma |
| 4,699,139 A | 10/1987 | Marshall et al. |
| 4,706,664 A | 11/1987 | Snook et al. |
| 4,707,863 A | 11/1987 | McNeal |
| 4,711,636 A | 12/1987 | Bierman |
| 4,713,844 A | 12/1987 | Westgate |
| H397 H | 1/1988 | Stark |
| D293,613 S | 1/1988 | Wingler |
| 4,739,755 A | 4/1988 | White et al. |
| 4,753,233 A | 6/1988 | Grimes |
| 4,767,411 A | 8/1988 | Edmunds |
| 4,770,169 A | 9/1988 | Schmoegner et al. |
| 4,772,760 A | 9/1988 | Graham |
| 4,774,941 A | 10/1988 | Cook |
| 4,774,946 A | 11/1988 | Ackerman et al. |
| 4,782,832 A | 11/1988 | Trimble et al. |
| 4,790,829 A | 12/1988 | Bowden et al. |
| 4,799,477 A | 1/1989 | Lewis |
| 4,802,857 A | 2/1989 | Laughlin |
| 4,803,981 A | 2/1989 | Vickery |
| 4,807,617 A | 2/1989 | Nesti |
| 4,809,692 A | 3/1989 | Nowacki et al. |
| 4,811,730 A | 3/1989 | Milano |
| 4,819,629 A | 4/1989 | Jonson |
| 4,821,713 A | 4/1989 | Bauman |
| 4,830,138 A | 5/1989 | Palmaer et al. |
| 4,832,017 A | 5/1989 | Schnoor |
| 4,838,878 A | 6/1989 | Kalt et al. |
| 4,841,953 A | 6/1989 | Dodrill |
| 4,848,334 A | 7/1989 | Bellm |
| 4,848,366 A | 7/1989 | Aita et al. |
| 4,850,346 A | 7/1989 | Michel et al. |
| 4,856,118 A | 8/1989 | Sapiejewski |
| D304,384 S | 10/1989 | Derobert |
| 4,899,740 A | 2/1990 | Napolitano |
| 4,905,683 A | 3/1990 | Cronjaeger |
| 4,907,584 A | 3/1990 | McGinnis |
| 4,910,806 A | 3/1990 | Baker et al. |
| 4,914,957 A | 4/1990 | Dougherty |
| 4,915,105 A | 4/1990 | Lee |
| 4,915,106 A | 4/1990 | Aulgur et al. |
| 4,919,128 A | 4/1990 | Kopala et al. |
| 4,919,654 A | 4/1990 | Kalt |
| 4,938,210 A | 7/1990 | Shene |
| 4,938,212 A | 7/1990 | Snook et al. |
| 4,941,476 A | 7/1990 | Fisher |
| 4,944,310 A | 7/1990 | Sullivan |
| 4,945,907 A | 8/1990 | Tayebi |
| 4,947,860 A | 8/1990 | Fisher |
| D310,431 S | 9/1990 | Bellm |
| 4,960,121 A | 10/1990 | Nelson et al. |
| 4,966,590 A | 10/1990 | Kalt |
| 4,969,880 A | 11/1990 | Zamierowski |
| 4,971,051 A | 11/1990 | Toffolon |
| D313,277 S | 12/1990 | Haining |
| 4,976,698 A | 12/1990 | Stokley |
| 4,986,269 A | 1/1991 | Hakkinen |
| 4,989,271 A | 2/1991 | Sapiejewski et al. |
| 4,989,596 A | 2/1991 | Macris et al. |
| 4,989,599 A | 2/1991 | Carter |
| 4,996,983 A | 3/1991 | Amrhein |
| 5,000,173 A | 3/1991 | Zalkin et al. |
| 5,003,631 A | 4/1991 | Richardson |
| 5,003,633 A | 4/1991 | Itoh |
| 5,005,568 A | 4/1991 | Loescher et al. |
| 5,005,571 A | 4/1991 | Dietz |
| 5,018,519 A | 5/1991 | Brown |
| 5,020,163 A | 6/1991 | Aileo et al. |
| 5,022,900 A | 6/1991 | Bar-Yona et al. |
| 5,023,955 A | 6/1991 | Murphy, II et al. |
| 5,025,805 A | 6/1991 | Nutter |
| 5,027,809 A | 7/1991 | Robinson |
| 5,038,772 A | 8/1991 | Kolbe et al. |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,046,491 A | 9/1991 | Derrick |
| 5,062,421 A | 11/1991 | Burns et al. |
| 5,063,922 A | 11/1991 | Hakkinen |
| 5,069,205 A | 12/1991 | Urso |
| 5,074,297 A | 12/1991 | Venegas |
| 5,080,092 A | 1/1992 | Tenna |
| D323,908 S | 2/1992 | Hollister et al. |
| 5,093,940 A | 3/1992 | Nishiyama |
| 5,109,839 A | 5/1992 | Blasdell et al. |
| 5,109,840 A | 5/1992 | Daleiden |
| 5,113,857 A | 5/1992 | Dickerman et al. |
| 5,117,818 A | 6/1992 | Palfy |
| 5,121,745 A | 6/1992 | Israel |
| 5,121,746 A | 6/1992 | Sikora |
| 5,123,677 A | 6/1992 | Kreczko et al. |
| 5,127,397 A | 7/1992 | Kohnke |
| 5,133,347 A | 7/1992 | Huennebeck |
| 5,137,017 A | 8/1992 | Salter |
| 5,138,722 A | 8/1992 | Urella et al. |
| 5,140,980 A | 8/1992 | Haughey et al. |
| 5,140,982 A | 8/1992 | Bauman |
| 5,146,914 A | 9/1992 | Sturrock |

(56) References Cited

U.S. PATENT DOCUMENTS

| | | |
|---|---|---|
| 5,159,938 A | 11/1992 | Laughlin |
| 5,178,138 A | 1/1993 | Walstrom et al. |
| 5,181,506 A | 1/1993 | Tardiff, Jr. et al. |
| D333,015 S | 2/1993 | Farmer et al. |
| 5,188,101 A | 2/1993 | Tumolo |
| D334,633 S | 4/1993 | Rudolph |
| 5,199,424 A | 4/1993 | Sullivan et al. |
| D335,322 S | 5/1993 | Jones |
| 5,207,665 A | 5/1993 | Davis et al. |
| 5,220,699 A | 6/1993 | Farris |
| 5,222,478 A | 6/1993 | Scarberry et al. |
| 5,231,983 A | 8/1993 | Matson et al. |
| 5,233,978 A | 8/1993 | Callaway |
| 5,243,709 A | 9/1993 | Sheehan et al. |
| 5,243,971 A | 9/1993 | Sullivan et al. |
| 5,245,995 A | 9/1993 | Sullivan et al. |
| 5,261,893 A | 11/1993 | Zamierowski |
| 5,263,939 A | 11/1993 | Wortrich |
| 5,265,592 A | 11/1993 | Beaussant |
| 5,265,595 A | 11/1993 | Rudolph |
| 5,267,557 A | 12/1993 | Her-Mou |
| 5,269,296 A | 12/1993 | Landis |
| 5,271,391 A | 12/1993 | Graves |
| 5,279,289 A | 1/1994 | Kirk |
| 5,280,784 A | 1/1994 | Kohler |
| 5,291,880 A | 3/1994 | Almovist et al. |
| 5,299,448 A | 4/1994 | Maryyanek |
| 5,299,579 A | 4/1994 | Gedeon et al. |
| 5,299,599 A | 4/1994 | Farmer et al. |
| 5,301,689 A | 4/1994 | Wennerholm |
| 5,304,146 A | 4/1994 | Johnson et al. |
| 5,311,862 A | 5/1994 | Blasdell et al. |
| 5,322,057 A | 6/1994 | Raabe et al. |
| 5,322,059 A | 6/1994 | Walther |
| 5,331,691 A | 7/1994 | Runckel |
| D349,586 S | 8/1994 | Handke |
| 5,334,646 A | 8/1994 | Chen |
| 5,335,656 A | 8/1994 | Bowe et al. |
| 5,343,878 A | 9/1994 | Scarberry et al. |
| 5,349,949 A | 9/1994 | Schegerin |
| 5,353,789 A | 10/1994 | Schlobohm |
| 5,355,878 A | 10/1994 | Griffiths et al. |
| 5,355,893 A | 10/1994 | Mick et al. |
| 5,357,945 A | 10/1994 | Messina |
| 5,357,951 A | 10/1994 | Ratner |
| 5,364,367 A | 11/1994 | Banks et al. |
| 5,372,130 A | 12/1994 | Stern et al. |
| 5,372,388 A | 12/1994 | Gargiulo |
| 5,372,389 A | 12/1994 | Tam et al. |
| 5,372,390 A | 12/1994 | Conway et al. |
| 5,372,391 A | 12/1994 | Bast et al. |
| 5,375,593 A | 12/1994 | Press |
| 5,385,141 A | 1/1995 | Granatiero |
| 5,388,571 A | 2/1995 | Roberts et al. |
| 5,390,373 A | 2/1995 | Flory |
| 5,391,248 A | 2/1995 | Brain |
| 5,394,568 A | 3/1995 | Brostrom et al. |
| 5,396,885 A | 3/1995 | Nelson |
| 5,398,676 A | 3/1995 | Press et al. |
| 5,400,776 A | 3/1995 | Bartholomew |
| 5,400,781 A | 3/1995 | Davenport |
| 5,404,871 A | 4/1995 | Goodman et al. |
| 5,411,021 A | 5/1995 | Gdulla et al. |
| 5,419,317 A | 5/1995 | Blasdell et al. |
| 5,419,318 A | 5/1995 | Tayebi |
| 5,425,359 A | 6/1995 | Liou |
| 5,429,126 A | 7/1995 | Bracken |
| 5,429,683 A | 7/1995 | Le Mitouard |
| 5,431,158 A | 7/1995 | Tirotta |
| 5,437,267 A | 8/1995 | Weinstein et al. |
| 5,437,273 A | 8/1995 | Bates |
| 5,438,981 A | 8/1995 | Starr et al. |
| 5,441,046 A | 8/1995 | Starr et al. |
| D362,061 S | 9/1995 | McGinnis |
| 5,462,528 A | 10/1995 | Roewer |
| 5,477,852 A | 12/1995 | Landis et al. |
| 5,479,920 A | 1/1996 | Piper et al. |
| 5,481,763 A | 1/1996 | Brostrom et al. |
| 5,485,837 A | 1/1996 | Soles Bee et al. |
| 5,488,948 A | 2/1996 | Dubruille et al. |
| 5,492,116 A | 2/1996 | Scarberry et al. |
| 5,501,214 A | 3/1996 | Sabo |
| 5,503,147 A | 4/1996 | Bertheau |
| 5,509,404 A | 4/1996 | Lloyd et al. |
| 5,509,409 A | 4/1996 | Weatherholt |
| 5,511,541 A | 4/1996 | Dearstine |
| 5,513,634 A | 5/1996 | Jackson |
| 5,513,635 A | 5/1996 | Bedi |
| 5,517,986 A | 5/1996 | Starr et al. |
| 5,522,382 A | 6/1996 | Sullivan et al. |
| 5,526,806 A | 6/1996 | Sansoni |
| 5,533,506 A | 7/1996 | Wood |
| 5,538,000 A | 7/1996 | Rudolph |
| 5,538,001 A | 7/1996 | Bridges |
| 5,540,223 A | 7/1996 | Starr et al. |
| 5,542,128 A | 8/1996 | Lomas |
| 5,546,936 A | 8/1996 | Virag et al. |
| 5,558,090 A | 9/1996 | James |
| RE35,339 E | 10/1996 | Rapoport |
| 5,560,354 A | 10/1996 | Berthon-Jones et al. |
| 5,568,946 A | 10/1996 | Jackowski |
| 5,570,682 A | 11/1996 | Johnson |
| 5,570,684 A | 11/1996 | Behr |
| 5,570,689 A | 11/1996 | Starr et al. |
| D377,089 S | 12/1996 | Starr et al. |
| 5,592,938 A | 1/1997 | Scarberry et al. |
| 5,608,647 A | 3/1997 | Rubsamen et al. |
| 5,617,849 A | 4/1997 | Springett et al. |
| 5,623,923 A | 4/1997 | Bertheau et al. |
| 5,642,726 A | 7/1997 | Owens et al. |
| 5,642,730 A | 7/1997 | Baran |
| 5,645,054 A | 7/1997 | Cotner et al. |
| 5,647,355 A | 7/1997 | Starr et al. |
| 5,647,356 A | 7/1997 | Barnett et al. |
| 5,647,357 A | 7/1997 | Barnett et al. |
| 5,649,532 A | 7/1997 | Griffiths |
| 5,649,533 A | 7/1997 | Oren |
| 5,653,228 A | 8/1997 | Byrd |
| 5,655,520 A | 8/1997 | Howe et al. |
| 5,655,527 A | 8/1997 | Scarberry et al. |
| 5,657,493 A | 8/1997 | Ferrero et al. |
| 5,657,752 A | 8/1997 | Landis et al. |
| 5,660,171 A | 8/1997 | Kimm et al. |
| 5,660,174 A | 8/1997 | Jacobelli |
| 5,662,101 A | 9/1997 | Ogden et al. |
| 5,666,946 A | 9/1997 | Langenback |
| 5,676,133 A | 10/1997 | Hickle et al. |
| D385,960 S | 11/1997 | Rudolph |
| 5,682,881 A | 11/1997 | Winthrop et al. |
| 5,685,296 A | 11/1997 | Zdrojkowski et al. |
| 5,687,715 A | 11/1997 | Landis et al. |
| D389,238 S | 1/1998 | Kirk, III et al. |
| 5,704,345 A | 1/1998 | Berthon-Jones |
| 5,707,342 A | 1/1998 | Tanaka |
| 5,709,204 A | 1/1998 | Lester |
| 5,715,814 A | 2/1998 | Ebers |
| 5,724,964 A | 3/1998 | Brunson et al. |
| 5,724,965 A | 3/1998 | Handke et al. |
| 5,735,272 A | 4/1998 | Dillon et al. |
| 5,740,795 A | 4/1998 | Brydon |
| 5,740,799 A | 4/1998 | Nielson |
| 5,746,201 A | 5/1998 | Kidd |
| 5,752,509 A | 5/1998 | Lachmann et al. |
| 5,752,511 A | 5/1998 | Simmons et al. |
| 5,778,872 A | 7/1998 | Fukunaga et al. |
| 5,782,774 A | 7/1998 | Shmulewitz |
| 5,794,615 A | 8/1998 | Estes |
| 5,794,619 A | 8/1998 | Edeiman et al. |
| D398,987 S | 9/1998 | Cotner et al. |
| 5,807,341 A | 9/1998 | Heim |
| 5,813,423 A | 9/1998 | Kirchgeorg |
| 5,832,918 A | 11/1998 | Pantino |
| D402,755 S | 12/1998 | Kwok |
| 5,842,469 A | 12/1998 | Rapp et al. |

(56) References Cited

U.S. PATENT DOCUMENTS

| | | |
|---|---|---|
| RE36,165 E | 3/1999 | Behr |
| 5,884,624 A | 3/1999 | Barnett et al. |
| 5,887,587 A | 3/1999 | Groenke |
| 5,896,857 A | 4/1999 | Hely et al. |
| 5,906,203 A | 5/1999 | Klockseth et al. |
| 5,918,598 A | 7/1999 | Belfer et al. |
| 5,921,239 A | 7/1999 | McCall et al. |
| D412,745 S | 8/1999 | Scheu |
| 5,935,136 A | 8/1999 | Hulse et al. |
| 5,937,445 A | 8/1999 | Ravo et al. |
| 5,937,851 A | 8/1999 | Serowski et al. |
| 5,943,473 A | 8/1999 | Levine |
| 5,954,049 A | 9/1999 | Foley et al. |
| 5,964,485 A | 10/1999 | Hame et al. |
| 5,966,745 A | 10/1999 | Schwartz et al. |
| 5,970,975 A | 10/1999 | Estes et al. |
| 5,975,079 A | 11/1999 | Hellings et al. |
| 6,003,511 A | 12/1999 | Fukunaga et al. |
| 6,006,748 A | 12/1999 | Hollis |
| D419,658 S | 1/2000 | Matchett et al. |
| 6,016,804 A | 1/2000 | Gleason et al. |
| D421,298 S | 2/2000 | Kenyon et al. |
| 6,019,101 A | 2/2000 | Cotner et al. |
| 6,026,811 A | 2/2000 | Settle |
| 6,029,660 A | 2/2000 | Calluaud et al. |
| 6,029,665 A | 2/2000 | Berthon-Jones |
| 6,039,044 A | 3/2000 | Sullivan |
| D423,096 S | 4/2000 | Kwok |
| 6,044,844 A | 4/2000 | Kwok et al. |
| 6,062,221 A | 5/2000 | Brostrom et al. |
| 6,082,360 A | 7/2000 | Rudolph et al. |
| 6,086,118 A | 7/2000 | McNaughton et al. |
| 6,091,973 A | 7/2000 | Colla et al. |
| D428,987 S | 8/2000 | Kwok |
| 6,095,996 A | 8/2000 | Steer et al. |
| 6,098,205 A | 8/2000 | Schwartz et al. |
| 6,102,040 A | 8/2000 | Tayebi et al. |
| 6,109,263 A | 8/2000 | Feuchtgruber |
| 6,112,746 A | 9/2000 | Kwok et al. |
| 6,119,693 A | 9/2000 | Kwok et al. |
| 6,119,694 A | 9/2000 | Correa et al. |
| 6,123,071 A | 9/2000 | Berthon-Jones et al. |
| 6,123,082 A | 9/2000 | Berthon-Jones |
| 6,135,432 A | 10/2000 | Hebblewhite et al. |
| 6,139,787 A | 10/2000 | Harrison |
| 6,152,137 A | 11/2000 | Schwartz et al. |
| 6,155,253 A | 12/2000 | Gamberini |
| 6,192,886 B1 | 2/2001 | Rudolph |
| 6,193,914 B1 | 2/2001 | Harrison |
| D439,326 S | 3/2001 | Hecker et al. |
| 6,196,223 B1 | 3/2001 | Belfer et al. |
| 6,211,263 B1 | 4/2001 | Cinelli et al. |
| 6,213,125 B1 | 4/2001 | Reese et al. |
| 6,231,548 B1 | 5/2001 | Bassett |
| D443,355 S | 6/2001 | Gunaratnam et al. |
| 6,241,930 B1 | 6/2001 | Harrison |
| 6,257,237 B1 | 7/2001 | Suzuki |
| 6,257,626 B1 | 7/2001 | Campau |
| 6,258,066 B1 | 7/2001 | Urich |
| 6,272,933 B1 | 8/2001 | Gradon et al. |
| 6,279,573 B1 | 8/2001 | Johnson et al. |
| 6,295,366 B1 | 9/2001 | Baller et al. |
| 6,328,031 B1 | 12/2001 | Tischer et al. |
| 6,328,038 B1 | 12/2001 | Kessler et al. |
| 6,340,024 B1 | 1/2002 | Brookman et al. |
| 6,341,606 B1 | 1/2002 | Bordewick et al. |
| 6,345,618 B1 | 2/2002 | Hayek |
| 6,347,631 B1 | 2/2002 | Hansen et al. |
| 6,357,440 B1 | 3/2002 | Hansen et al. |
| 6,357,441 B1 | 3/2002 | Kwok et al. |
| 6,358,279 B1 | 3/2002 | Tahi et al. |
| 6,371,110 B1 | 4/2002 | Peterson et al. |
| 6,374,826 B1 | 4/2002 | Gunaratnam et al. |
| 6,388,640 B1 | 5/2002 | Chigira et al. |
| 6,397,847 B1 | 6/2002 | Scarberry et al. |
| 6,398,197 B1 | 6/2002 | Dickinson et al. |
| 6,412,487 B1 | 7/2002 | Gunaratnam et al. |
| 6,412,488 B1 | 7/2002 | Barnett et al. |
| 6,412,593 B1 | 7/2002 | Jones |
| 6,418,928 B1 | 7/2002 | Bordewick et al. |
| 6,419,660 B1 | 7/2002 | Russo |
| 6,422,238 B1 | 7/2002 | Lithgow |
| 6,423,036 B1 | 7/2002 | Van Huzen |
| 6,425,395 B1 | 7/2002 | Brewer et al. |
| 6,427,694 B1 | 8/2002 | Hecker et al. |
| 6,431,172 B1 | 8/2002 | Bordewick |
| 6,434,796 B1 | 8/2002 | Speirs |
| 6,439,230 B1 | 8/2002 | Gunaratnam et al. |
| 6,439,234 B1 | 8/2002 | Curti et al. |
| 6,448,303 B1 | 9/2002 | Paul |
| 6,463,931 B1 | 10/2002 | Kwok et al. |
| 6,467,482 B1 | 10/2002 | Boussignac |
| 6,467,483 B1 | 10/2002 | Kopacko et al. |
| 6,470,887 B1 | 10/2002 | Martinez |
| 6,478,026 B1 | 11/2002 | Wood |
| 6,482,178 B1 | 11/2002 | Andrews et al. |
| 6,491,034 B1 | 12/2002 | Gunaratnam et al. |
| D468,823 S | 1/2003 | Smart |
| 6,513,526 B2 | 2/2003 | Kwok et al. |
| 6,520,182 B1 | 2/2003 | Gunaratnam |
| 6,530,373 B1 | 3/2003 | Patron et al. |
| 6,532,961 B1 | 3/2003 | Kwok et al. |
| 6,536,435 B1 | 3/2003 | Fecteau et al. |
| 6,557,556 B2 | 5/2003 | Kwok et al. |
| 6,561,188 B1 | 5/2003 | Ellis |
| 6,561,190 B1 | 5/2003 | Kwok |
| 6,561,191 B1 | 5/2003 | Kwok |
| 6,561,192 B2 | 5/2003 | Palmer |
| 6,561,193 B1 | 5/2003 | Noble |
| 6,571,798 B1 | 6/2003 | Thornton |
| 6,579,267 B2 | 6/2003 | Lynch et al. |
| 6,581,594 B1 * | 6/2003 | Drew ............... A61M 16/0644 128/207.12 |
| 6,581,601 B2 | 6/2003 | Ziaee |
| 6,581,602 B2 | 7/2003 | Kwok et al. |
| 6,584,975 B1 | 7/2003 | Taylor |
| 6,595,214 B1 | 7/2003 | Hecker et al. |
| 6,595,215 B2 | 7/2003 | Wood |
| 6,607,516 B2 | 8/2003 | Cinelli et al. |
| 6,615,830 B1 | 9/2003 | Serowski et al. |
| 6,615,832 B1 | 9/2003 | Chen |
| 6,626,177 B1 | 9/2003 | Ziaee |
| 6,627,289 B1 | 9/2003 | Dilnik et al. |
| 6,631,718 B1 | 10/2003 | Lovell |
| 6,634,358 B2 | 10/2003 | Kwok et al. |
| 6,637,434 B2 | 10/2003 | Noble |
| 6,644,315 B2 | 11/2003 | Ziaee |
| 6,651,663 B2 | 11/2003 | Barnett et al. |
| D484,237 S | 12/2003 | Lang et al. |
| 6,655,385 B1 | 12/2003 | Curti et al. |
| 6,663,600 B2 | 12/2003 | Bierman et al. |
| 6,669,712 B1 | 12/2003 | Cardoso |
| D485,905 S | 1/2004 | Moore et al. |
| 6,679,257 B1 | 1/2004 | Robertson et al. |
| 6,679,261 B2 | 1/2004 | Lithgow |
| 6,679,265 B2 | 1/2004 | Strickland et al. |
| 6,691,707 B1 | 2/2004 | Gunaratnam et al. |
| 6,691,708 B2 | 2/2004 | Kwok et al. |
| 6,701,535 B2 | 3/2004 | Dobbie et al. |
| 6,701,926 B2 | 3/2004 | Olsen et al. |
| 6,701,927 B2 | 3/2004 | Kwok et al. |
| 6,710,099 B2 | 3/2004 | Cinelli et al. |
| 6,712,072 B1 | 3/2004 | Lang |
| 6,729,333 B2 | 5/2004 | Barnett et al. |
| D492,992 S | 7/2004 | Guney et al. |
| D493,521 S | 7/2004 | Guney |
| 6,766,800 B2 | 7/2004 | Chu et al. |
| 6,766,817 B2 | 7/2004 | da Silva |
| 6,772,760 B2 | 8/2004 | Frater et al. |
| 6,776,162 B2 | 8/2004 | Wood |
| 6,776,163 B2 | 8/2004 | Dougill et al. |
| 6,789,543 B2 | 9/2004 | Cannon |
| 6,796,308 B2 | 9/2004 | Gunaratnam et al. |

(56) References Cited

U.S. PATENT DOCUMENTS

| | | |
|---|---|---|
| 6,805,117 B1 * | 10/2004 | Ho .................... A61M 16/0683 128/201.22 |
| 6,807,967 B2 | 10/2004 | Wood |
| 6,817,362 B2 | 11/2004 | Gelinas et al. |
| 6,820,617 B2 | 11/2004 | Robertson et al. |
| 6,823,865 B2 | 11/2004 | Drew et al. |
| 6,823,869 B2 | 11/2004 | Raje et al. |
| 6,834,650 B1 | 12/2004 | Fini |
| 6,851,425 B2 | 2/2005 | Jaffre |
| 6,851,428 B2 | 2/2005 | Dennis |
| 6,851,429 B2 | 2/2005 | Bishop |
| 6,860,269 B2 | 3/2005 | Kwok et al. |
| 6,860,270 B2 | 3/2005 | Sniadich |
| 6,871,649 B2 | 3/2005 | Kwok et al. |
| 6,895,965 B2 | 5/2005 | Scarberry et al. |
| 6,907,882 B2 | 6/2005 | Ging |
| 6,914,091 B2 | 7/2005 | Donald et al. |
| 6,918,404 B2 | 7/2005 | Dias da Silva |
| 6,926,004 B2 | 8/2005 | Schumacher |
| 6,938,620 B2 | 9/2005 | Payne, Jr. |
| 6,953,354 B2 | 10/2005 | Edirisuriya et al. |
| 6,959,710 B2 | 11/2005 | Barnett et al. |
| 6,968,844 B2 | 11/2005 | Liland |
| 6,972,003 B2 | 12/2005 | Bierman et al. |
| 6,986,352 B2 | 1/2006 | Frater et al. |
| 6,997,177 B2 | 2/2006 | Wood |
| 7,000,614 B2 | 2/2006 | Lang et al. |
| 7,007,696 B2 | 3/2006 | Palkon et al. |
| 7,011,090 B2 | 3/2006 | Drew et al. |
| 7,018,362 B2 | 3/2006 | Bierman et al. |
| 7,040,321 B2 | 5/2006 | Goebel |
| 7,047,971 B2 | 5/2006 | Ho et al. |
| 7,047,972 B2 | 5/2006 | Ging et al. |
| 7,052,127 B2 | 5/2006 | Harrison |
| 7,059,326 B2 | 6/2006 | Heidmann et al. |
| 7,066,179 B2 | 6/2006 | Eaton et al. |
| 7,066,586 B2 | 6/2006 | da Silva |
| 7,069,932 B2 | 7/2006 | Eaton et al. |
| 7,076,282 B2 | 7/2006 | Munro et al. |
| 7,076,822 B2 | 7/2006 | Pearce |
| 7,080,645 B2 | 7/2006 | Genger et al. |
| 7,093,599 B2 | 8/2006 | Chen |
| 7,100,610 B2 | 9/2006 | Biener et al. |
| 7,101,359 B2 | 9/2006 | Kline et al. |
| 7,107,989 B2 | 9/2006 | Frater et al. |
| 7,111,624 B2 | 9/2006 | Thudor et al. |
| 7,114,497 B2 | 10/2006 | Aylsworth et al. |
| 7,146,976 B2 | 12/2006 | McKown |
| 7,152,599 B2 | 12/2006 | Thomas |
| 7,152,601 B2 | 12/2006 | Barakat et al. |
| 7,178,525 B2 | 2/2007 | Matula, Jr. et al. |
| 7,185,652 B2 | 3/2007 | Gunaratnam et al. |
| 7,191,781 B2 | 3/2007 | Wood |
| 7,207,328 B1 | 4/2007 | Altemus |
| 7,207,335 B2 | 4/2007 | Kwok et al. |
| 7,210,481 B1 | 5/2007 | Lovell et al. |
| 7,216,647 B2 | 5/2007 | Lang et al. |
| 7,219,669 B1 | 5/2007 | Lovell et al. |
| 7,234,466 B2 | 6/2007 | Kwok et al. |
| 7,237,551 B2 | 7/2007 | Ho et al. |
| 7,243,723 B2 | 7/2007 | Surjaatmadja |
| 7,255,107 B1 | 8/2007 | Gomez |
| D550,836 S | 9/2007 | Chandran et al. |
| D552,733 S | 10/2007 | Criscuolo et al. |
| 7,285,255 B2 | 10/2007 | Kadlec et al. |
| 7,290,546 B2 | 11/2007 | Sprinkle et al. |
| 7,302,950 B2 | 12/2007 | Berthon-Jones et al. |
| 7,308,895 B2 | 12/2007 | Wixey et al. |
| 7,318,437 B2 | 1/2008 | Gunaratnam et al. |
| 7,318,439 B2 | 1/2008 | Raje et al. |
| 7,320,323 B2 | 1/2008 | Lang et al. |
| 7,341,060 B2 | 3/2008 | Ging |
| 7,353,826 B2 | 4/2008 | Sleeper et al. |
| 7,353,827 B2 | 4/2008 | Geist |
| 7,357,136 B2 | 4/2008 | Ho et al. |
| 7,441,618 B2 | 10/2008 | Sorg |
| 7,461,656 B2 | 12/2008 | Gunaratnam et al. |
| 7,470,256 B2 | 12/2008 | Lampropoulos et al. |
| 7,481,220 B2 | 1/2009 | Meyer et al. |
| 7,487,772 B2 | 2/2009 | Ging et al. |
| 7,500,480 B2 | 3/2009 | Matula, Jr. et al. |
| 7,503,327 B2 | 3/2009 | Gunaratnam |
| 7,509,958 B2 | 3/2009 | Amarasinghe et al. |
| 7,520,869 B2 | 4/2009 | Lampropoulos et al. |
| 7,523,754 B2 | 4/2009 | Lithgow |
| 7,549,422 B2 | 6/2009 | Frerichs et al. |
| 7,562,658 B2 | 7/2009 | Aus et al. |
| 7,597,100 B2 | 10/2009 | Ging et al. |
| 7,610,916 B2 | 11/2009 | Kwok et al. |
| 7,614,400 B2 | 11/2009 | Lithgow et al. |
| 7,614,401 B2 | 11/2009 | Thompson |
| 7,621,274 B2 | 11/2009 | Sprinkle et al. |
| 7,624,735 B2 | 12/2009 | Ho et al. |
| 7,640,934 B2 | 1/2010 | Zollinger et al. |
| 7,654,263 B2 | 2/2010 | Lang et al. |
| 7,658,189 B2 | 2/2010 | Davidson et al. |
| 7,665,464 B2 | 2/2010 | Kopacko et al. |
| 7,699,808 B2 | 4/2010 | Marrs et al. |
| 7,703,457 B2 | 4/2010 | Barnett et al. |
| 7,708,017 B2 | 5/2010 | Davidson |
| 7,743,767 B2 | 6/2010 | Ging et al. |
| 7,762,259 B2 | 7/2010 | Gunaratnam |
| 7,775,209 B2 | 8/2010 | Biener et al. |
| 7,779,832 B1 | 8/2010 | Ho |
| 7,798,144 B2 | 9/2010 | Kwok et al. |
| 7,814,911 B2 | 10/2010 | Bordewick et al. |
| 7,819,119 B2 | 10/2010 | Ho |
| 7,827,990 B1 | 11/2010 | Melidis et al. |
| 7,841,345 B2 | 11/2010 | Guney et al. |
| 7,856,980 B2 | 12/2010 | Lang et al. |
| 7,856,982 B2 | 12/2010 | Matula, Jr. et al. |
| 7,861,715 B2 | 1/2011 | Jones et al. |
| 7,874,291 B2 | 1/2011 | Ging et al. |
| 7,874,293 B2 | 1/2011 | Gunaratnam et al. |
| 7,878,199 B2 | 2/2011 | Ging et al. |
| 7,900,630 B2 | 3/2011 | Geiselhart et al. |
| 7,900,631 B2 | 3/2011 | Persson |
| 7,900,635 B2 | 3/2011 | Gunaratnam et al. |
| 7,931,024 B2 | 4/2011 | Ho et al. |
| 7,938,116 B2 | 5/2011 | Ging et al. |
| 7,958,893 B2 | 6/2011 | Lithgow et al. |
| 7,967,013 B2 | 6/2011 | Ging et al. |
| 7,967,014 B2 | 6/2011 | Heidmann et al. |
| 7,971,590 B2 | 7/2011 | Frater et al. |
| 7,992,559 B2 | 8/2011 | Lang et al. |
| 7,997,267 B2 | 8/2011 | Ging et al. |
| 8,025,057 B2 | 9/2011 | Ging et al. |
| 8,042,538 B2 | 10/2011 | Ging et al. |
| 8,042,541 B2 | 10/2011 | Amarasinghe et al. |
| 8,042,542 B2 | 10/2011 | Ging et al. |
| 8,042,546 B2 | 10/2011 | Gunaratnam et al. |
| 8,051,850 B2 | 11/2011 | Kwok et al. |
| 8,091,547 B2 | 1/2012 | Thudor et al. |
| 8,091,553 B2 | 1/2012 | Bordewick et al. |
| 8,096,301 B2 | 1/2012 | Smith et al. |
| 8,136,524 B2 | 3/2012 | Ging et al. |
| 8,136,525 B2 | 3/2012 | Lubke et al. |
| 8,186,345 B2 | 5/2012 | Payton et al. |
| 8,186,348 B2 | 5/2012 | Kwok et al. |
| 8,186,352 B2 | 5/2012 | Gunaratnam et al. |
| 8,210,180 B2 | 7/2012 | Gunaratnam |
| 8,220,459 B2 | 7/2012 | Davidson et al. |
| 8,286,636 B2 | 10/2012 | Gunaratnam et al. |
| 8,297,283 B2 | 10/2012 | Hitchcock et al. |
| 8,312,881 B2 | 11/2012 | Gunaratnam et al. |
| 8,312,883 B2 | 11/2012 | Gunaratnam et al. |
| 8,353,294 B2 | 1/2013 | Frater et al. |
| 8,371,301 B2 | 2/2013 | Biener et al. |
| 8,397,728 B2 | 3/2013 | D'Souza et al. |
| 8,402,972 B2 | 3/2013 | Lang et al. |
| 8,443,807 B2 | 5/2013 | McAuley et al. |
| 8,453,641 B2 | 6/2013 | Payton et al. |
| 8,479,741 B2 | 7/2013 | McAuley et al. |
| 8,485,192 B2 | 7/2013 | Davidson et al. |

(56) References Cited

U.S. PATENT DOCUMENTS

| | | |
|---|---|---|
| 8,505,535 B2 | 8/2013 | Jones et al. |
| 8,550,072 B2 | 8/2013 | Thudor et al. |
| 8,714,157 B2 | 5/2014 | McAuley et al. |
| 8,746,250 B2 | 6/2014 | Biener et al. |
| 9,119,931 B2 | 1/2015 | D'Souza et al. |
| 8,944,061 B2 | 2/2015 | D'Souza et al. |
| 8,950,404 B2 | 2/2015 | Formica et al. |
| 8,960,196 B2 | 2/2015 | Henry |
| 9,027,556 B2 | 5/2015 | Ng et al. |
| 9,242,062 B2 | 1/2016 | Melidis et al. |
| 9,265,902 B2 | 2/2016 | Payton et al. |
| 9,381,316 B2 | 7/2016 | Ng et al. |
| 9,962,510 B2 | 5/2018 | Ng et al. |
| 10,183,138 B2 | 1/2019 | Ng et al. |
| 2001/0017134 A1 | 8/2001 | Bahr |
| 2001/0020474 A1 | 9/2001 | Hecker et al. |
| 2002/0014241 A1* | 2/2002 | Gradon ............... A61M 16/109 128/205.25 |
| 2002/0020416 A1 | 2/2002 | Namey |
| 2002/0029780 A1 | 3/2002 | Frater et al. |
| 2002/0046755 A1 | 4/2002 | Devoss |
| 2002/0066452 A1 | 6/2002 | Kessler et al. |
| 2002/0069872 A1 | 6/2002 | Gradon et al. |
| 2002/0108613 A1 | 8/2002 | Gunaratnam et al. |
| 2002/0124849 A1 | 9/2002 | Billette de Villemeur |
| 2002/0143296 A1 | 10/2002 | Russo |
| 2002/0157673 A1 | 10/2002 | Kessler et al. |
| 2002/0174868 A1 | 11/2002 | Kwok et al. |
| 2003/0019495 A1 | 1/2003 | Palkon et al. |
| 2003/0019496 A1 | 1/2003 | Kopacko et al. |
| 2003/0051732 A1 | 3/2003 | Smith et al. |
| 2003/0062048 A1 | 4/2003 | Gradon et al. |
| 2003/0089373 A1 | 5/2003 | Gradon et al. |
| 2003/0168063 A1 | 9/2003 | Gambone et al. |
| 2003/0196655 A1* | 10/2003 | Ging ............... A61M 16/0825 128/201.22 |
| 2003/0196656 A1 | 10/2003 | Moore et al. |
| 2003/0196658 A1* | 10/2003 | Ging ............... A61M 16/0666 128/201.22 |
| 2003/0196662 A1 | 10/2003 | Ging et al. |
| 2004/0025882 A1 | 2/2004 | Madaus et al. |
| 2004/0045550 A1* | 3/2004 | Lang ............... A61M 16/065 128/205.25 |
| 2004/0045551 A1 | 3/2004 | Eaton et al. |
| 2004/0083534 A1 | 5/2004 | Ruiz |
| 2004/0094157 A1 | 5/2004 | Dantanarayana et al. |
| 2004/0106891 A1 | 6/2004 | Langan et al. |
| 2004/0111104 A1 | 6/2004 | Schein et al. |
| 2004/0112384 A1 | 6/2004 | Lithgow et al. |
| 2004/0112385 A1 | 6/2004 | Drew et al. |
| 2004/0118406 A1 | 6/2004 | Lithgow et al. |
| 2004/0127856 A1 | 7/2004 | Johnson |
| 2004/0177850 A1 | 9/2004 | Gradon et al. |
| 2004/0182398 A1 | 9/2004 | Sprinkle et al. |
| 2004/0211428 A1 | 10/2004 | Jones |
| 2004/0216746 A1 | 11/2004 | Jones, Jr. et al. |
| 2004/0216747 A1 | 11/2004 | Jones |
| 2004/0221850 A1 | 11/2004 | Ging et al. |
| 2004/0226566 A1 | 11/2004 | Gunaratnam et al. |
| 2004/0255949 A1* | 12/2004 | Lang ............... A61M 16/0825 128/206.21 |
| 2005/0005940 A1* | 1/2005 | Gunaratnam ..... A61M 16/0622 128/207.11 |
| 2005/0051171 A1 | 3/2005 | Booth |
| 2005/0051176 A1 | 3/2005 | Riggins |
| 2005/0056286 A1 | 3/2005 | Huddart et al. |
| 2005/0061326 A1 | 3/2005 | Payne, Jr. |
| 2005/0072428 A1 | 4/2005 | Ho et al. |
| 2005/0098183 A1 | 5/2005 | Nash et al. |
| 2005/0150495 A1 | 7/2005 | Rittner et al. |
| 2005/0155603 A1 | 7/2005 | Ferichs et al. |
| 2005/0155604 A1 | 7/2005 | Ging et al. |
| 2005/0199242 A1 | 9/2005 | Matula et al. |
| 2005/0205096 A1 | 9/2005 | Matula |
| 2005/0211252 A1 | 9/2005 | Lang et al. |
| 2005/0241644 A1 | 11/2005 | Gunaratnam et al. |
| 2005/0257792 A1 | 11/2005 | Wixey et al. |
| 2006/0042629 A1 | 3/2006 | Geist |
| 2006/0060200 A1 | 3/2006 | Ho et al. |
| 2006/0076019 A1 | 4/2006 | Ho |
| 2006/0118117 A1 | 6/2006 | Berthon-Jones et al. |
| 2006/0124131 A1 | 6/2006 | Chandran et al. |
| 2006/0137690 A1 | 6/2006 | Gunaratnam et al. |
| 2006/0174887 A1 | 8/2006 | Chandran et al. |
| 2006/0207597 A1 | 9/2006 | Wright |
| 2006/0213520 A1 | 9/2006 | Frater et al. |
| 2006/0219246 A1 | 10/2006 | Dennis |
| 2006/0254593 A1 | 11/2006 | Chang |
| 2006/0272646 A1 | 12/2006 | Ho et al. |
| 2006/0283461 A1 | 12/2006 | Lubke et al. |
| 2007/0044804 A1 | 3/2007 | Matula, Jr. et al. |
| 2007/0137653 A1 | 6/2007 | Wood |
| 2007/0144525 A1 | 6/2007 | Davidson et al. |
| 2007/0163600 A1 | 7/2007 | Hoffman |
| 2007/0215161 A1 | 9/2007 | Frater et al. |
| 2007/0267017 A1 | 11/2007 | McAuley et al. |
| 2007/0272249 A1 | 11/2007 | Chandran et al. |
| 2007/0282272 A1 | 12/2007 | Bannon et al. |
| 2008/0004573 A1 | 1/2008 | Kaufmann et al. |
| 2008/0006277 A1 | 1/2008 | Worboys et al. |
| 2008/0047560 A1 | 2/2008 | Veliss et al. |
| 2008/0060649 A1 | 3/2008 | Veliss et al. |
| 2008/0065022 A1 | 3/2008 | Kyvik et al. |
| 2008/0092906 A1 | 4/2008 | Gunaratnam et al. |
| 2008/0110464 A1 | 5/2008 | Davidson et al. |
| 2008/0110469 A1 | 5/2008 | Weinberg |
| 2008/0178875 A1 | 7/2008 | Henry |
| 2008/0178886 A1 | 7/2008 | Lieberman et al. |
| 2008/0200880 A1 | 8/2008 | Kyvik et al. |
| 2008/0257354 A1 | 10/2008 | Davidson et al. |
| 2008/0276937 A1 | 11/2008 | Davidson et al. |
| 2008/0314389 A1 | 12/2008 | Thomas et al. |
| 2009/0044808 A1 | 2/2009 | Guney et al. |
| 2009/0050156 A1 | 2/2009 | Ng et al. |
| 2009/0126739 A1 | 5/2009 | Ng et al. |
| 2009/0139526 A1 | 6/2009 | Melidis et al. |
| 2009/0139527 A1 | 6/2009 | Ng et al. |
| 2009/0151729 A1 | 6/2009 | Judson et al. |
| 2009/0173343 A1 | 7/2009 | Omura et al. |
| 2009/0217929 A1 | 9/2009 | Kwok et al. |
| 2009/0223518 A1 | 9/2009 | Kwok et al. |
| 2009/0223521 A1 | 9/2009 | Howard et al. |
| 2010/0000534 A1 | 1/2010 | Kooij et al. |
| 2010/0000543 A1 | 1/2010 | Berthon-Jones et al. |
| 2010/0018534 A1 | 1/2010 | Veliss et al. |
| 2010/0051034 A1 | 3/2010 | Lynch et al. |
| 2010/0089401 A1 | 4/2010 | Lang et al. |
| 2010/0132717 A1 | 6/2010 | Davidson et al. |
| 2010/0192955 A1 | 8/2010 | Biener et al. |
| 2010/0229869 A1 | 9/2010 | Ging et al. |
| 2010/0282265 A1 | 11/2010 | Melidis et al. |
| 2010/0300447 A1 | 12/2010 | Biener et al. |
| 2010/0319700 A1 | 12/2010 | Ng et al. |
| 2011/0030692 A1 | 2/2011 | Jones et al. |
| 2011/0056497 A1 | 3/2011 | Scheiner et al. |
| 2011/0162655 A1 | 7/2011 | Gunaratnam et al. |
| 2011/0214674 A1 | 9/2011 | Ging et al. |
| 2011/0220110 A1 | 9/2011 | Frater et al. |
| 2011/0220114 A1 | 9/2011 | Lithgow et al. |
| 2011/0226254 A1 | 9/2011 | Lang et al. |
| 2011/0259337 A1 | 10/2011 | Hitchcock et al. |
| 2011/0265791 A1 | 11/2011 | Ging et al. |
| 2012/0017912 A1 | 1/2012 | Ging et al. |
| 2012/0037161 A1 | 2/2012 | Ging et al. |
| 2012/0138063 A1 | 6/2012 | Eves et al. |
| 2012/0174928 A1 | 7/2012 | Raje et al. |
| 2012/0222681 A1 | 9/2012 | Kwok et al. |
| 2012/0266886 A1 | 10/2012 | Davidson et al. |
| 2013/0037033 A1 | 2/2013 | Hitchcock et al. |
| 2013/0081628 A1 | 4/2013 | Davidson et al. |
| 2013/0081629 A1 | 4/2013 | Davidson et al. |
| 2013/0081630 A1 | 4/2013 | Davidson et al. |
| 2013/0081631 A1 | 4/2013 | Davidson et al. |

(56) References Cited

U.S. PATENT DOCUMENTS

| | | | |
|---|---|---|---|
| 2013/0081632 A1 | 4/2013 | Davidson et al. |
| 2013/0086795 A1 | 4/2013 | Davidson et al. |
| 2013/0086796 A1 | 4/2013 | Davidson et al. |
| 2013/0087147 A1 | 4/2013 | Davidson et al. |
| 2013/0087148 A1 | 4/2013 | Davidson et al. |
| 2013/0087149 A1 | 4/2013 | Davidson et al. |
| 2013/0092168 A1 | 4/2013 | Davidson et al. |
| 2013/0092169 A1 | 4/2013 | Frater et al. |
| 2013/0092170 A1 | 4/2013 | Davidson et al. |
| 2013/0133658 A1 | 5/2013 | Ng et al. |
| 2013/0133659 A1 | 5/2013 | Ng et al. |
| 2013/0133660 A1 | 5/2013 | Ng et al. |
| 2013/0312758 A1 | 11/2013 | Jones et al. |
| 2014/0083430 A1 | 3/2014 | Matula |
| 2014/0230814 A1 | 8/2014 | Biener et al. |
| 2014/0261434 A1 | 9/2014 | Ng et al. |
| 2015/0007816 A1 | 1/2015 | D'Souza et al. |
| 2018/0104430 A1 | 4/2018 | Ng et al. |
| 2019/0105455 A1 | 4/2019 | Ng et al. |

FOREIGN PATENT DOCUMENTS

| | | |
|---|---|---|
| AU | 95/16178 | 7/1995 |
| AU | 94/59430 | 10/1995 |
| AU | 95/32914 | 2/1996 |
| AU | 96/51130 | 10/1996 |
| AU | 97/41018 | 4/1998 |
| AU | 98/89312 | 1/1999 |
| AU | 2005100738 | 11/2005 |
| CA | 618807 | 4/1961 |
| CA | 623129 | 7/1961 |
| CA | 1039144 | 9/1978 |
| CN | 2464353 | 12/2001 |
| CN | 1735439 | 2/2006 |
| DE | 185 017 | 5/1907 |
| DE | 284 800 | 11/1913 |
| DE | 459 104 | 4/1928 |
| DE | 701 690 | 1/1941 |
| DE | 30 11 900 | 10/1980 |
| DE | 146 688 | 1/1981 |
| DE | 30 15 279 | 10/1981 |
| DE | 31 49 449 | 10/1982 |
| DE | 159 396 | 3/1983 |
| DE | 33 45 067 | 6/1984 |
| DE | 37 07 952 | 3/1987 |
| DE | 35 37 507 | 4/1987 |
| DE | 35 39 073 | 5/1987 |
| DE | 37 19 009 | 12/1988 |
| DE | 39 27 038 | 2/1991 |
| DE | 40 04 157 | 4/1991 |
| DE | 42 12 259 | 1/1993 |
| DE | 42 33 448 | 4/1993 |
| DE | 43 43 205 | 6/1995 |
| DE | 195 48 380 | 7/1996 |
| DE | 196 03 949 | 8/1997 |
| DE | 297 15 718 | 10/1997 |
| DE | 197 35 359 | 1/1998 |
| DE | 297 23 101 | 7/1998 |
| DE | 197 03 526 | 8/1998 |
| DE | 298 10 846 | 8/1998 |
| DE | 198 17 332 | 1/1999 |
| DE | 198 07 961 | 8/1999 |
| DE | 198 08 105 | 9/1999 |
| DE | 198 40 760 | 3/2000 |
| DE | 200 05 346 | 5/2000 |
| DE | 299 23 141 | 5/2000 |
| DE | 200 17 940 | 2/2001 |
| DE | 199 44 242 | 3/2001 |
| DE | 199 54 517 | 6/2001 |
| DE | 100 02 571 | 7/2001 |
| DE | 199 62 515 | 7/2001 |
| DE | 100 45 183 | 5/2002 |
| DE | 102 13 905 | 10/2002 |
| DE | 10 2004 055 433 | 11/2004 |
| DE | 103 31 837 | 1/2005 |
| DE | 20 2004 018 108 | 2/2005 |
| DE | 103 38 169 | 3/2005 |
| EP | 0 054 154 | 6/1982 |
| EP | 0 252 052 | 1/1988 |
| EP | 0 264 772 | 4/1988 |
| EP | 0 288 937 | 11/1988 |
| EP | 0 334 555 | 9/1989 |
| EP | 0 386 605 | 9/1990 |
| EP | 0 427 474 | 5/1991 |
| EP | 0 462 701 | 12/1991 |
| EP | 0 466 960 | 1/1992 |
| EP | 0 303 090 B1 | 4/1992 |
| EP | 0 549 299 | 6/1993 |
| EP | 0 602 424 | 6/1994 |
| EP | 0 608 684 | 8/1994 |
| EP | 0 658 356 | 6/1995 |
| EP | 1 057 479 | 12/1995 |
| EP | 0 697 225 | 2/1996 |
| EP | 0 178 925 A2 | 4/1996 |
| EP | 0 747 078 | 12/1996 |
| EP | 0 776 679 | 6/1997 |
| EP | 0 821 978 | 2/1998 |
| EP | 0 853 962 | 7/1998 |
| EP | 1 027 905 | 8/2000 |
| EP | 1 057 494 | 12/2000 |
| EP | 1 099 452 | 5/2001 |
| EP | 1 118 346 | 7/2001 |
| EP | 1 163 923 | 12/2001 |
| EP | 1 205 205 | 5/2002 |
| EP | 1 258 266 | 11/2002 |
| EP | 1 334 742 | 8/2003 |
| EP | 1 356 841 | 10/2003 |
| EP | 1 356 843 | 10/2003 |
| EP | 1 360 971 | 11/2003 |
| EP | 1 481 702 | 12/2004 |
| EP | 2 471 566 | 7/2012 |
| EP | 2 471 567 | 7/2012 |
| FR | 780018 | 4/1935 |
| FR | 2 574 657 | 6/1986 |
| FR | 2 658 725 | 8/1991 |
| FR | 2 720 280 | 12/1995 |
| FR | 2 735 030 A1 | 12/1996 |
| FR | 2 749 176 | 12/1997 |
| FR | 2 823 122 | 10/2002 |
| GB | 532 214 | 1/1941 |
| GB | 649 689 | 1/1951 |
| GB | 823 887 | 11/1959 |
| GB | 839937 | 6/1960 |
| GB | 1 395 391 | 5/1975 |
| GB | 1 467 828 | 3/1977 |
| GB | 2 145 335 | 3/1985 |
| GB | 2 147 506 | 5/1985 |
| GB | 2 164 569 | 3/1986 |
| GB | 2 173274 | 10/1986 |
| GB | 2 176 404 | 12/1986 |
| GB | 2 186 801 | 8/1987 |
| GB | 2 267 648 | 12/1993 |
| GB | 2 368 533 | 5/2002 |
| GB | 2 385 533 | 5/2003 |
| JP | S39-13991 | 7/1964 |
| JP | S51-142793 | 11/1976 |
| JP | H03-007173 | 1/1991 |
| JP | H09-216240 | 8/1997 |
| JP | H11-000397 | 1/1999 |
| JP | H11-104256 | 4/1999 |
| JP | H11-508159 | 7/1999 |
| JP | 2000-279520 | 10/2000 |
| JP | 2000-325481 | 11/2000 |
| JP | 2000-515784 | 11/2000 |
| JP | 2002-028240 | 4/2002 |
| JP | 2002-543943 | 12/2002 |
| JP | 2003-175106 | 6/2003 |
| JP | 2003-535657 | 12/2003 |
| JP | 2004-000570 | 1/2004 |
| JP | 2005-337371 | 12/2005 |
| JP | 3802872 | 7/2006 |
| WO | WO 80/01044 | 5/1980 |
| WO | WO 82/03548 | 10/1982 |
| WO | WO 86/06969 | 12/1986 |

(56) References Cited

FOREIGN PATENT DOCUMENTS

| | | |
|---|---|---|
| WO | WO 87/01950 | 4/1987 |
| WO | WO 91/03277 | 3/1991 |
| WO | WO 92/15353 | 9/1992 |
| WO | WO 92/20392 | 11/1992 |
| WO | WO 92/20395 | 11/1992 |
| WO | WO 93/01854 | 2/1993 |
| WO | WO 93/24169 | 12/1993 |
| WO | WO 94/02190 | 2/1994 |
| WO | WO 94/16759 | 8/1994 |
| WO | WO 94/20051 | 9/1994 |
| WO | WO 95/02428 | 1/1995 |
| WO | WO 96/17643 | 6/1996 |
| WO | WO 96/25983 | 8/1996 |
| WO | WO 96/28207 | 9/1996 |
| WO | WO 96/39206 | 12/1996 |
| WO | WO 97/00092 | 1/1997 |
| WO | WO 97/07847 | 3/1997 |
| WO | WO 97/09090 | 3/1997 |
| WO | WO 97/20597 | 6/1997 |
| WO | WO 97/41911 | 11/1997 |
| WO | WO 98/03145 | 1/1998 |
| WO | WO 98/04310 | 2/1998 |
| WO | WO 1998/004311 | 2/1998 |
| WO | WO 98/11930 | 3/1998 |
| WO | WO 98/12965 | 4/1998 |
| WO | WO 98/18514 | 5/1998 |
| WO | WO 98/23305 | 6/1998 |
| WO | WO 98/24499 | 6/1998 |
| WO | WO 98/26829 | 6/1998 |
| WO | WO 98/26830 | 6/1998 |
| WO | WO 98/34665 | 8/1998 |
| WO | WO 98/48878 | 11/1998 |
| WO | WO 1998/057691 | 12/1998 |
| WO | WO 99/16327 | 4/1999 |
| WO | WO 99/25410 | 5/1999 |
| WO | WO 99/43375 | 9/1999 |
| WO | WO 99/58181 | 11/1999 |
| WO | WO 99/61088 | 12/1999 |
| WO | WO 99/65554 | 12/1999 |
| WO | WO 00/20072 | 4/2000 |
| WO | WO 00/21600 | 4/2000 |
| WO | WO 00/3 8772 | 7/2000 |
| WO | WO 00/50121 | 8/2000 |
| WO | WO 00/57942 | 10/2000 |
| WO | WO 00/69521 | 11/2000 |
| WO | WO 00/72905 | 12/2000 |
| WO | WO 00/74758 | 12/2000 |
| WO | WO 00/76568 | 12/2000 |
| WO | WO 00/78381 | 12/2000 |
| WO | WO 00/78384 | 12/2000 |
| WO | WO 01/62326 | 8/2001 |
| WO | WO 01/95965 | 12/2001 |
| WO | WO 01/97892 | 12/2001 |
| WO | WO 01/97893 | 12/2001 |
| WO | WO 02/11804 | 2/2002 |
| WO | WO 02/32491 | 4/2002 |
| WO | WO 02/38221 | 5/2002 |
| WO | WO 02/45784 | 6/2002 |
| WO | WO 03/005931 | 1/2003 |
| WO | WO 03/059427 | 7/2003 |
| WO | WO 03/082406 | 10/2003 |
| WO | WO 03/090827 | 11/2003 |
| WO | WO 03/105921 | 12/2003 |
| WO | WO 2004/007010 | 1/2004 |
| WO | WO 2004/022144 | 3/2004 |
| WO | WO 2004/022145 | 3/2004 |
| WO | WO 2004/022146 | 3/2004 |
| WO | WO 2004/022147 | 3/2004 |
| WO | 2004/041342 A1 | 5/2004 |
| WO | WO 2004/041342 | 5/2004 |
| WO | WO 2004/071565 | 8/2004 |
| WO | WO 2004/073778 | 9/2004 |
| WO | WO 2004/078228 | 9/2004 |
| WO | WO 2004/078230 | 9/2004 |
| WO | WO 2004/096332 | 11/2004 |
| WO | WO 2005/002656 | 1/2005 |
| WO | WO 2005/018523 | 3/2005 |
| WO | WO 2005/021075 | 3/2005 |
| WO | WO 2005/028010 | 3/2005 |
| WO | WO 2005/053781 | 6/2005 |
| WO | WO 2005/063326 | 7/2005 |
| WO | WO 2005/063327 | 7/2005 |
| WO | WO 2005/063328 | 7/2005 |
| WO | WO 2005/086943 | 9/2005 |
| WO | WO 2005/094928 | 10/2005 |
| WO | WO 2005/099801 | 10/2005 |
| WO | WO 2005/110220 | 11/2005 |
| WO | WO 2005/118040 | 12/2005 |
| WO | WO 2005/123166 | 12/2005 |
| WO | WO 2006/000046 | 1/2006 |
| WO | WO 2006/014630 | 2/2006 |
| WO | WO 2006/052653 | 5/2006 |
| WO | WO 2006/069345 | 6/2006 |
| WO | WO 2006/069415 | 7/2006 |
| WO | WO 2006/074513 | 7/2006 |
| WO | WO 2006/074515 | 7/2006 |
| WO | WO 2006/074516 | 7/2006 |
| WO | WO 2006/099658 | 9/2006 |
| WO | WO 2006/102707 | 10/2006 |
| WO | WO 2006/130903 | 12/2006 |
| WO | WO 2006/138416 | 12/2006 |
| WO | WO-2006130903 A1 * 12/2006 ............ A61M 16/06 |  |
| WO | WO 2007/009182 | 1/2007 |
| WO | WO 2007/041751 | 4/2007 |
| WO | WO 2007/041786 | 4/2007 |
| WO | WO 2007/045008 | 4/2007 |
| WO | WO 2007/048174 | 5/2007 |
| WO | WO 2007/053878 | 5/2007 |
| WO | WO 2007/143772 | 12/2007 |
| WO | WO 2007/145534 | 12/2007 |
| WO | WO 2007/147088 | 12/2007 |
| WO | WO 2008/011682 | 1/2008 |
| WO | WO 2008/011683 | 1/2008 |
| WO | WO 2008/040050 | 4/2008 |
| WO | WO 2008/058330 | 5/2008 |
| WO | WO 2008/070929 | 6/2008 |
| WO | WO 2009/026627 | 3/2009 |
| WO | WO 2009/052560 | 4/2009 |
| WO | WO 2009/062265 | 5/2009 |
| WO | WO 2009/108994 | 9/2009 |
| WO | WO 2009/108995 | 9/2009 |
| WO | WO 2009/109004 | 9/2009 |
| WO | WO 2010/028425 | 3/2010 |
| WO | WO 2010/066004 | 6/2010 |

OTHER PUBLICATIONS

Decision Denying Petitioner's Request for Rehearing filed in IPR2017-00218, U.S. Pat. No. 9,381,316, by Fisher & Paykel Healthcare Limited on Aug. 17, 2017 (12 pages).

Decision Denying Petitioner's Request for Rehearing filed in IPR2017-00215, U.S. Pat. No. 9,381,316, by Fisher & Paykel Healthcare Limited on Aug. 17, 2017 (12 pages).

Request for Rehearing filed in IPR2017-00218, U.S. Pat. No. 9,381,316, by Fisher & Paykel Healthcare Limited on Jun. 2, 2017 (19 pages).

Request for Rehearing filed in IPR2017-00215, U.S. Pat. No. 9,381,316, by Fisher & Paykel Healthcare Limited on Jun. 2, 2017 (18 pages).

Decision Denying Institution of Inter Partes Review 37 C.F.R. §42.108, *Fisher & Paykel Healthcare Limited* v. *ResMed Limited*, Case No. IPR2017-00215, U.S. Pat. No. 9,381,316, dated May 3, 2017 (29 pages).

Decision Denying Institution of Inter Partes Review 37 C.F.R. §42.108, *Fisher & Paykel Healthcare Limited* v. *ResMed Limited*, Case No. IPR2017-00218, U.S. Pat. No. 9,381,316, dated May 3, 2017 (25 pages).

Final Office Action dated Apr. 24, 2015 in corresponding U.S. Appl. No. 12/320,663 (41 pages).

Communication dated Mar. 22, 2017 issued in New Zealand Application No. 612787 (2 pages).

(56) References Cited

OTHER PUBLICATIONS

Amended Statement of Case (Clean Copy) dated Mar. 7, 2017 filed by Fisher & Paykel Healthcare Limited in New Zealand Application No. 612787 (14 pages).
Amended Statement of Case (Marked Up Copy) dated Mar. 7, 2017 filed by Fisher & Paykel Healthcare Limited in New Zealand Application No. 612787 (14 pages).
International Search Report for PCT/AU2006/001570, dated Jan. 5, 2007.
http://www.puritanbennett.com/prod/Product.aspx?S1=SPT&S2=&id=233, USPTO to assume before Applicant's filing date*.
Examination Report issued in related New Zealand Appln, No. 567375 (dated Nov. 17, 2009).
Office Action dated Nov. 9, 2012 in related U.S. Appl. No. 12/320,663.
Office Action dated Apr. 25, 2013 in related U.S. Appl. No. 12/320,663.
Further Examination Report dated May 8, 2013 in corresponding New Zealand Appln. No. 597689.
Further Examination Report dated May 24, 2013 in corresponding New Zealand Appln. No. 597689.
Notice of Opposition to Grant of Patent filed Jun. 2, 2015 in corresponding New Zealand Applicatioon No. 612787 (7 pages).
Office Action dated Aug. 15, 2013 in related U.S. Appl. No. 13/870,678.
"Introducing The Sullivan Bubble Mask System—Series 3," USPTO to assume before Applicant's filing date.
"The Sullivan Mask System," USPTO to assume before Applicant's filing date.
"There are a lot of Noses Out There . . . ," dated 1995.
"The Sullivan—APD 2 Nasal CPAP System," USPTO to assume before Applicant's filing date.
"ResMed Origins," USPTO to assume before Applicant's filing date.
Sullivan Comfort—Bi-level System (Operating Manual), dated 2000.
"Modular Mask Components," www.resmed.com/products/standard.htm, captured Dec. 15, 2000.
"Nasal Cushions," www.resmed.com/cushions/cushions.htm, captured Jan. 4, 1997.
"Mask Frames," www.resmed.com/maskframes/mask.htm, captured Jan. 4, 1997.
Statement of Case filed Jun. 29, 2015 in a corresponding New Zealand Application No. 612787 (12 pages).
Proceeding Correspondence dated Jul. 2, 2015, in corresponding New Zealand Application No. 612787 (1 page).
Sullivan Series 1 Cushions (3 pages (Photo-1 to Photo-3)), USPTO to assume before Applicant's filing date.
Sullivan Series 2 Cushions (5 pages (Photo-1 to Photo-5)), USPTO to assume before Applicant's filing date.
Sullivan Series 3 Cushions (5 pages (Photo-1 to Photo-5)), USPTO to assume before Applicant's filing date.
Sullivan Mask Fitting Kit (6 pages (Photo-1 to Photo-6)), USPTO to assume before Applicant's filing date.
ResCare—Sullivan Mask Components Case (7 pages (Photo-1 to Photo-7)), USPTO to assume before Applicant's filing date.
U.S. Appl. No. 13/904,748, filed May 29, 2013.
Deadline for Counterstatement dated Jul. 28, 2015, in corresponding New Zealand Application No. 612787 (1 page).
(Amended) Notice of Opposition to Grant of Patent (Section 21) in corresponding New Zealand Application No. 612787 (7 pages) and red-lined version of same (7 pages).
Third-Party Comments on Proposed Claim Amendments filed Oct. 16, 2015 in corresponding New Zealand Application No. 612787 (5 pages).
Proceeding Correspondence issued Oct. 23, 2015 in corresponding New Zealand Application No. 612787 (2 pages).
Office Action dated Nov. 19, 2015 in a corresponding U.S. Appl. No. 12/320,663 (47 pages).
Proceeding Correspondence issued in corresponding New Zealand Application No. 612787 dated Jan. 11, 2016.
Proceeding Correspondence dated Jan. 10, 2017 issued in New Zealand Application No. 612787 (2 pages).
Amended Statement of Case filed Dec. 23, 2013 by Fisher & Paykel Healthcare Limited in New Zealand Application No. 612787 with markups (16 pages).
Amended Statement of Case filed Dec. 23, 2016 by Fisher & Paykel Healthcare Limited in New Zealand Application No. 612787 without mark ups (14 pages).
Amended Notice of Opposition filed Dec. 23, 2016 by Fisher & Paykel Healthcare Limited in New Zealand Application No. 612787 with mark ups (8 pages).
Amended Notice of Opposition filed Dec. 23, 2016 by Fisher & Paykel Healthcare Limited in New Zealand Application No. 612787 without mark ups (5 pages).
Proceeding Correspondence dated Dec. 8, 2015 issued in corresponding New Zealand Application No. 612787 (1 page) and Submission of Fisher & Paykel Healthcare Limited, filed Nov. 27, 2015, in the same proceeding (3 pages).
International Preliminary Report on Patentability dated Apr. 29, 2008 including the Written Opinion of the International Searching Authority issued in corresponding PCT Application No. PCT/AU2006/001570 (WO 2007/048174).
First Examination Report issued in corresponding New Zealand Application No. 719679 dated May 26, 2016.
Non-final Office Action dated Oct. 8, 2014 in the corresponding U.S. Appl. No. 12/320,663 (36 pages).
9 Photographs of Weinmann mask WM 23122, 1991.
4 additional photographs of "Weinmann Mask," USPTO to assume before Applicant's filing date.
Adam J. Singer MD et al. "The Cyanoacrylate Topical Skin Adhesives," American Journal of Emergency Medicine, vol. 26, 2008, pp. 490-496.
Australian Appln. No. 2005253641—Examiner's First Report, dated Apr. 20, 2010.
Australian Appln. No. 2005253641—Examiner's Report, dated Aug. 18, 2011.
Australian Appln. No. 2006206040—Examination Report, dated Jun. 27, 2012.
Australian Appln. No. 2010251884—Examination Report, dated Jul. 27, 2012.
Chinese Appln. No. 200480011911.9—Office Action (w/English translation), dated Jun. 24, 2010.
Chinese Appln. No. 200580020203.6—Office Action (w/English translation), dated Jun. 1, 2010.
Chinese Appln. No. 200580020203.6—Office Action (w/English translation), dated Jul. 6, 2011.
Chinese Appln. No. 200580020203.6—Office Action (w/English translation), dated Dec. 23, 2011.
Chinese Appln. No. 200580020203.6—Office Action (w/English translation), dated Apr. 18, 2012.
Chinese Appln. No. 200680002169.4—Office Action (w/English translation), dated Mar. 23, 2010.
Chinese Appln. No. 200680002169.4—Third Office Action (w/English translation), dated Nov. 11, 2010.
Chinese Appln. No. 200810109270.0—Office Action (w/English translation), dated Oct. 19, 2011.
Chinese Appln. No. 200810109270.0—Office Action (w/English translation), dated Jun. 27, 2012.
Chinese Appln. No. 200910223650.1—Office Action (w/English translation), dated Mar. 29, 2012.
Chinese Appln. No. 201010000226.3—Office Action (w/English translation), dated Apr. 26, 2012.
Chinese Appln. No. 201010517066.X—Office Action (w/English translation), dated Nov. 10, 2011.
ComfortLite™, Respironics, http://comfortlite.respironics.com, before applicants' filing date.
ComfortLite™ 2, Respironics, http://comfortlite2.respironics.com, USPTO to assume before Applicant's filing date.
"Ear Loop Face Mask" , USPTO to assume before Applicant's filing date.
European Appln. No. EP 01944732.5—Office Action, dated Nov. 27, 2009.

(56) References Cited

OTHER PUBLICATIONS

European Appln. No. EP 02714190.2—Search Report, dated Jul. 11, 2006.
European Appln. No. EP 03793493.2—Supplementary Search Report, dated Dec. 2, 2009.
European Appln. No. EP 03793493.2—Office Action, dated Mar. 18, 2011.
European Appln. No. EP 03810331.3—Supplementary Search Report, dated Dec. 18, 2009.
European Appln. No. EP 04730413.4—Supplementary Search Report, dated Sep. 29, 2009.
European Appln. No. EP 04802114.1—Supplementary Search Report, dated Apr. 27, 2009.
European Appln. No. EP 04802133.1—Supplementary Search Report, dated Sep. 8, 2009.
European Appln. No. EP 04802133.1—Office Action, dated Dec. 22, 2009.
European Appln. No. EP 05746824.1—Supplementary Search Report, dated Dec. 17, 2009.
European Appln. No. EP 05749447.8—Supplementary Search Report, dated Dec. 8, 2009.
European Appln. No. EP 06704287.9—Supplementary Search Report, dated Oct. 6, 2009.
European Appln. No. EP 06704287.9—Office Action, dated Jul. 18, 2011.
European Appln. No. EP 07784697.0—Search Report, dated Jul. 27, 2009.
European Appln. No. EP 07845378.4—Search Report, dated Dec. 1, 2009.
European Appln. No. EP 08154854.7—Extended Search Report, dated Nov. 27, 2008.
European Appln. No. EP 08154854.7—Examination Report, dated Jul. 1, 2011.
European Appln. No. EP 08161249.1—Extended Search Report, dated Mar. 19, 2009.
European Appln No. EP 08161868.8—Search Report, dated Sep. 23, 2008.
European Appln No. EP 09003544.5—Search Report, dated Jun. 2, 2009.
European Appln. No. EP 09161984.1—Extended Search Report, dated Sep. 3, 2009.
European Appln. No. EP 09178736.6—Search Report, dated Apr. 19, 2010.
European Appln. No. EP 10181516.5—Search Report, dated Jun. 13, 2012.
European Appln. No. EP 10182015.7—Search Report, dated Jun. 15, 2012.
European Appln. No. EP 11174401.7—Search Report, dated Oct. 20, 2011.
European Appln. No. EP 11174407.4—Extended Search Report, dated Oct. 20, 2011.
European Appln. No. EP 12154923.2—Extended Search Report, dated Jun. 1, 2012.
European Appln. No. EP 12154926.5—Extended Search Report, dated Jun. 6, 2012.
European Appln. No. EP 12165749.8—Extended Search Report, dated Oct. 10, 2012.
European Appln. No. EP 12165751.4—Extended Search Report, dated Oct. 8, 2012.
Fisher and Paykel Col.—Product Family—http://www.fphcare.com/osa/products.asp/, USPTO to assume before Applicant's filing date.
German Patent No. 101 51 984—Decision from Opposition hearing by Weinmann (w/English translation), dated Dec. 6, 2007.
Hans Rudolph, Inc.—Mask Products—http://www.rudolphkc.com/products.php?category=MASKS, USPTO to assume before Applicant's filing date.
"If You Hate CPAP! You Need CPAP Pro®," www.cpappro.com, USPTO to assume before Applicant's filing date.
Japanese Appln. No. 2003-537718—Office Action (w/English translation), dated Oct. 7, 2008.
Japanese Appln. No. 2003-559587—Office Action (w/English translation), dated Mar. 17, 2009.
Japanese Appln. No. 2005-004072—Office Action (w/English translation), dated Sep. 24, 2009.
Japanese Appln. No. 2005-337371—Reasons for Rejection (w/English translation), dated Feb. 22, 2011.
Japanese Appln. No. 2005-337371—Final Office Action (w/English translation), dated Jan. 31, 2012.
Japanese Appln. No. 2006-504029—Office Action (w/English translation), dated Nov. 10, 2009.
Japanese Appln. No. 2006-545843—Notice of Reasons for Rejection (w/English translation), dated Jun. 7, 2011.
Japanese Appln. No. 2007-515732—Office Action (w/English translation), dated Aug. 24, 2010.
Japanese Appln. No. 2007-515732—Office Action (w/English translation), dated Aug. 16, 2011.
Japanese Appln. No. 2007-515732—Office Action (w/English translation), dated Jun. 12, 2012.
Japanese Appln. No. 2007-550636—Office Action (w/English translation), dated Mar. 18, 2011.
Japanese Appln. No. 2007-550636—Office Action (w/English translation), dated Mar. 21, 2012.
Japanese Appln. No. 2007-550636—Notice of Allowance, dated Jul. 10, 2012.
Japanese Appln. No. 2009-140433—Office Action (w/English translation), dated Aug. 20, 2011.
Japanese Appln. No. 2009-140433—Notice of Allowance, dated Sep. 4, 2012.
Japanese Appln. No. 2010-195597—Office Action (w/English translation), dated Jun. 12, 2012.
Japanese Appln. No. 2010-214485—Office Action (w/English translation), dated Jun. 12, 2012.
Japanese Appln. No. 2010-268127—Notice of Reasons for Rejection (w/English translation), dated Jul. 10, 2012.
Japanese Appln. No. 2011-038110—Office Action (w/English translation), dated Aug. 14, 2012.
Japanese Appln. No. S52-164619—English translation of Figure 1, Dec. 1977.
Joel W. Beam, "Tissue Adhesives for Simple Traumatic Lacerations," Journal of Athletic Training, 2008, vol. 43, No. 2, pp. 222-224.
JP 11-000397A Machine Translation, provided by the Japanese Patent Office, Jan. 6, 2009, full document.
Laurent Brochard, "Pressure Support Ventilation," Chapter 9, Part IV—Conventional Methods of Ventilator Support, pp. 239-257, 1994.
Mask 1 Photographs, Respironics Inc., Reusable Full Mask (small) Part #452033 Lot #951108, USPTO to assume before Applicant's filing date.
Mask 2 Photographs, Puritan—Bennett, Adam Curcuit, Shell Part #231700, Swivel Part #616329-00, Pillows (medium) Part #616324, USPTO to assume before Applicant's filing date.
Mask 3 Photographs, DeVilbiss Healthcare Inc., Devilbiss Seal-Ring and CPAP Mask Kit (medium), Part #73510-669, USPTO to assume before Applicant's filing date.
Mask 4 Photographs, Respironics Inc., Monarch Mini Mask with Pressure Port, Part #572004, Monarch Headgear, Part #572011, USPTO to assume before Applicant's filing date.
Mask 5 Photographs, Healthdyne Technologies, Nasal CPAP Mask (medium narrow), Part #702510, USPTO to assume before Applicant's filing date.
Mask 6 Photographs, Healthdyne Technologies, Soft Series Nasal CPAP Mask, Part #702020, USPTO to assume before Applicant's filing date.
Mask 7 Photographs, DeVilbiss Healthcare Inc., Small Mask and Seal Rings, Part #73510-668, USPTO to assume before Applicant's filing date.
Mask 8 Photographs, Respironics Inc., Reusable Contour Mask (medium), Part #302180, USPTO to assume before Applicant's filing date.
Mask 9 Photographs, Healthdyne Technologies, Healthdyne Large Headgear, USPTO to assume before Applicant's filing date.

(56) References Cited

OTHER PUBLICATIONS

Mask 10 Photographs, Respironics Inc., Soft Cap (medium), Part #302142, USPTO to assume before Applicant's filing date.
Mask 11 Photographs, Weinmann: Hamburg, Nasalmaskensystem mit Schalldämpfer (medium), Part #WN 23105, USPTO to assume before Applicant's filing date.
Mask 12 Photographs, Life Care, USPTO to assume before Applicant's filing date.
Mask 13 Photographs, Healthdyne Technologies, USPTO to assume before Applicant's filing date.
Mark 14 Photographs, King System, USPTO to assume before Applicant's filing date.
Mask 15 Photographs, Respironics Inc., Pediatric Mask, USPTO to assume before Applicant's filing date.
Mask 16 Photographs, Hans Rudolph Inc., Hans Rudolph Silicone Rubber Face Mask/8900, USPTO to assume before Applicant's filing date.
McPherson et al., "Respiratory Therapy Equipment," Chapter 8, Third Edition, Introduction to Ventilators, pp. 230-253, 1985.
Merriam-Webster Online Dictionary definition of moveable from the 14th century, USPTO to assume before Applicant's filing date.
New Zealand Appln. No. 2003275762—Examiner's Report No. 3, dated Nov. 18, 2009.
New Zealand Appln. No. 539836—Examination Report, dated Aug. 25, 2005.
New Zealand Appln. No. 564877—Examination Report, dated Dec. 2, 2009.
New Zealand Appln. No. 587344—Examination Report, dated Jan. 19, 2012.
New Zealand Appln. No. 587344—Examination Report, dated Aug. 3, 2012.
New Zealand Appln. No. 587820—Examination Report, dated Sep. 13, 2010.
New Zealand Appln. No. 597552—Examination Report, dated Jan. 19, 2012.
PCT/AU2003/001163—International Search Report, dated Nov. 4, 2003.
PCT/AU2003/001471—International Search Report, dated Feb. 12, 2004.
PCT/AU2004/000563—International Search Report, dated Jun. 23, 2004.
PCT/AU2004/001760—International Search Report, dated Jan. 12, 2005.
PCT/AU2004/001760—International Preliminary Report on Patentability, dated Jul. 3, 2006.
PCT/AU2004/001813—International Search Report, dated Mar. 7, 2005.
PCT/AU2004/001813—International Preliminary Report on Patentability, dated Jul. 3, 2006.
PCT/AU2004/001832—International Search Report, dated Mar. 24, 2005.
PCT/AU2004/001832—International Preliminary Report on Patentability, dated Jul. 3, 2006.
PCT/AU2005/000803—International Search Report, dated Jun. 30, 2005.
PCT/AU2005/000850—International Search Report, dated Aug. 12, 2005.
PCT/AU2005/000850—International Preliminary Report on Patentability, dated Dec. 20, 2006.
PCT/AU2006/000032—International Search Report, dated May 15, 2006.
PCT/AU2006/000032—International Preliminary Report on Patentability, dated Jul. 17, 2007.
PCT/AU2006/000770—International Search Report, dated Aug. 3, 2006.
PCT/AU2007/001051—International Search Report, dated Nov. 5, 2007.
PCT/AU2007/001052—International Search Report, dated Oct. 9, 2007.
PCT/AU2007/001456—International Search Report, dated Dec. 12, 2007.
PCT/AU2007/001936—International Search Report, dated Mar. 4, 2008.
PCT/AU2009/000240—International Search Report, dated May 21, 2009.
PCT/AU2009/000241—International Search Report, dated May 18, 2009.
PCT/AU2009/000262—International Search Report, dated Jun. 9, 2009.
PCT/AU2009/001102—International Search Report, dated Dec. 11, 2009.
PCT/AU2009/001144—International Search Report, dated Dec. 8, 2009.
PCT/AU2010/000657—International Search Report, dated Sep. 9, 2010.
Photograph of Weinmann mask, acquired prior to 1998.
Product Brochure for ResMed "Sullivan® Mirage™—The Mirage is Real. A Perfect Fit-First Time," © 1997 ResMed Limited, 4 pages.
Product Brochure for ResMed "Sullivan® Mirage™—The Mirage is Real. A Perfect Fit-First Time," © 1998 ResMed Limited, 4 pages.
ResMed Co.—Mask Products—http://resmed.com/portal/site/ResMedUS/index.jsp?, USPTO to assume before Applicant's filing date.
ResMed Ltd., "Improving patient compliance with The ResMed Range of Mask Systems The Ultimate Interface for CPAP treatment," USPTO to assume before Applicant's filing date, 4 pages.
Respironics Co.—Mask Family—http://masksfamily.respironics.com/, USPTO to assume before Applicant's filing date.
Snapp Nasal Interface, Tiara Medical Systems, Inc.—http://tiaramed.com/asp_shops/shopdisplayproducts.asp?id=109&cat=SNAPP%2A+Nasal+Interface, USPTO to assume before Applicant's filing date.
"Somnomask" brochure, 1999 along with various invoices relating to the "Somnomask".
Somnotron CPAP-Great WM 2300 Instmction Manual, Weinmann Hamburg, 1991, 11 pages.
Subbu Venkatraman et al., "Review Skin Adhesives and Skin Adhesion 1. Transdermal Drug Delivery Systems," Biomaterials, vol. 19, 1998, pp. 1119-1136.
The ResMed Range of Mask Systems, product brochure, Nov. 1995, 4 pages.
Unsolicited email from Elson Silva, PhD, dated Mar. 28, 2008, "Requesting IDS of U.S. Pat. No. 6,766,817 for patents on fluids moving on porosity by Unsaturated Hydraulic Flow," (email provided in both HIML and plain text format).
U.S. Appl. No. 12/083,779—Office Action including PTO-892 listings, dated Feb. 17, 2012.
U.S. Appl. No. 12/083,779—Office Action including PTO-892 listings, dated Sep. 28, 2012.
U.S. Appl. No. 13/619,666, "Cushion for Patient Interface"—Gunaratnam et al., filed Sep. 14, 2012.
U.S. Appl. No. 13/676,736, "Cushion for Patient Interface"—Davidson et al., filed Nov. 14, 2012.
U.S. Appl. No. 13/676,869, "Cushion for Patient Interface"—Davidson et al., filed Nov. 14, 2012.
U.S. Appl. No. 13/676,925, "Cushion for Patient Interface"—Davidson et al., filed Nov. 142012.
U.S. Appl. No. 13/687,680, "Cushion for Patient Interface"—Davidson et al., filed Nov. 28, 2012.
U.S. Appl. No. 13/688,575, "Cushion for Patient Interface"—Davidson et al., filed Nov. 29, 2012.
U.S. Appl. No. 13/688,619, "Cushion for Patient Interface"—Davidson et al., filed Nov. 29, 2012.
U.S. Appl. No. 13/688,875, "Cushion for Patient Interface"—Davidson et al., filed Nov. 29, 2012.
U.S. Appl. No. 13/688,890, "Cushion for Patient Interface"—Davidson et al., filed Nov. 29, 2012.
U.S. Appl. No. 13/688,931, "Cushion for Patient Interface"—Davidson et al., filed Nov. 29, 2012.
U.S. Appl. No. 13/689,094, "Cushion for Patient Interface"—Davidson et al., filed Nov. 29, 2012.
U.S. Appl. No. 13/689,210, "Cushion for Patient Interface"—Davidson et al., filed Nov. 29, 2012.

(56) References Cited

OTHER PUBLICATIONS

U.S. Appl. No. 13/689,211, "Cushion for Patient Interface"—Davidson et al., filed Nov. 29, 2012.
U.S. Appl. No. 13/708,049, "Respiratory Mask Assembly"—Frater et al., filed Dec. 7, 2012.
U.S. Appl. No. 60/424,686, filed Nov. 8, 2002 (expired).
U.S. Appl. No. 60/483,622, filed Jul. 1, 2003 (expired).
U.S. Appl. No. 60/533,214, filed Dec. 31, 2003 (expired).
U.S. Appl. No. 60/634,802, filed Dec. 10, 2004 (expired).
U.S. Appl. No. 60/643,121, filed Jan. 12, 2005 (expired).
U.S. Appl. No. 60/645,672, filed Jan. 21, 2005 (expired).
U.S. Appl. No. 60/795,615, filed Apr. 28, 2006 (expired).
U.S. Appl. No. 60/833,841, filed Jul. 28, 2006 (expired).
U.S. Appl. No. 60/835,442, filed Aug. 4, 2006 (expired).
U.S. Appl. No. 60/852,649, filed Oct. 19, 2006 (expired).
U.S. Appl. No. 60/874,968, filed Dec. 15, 2006 (expired).
U.S. Appl. No. 60/907,856, filed Apr. 19, 2007 (expired).
U.S. Appl. No. 60/924,241, filed May 4, 2007 (expired).
U.S. Appl. No. 60/929,393, filed Jun. 25, 2007 (expired).
U.S. Appl. No. 60/935,179, filed Jul. 30, 2007 (expired).
U.S. Appl. No. 60/935,336, filed Aug. 8, 2007 (expired).
U.S. Appl. No. 60/996,160, filed Nov. 5, 2007 (expired).
U.S. Appl. No. 61/006,409, filed Jan. 11, 2008 (expired).
U.S. Appl. No. 61/064,818, filed Mar. 28, 2008 (expired).
U.S. Appl. No. 61/071,512, filed May 2, 2008 (expired).
U.S. Appl. No. 61/213,326, filed May 29, 2009 (expired).
U.S. Appl. No. 61/222,711, filed Jul. 2, 2009 (expired).
U.S. Appl. No. 61/263,175, filed Nov. 20, 2009 (expired).
U.S. Appl. No. 61/272,162, filed Aug. 25, 2009 (expired).
U.S. Appl. No. 61/272,250, filed Sep. 4, 2009 (expired).
Webster's New World Dictionary, Third College Edition 1988, definition for engaged and flexible, USPTO to assume before Applicant's filing date.
Webster's Third New International Dictionary, 1993, Dictionary definition for adjustable, bendable, and mild steel, USPTO to assume before Applicant's filing date.
Amended Notice of Opposition to Grant of Patent filed by Fisher & Paykel Healthcare Limited in New Zealand Patent Application No. 622665 and Statement of Case filed on Oct. 30, 2014 (27 pages).
Amended Notice of Opposition to Grant of Patent filed by Fisher & Paykel Healthcare Limited in New Zealand Patent Application No. 622670 and Statement of Case filed on Oct. 30, 2014 (27 pages).
Amended Notice of Opposition to Grant of Patent filed by Fisher & Paykel Healthcare Limited in New Zealand Patent Application No. 607032 and Statement of Case filed on Oct. 30, 2014 (27 pages).
Amended Notice of Opposition to Grant of Patent filed by Fisher & Paykel Healthcare Limited in New Zealand Patent Application No. 622666 and Statement of Case filed on Oct. 30, 2014 (26 pages).
Statement of Grounds and Particulars filed by Fisher & Paykel Healthcare Limited in Australian Patent Application No. 2009221630 filed Jan. 19, 2015 (21 pages).
Proceeding Correspondence dated Aug. 28, 2018 issued in New Zealand Application No. 612787 (2 pages).
Second Amended Statement of Case (Marked Up Copy) dated Aug. 13, 2018 filed by Fisher & Paykel Heathcare Limited in New Zealand Application No. 612787 (23 pages).
Second Amended Statement of Case (Clean Copy) dated Aug. 13, 2018 filed by Fisher & Paykel Heathcare Limited in New Zealand Application No. 612787 (20 pages).
Petition for Inter Partes Review of U.S. Pat. No. 9,381,316 filed Nov. 8, 2016 by Fisher & Paykel Healthcare Limited (IPR2017-00215) (111 pages) ("IPR2017-00215").
Petition for Inter Partes Review of U.S. Pat. No. 9,381,316 filed Nov. 8, 2016 by Fisher & Paykel Healthcare Limited (IPR2017-00218) (103 pages) ("IPR2017-00218").
Declaration of Jason Eaton, P.E., in Support of Petition for Inter Partes review of U.S. Pat. No. 9,381,316 [Exhibit 1009, Petition for Inter Partes Review of U.S. Pat. No. 9,381,316 filed Nov. 8, 2016 by Fisher & Paykel Healthcare Limited (IPR2017-00215)] (143 pages) ("Eaton '215 Dec.").
Declaration of Jason Eaton, P.E., in Support of Petition for Inter Partes Review of U.S. Pat. No. 9,381,316 [Exhibit 1107, Petition for Inter Partes Review of U.S. Pat. No. 9,381,316 filed Nov. 8, 2016 by Fisher & Paykel Healthcare Limited (IPR2017-00218)] (122 pages) ("Eaton '218 Dec.").
Complaint for Patent Infringement, *ResMed Inc.* v. *Fisher & Paykel Healthcare Corp. Ltd.*, Case No. 3:16-cv-02072-JLS-MDD (S.D. Cal.) [Exhibit 1013, Petition for Inter Partes Review of U.S. Pat. No. 9,381,316 filed Nov. 8, 2016 by Fisher & Paykel Healthcare Limited (IPR2017-00215)/ Exhibit 1109, Petition for Inter Partes Review of U.S. Pat. No. 9,381,316 filed Nov. 8, 2016 by Fisher & Paykel Healthcare Limited (IPR2017-00218)] (65 pages) ("Complaint").
Answer of ResMed Corp. to Complaint for Patent Infringement and Counterclaims, *Fisher & Paykel Healthcare Ltd.* v. *ResMed Corp.*, Case No. 3:16-cv-02068-DMS-WVG (S.D. Cal.) [Exhibit 1014, Petition for Inter Partes Review of U.S. Pat. No. 9,381,316 filed Nov. 8, 2016 by Fisher & Paykel Healthcare Limited (IPR2017-00215)/ Exhibit 1110, Petition for Inter Partes Review of U.S. Pat. No. 9,381,316 filed Nov. 8, 2016 by Fisher & Paykel Healthcare Limited (IPR2017-00218)] (95 pages) ("Answer").
Excerpts from the U.S. Patent and Trademark Office File History of U.S. Pat. No. 9,381,316, Exhibit 1010, Petition for Inter Partes Review of U.S. Pat. No. 9,381,316 filed Nov. 8, 2016 by Fisher & Paykel Healthcare Limited (IPR2017-00215) (655 pages).
Excerpts from the U.S. Patent and Trademark Office File History of U.S. Pat. No. 9,381,316, Exhibit 1108, Petition for Inter Partes Review of U.S. Pat. No. 9,381,316 filed Nov. 8, 2016 by Fisher & Paykel Healthcare Limited (IPR2017-00218)] (655 pages).
Statutory Declaration of Daniel Anthony Hearn, dated Nov. 16, 2016, in the opposition proceeding in corresponding New Zealand Application No. 612787 (45 pages) ("Hearn Dec.").
Fisher & Paykel MR810 Respiratory Humidifier Technical Manual, Revision C, Copyright 2004, Fisher & Paykel Healthcare Ltd., Auckland, New Zealand ("F&P MR810 Manual") (43 pages).
HC200 Series Nasal CPAP Blower & Heated Humidifier Manual, Fisher & Paykel Healthcare, May 1998 ("HC200 Manual") (17 pages).
Second Statutory Declaration of Alastair Edwin McAuley, dated Nov. 17, 2016, in the opposition proceeding in corresponding New Zealand Application No. 612787 (81 pages) ("McAuley Dec.").
Statutory Declaration of Dr. David Maurice Rapoport, dated Nov. 17, 2016, in the opposition proceeding in corresponding New Zealand Application No. 612787 (79 pages) ("Rapoport Dec.").
First Examination Report dated Dec. 8, 2017 issued in New Zealand Application No. 737590 (2 pages).
Further Examination Report dated Jan. 9, 2018 issued in New Zealand Application No. 719679 (2 pages).
Second Amended Notice of Opposition (Marked Up Copy) dated Aug. 13, 2018 filed by Fisher & Paykel Healthcare Limited in New Zealand Application No. 612787 (5 pages).
Second Amended Notice of Opposition (Clean Copy) dated Aug. 13, 2018 filed by Fisher & Paykel Heathcare Limited in New Zealand Application No. 612787 (4 pages).
Ng et al., U.S. Appl. No. 16/216,115, filed Dec. 11, 2018, for "Interchangeable Mask Assembly," (parent application).

\* cited by examiner

INTERCHANGEABLE MASK ASSEMBLY

CROSS REFERENCE TO RELATED APPLICATIONS

This application is a continuation of U.S. patent application Ser. No. 16/216,115, filed Dec. 11, 2018, which is a continuation of U.S. patent application Ser. No. 15/841,488, filed Dec. 14, 2017, now U.S. Pat. No. 10,183,138, which is a continuation of U.S. patent application Ser. No. 14/289,158, filed May 28, 2014, now U.S. Pat. No. 9,962,510, which is a continuation of U.S. patent application Ser. No. 12/083,779, filed Jan. 6, 2009, which is the U.S. national phase of International Application No. PCT/AU2006/001570, filed Oct. 24, 2006 which designated the U.S. and claims the benefit of U.S. Provisional Application No. 60/729,746, filed Oct. 25, 2005, each of which is incorporated herein by reference in its entirety.

FIELD OF THE INVENTION

The present invention relates to a nasal assembly used for treatment, e.g., of Sleep Disordered Breathing (SDB) with Continuous Positive Airway Pressure (CPAP) or Non-Invasive Positive Pressure Ventilation (NPPV).

BACKGROUND OF THE INVENTION

Interfaces, such as a nasal mask assembly, for use with blowers and flow generators in the treatment of sleep disordered breathing (SDB) typically include a soft-face contacting portion, such as a cushion, and a rigid shell or frame. In use, the interface is held in a sealing position by headgear so as to enable a supply of air at positive pressure (e.g. 2-30 cm $H_2O$) to be delivered to the user's or patient's or user's airways.

One factor in the efficacy of therapy and compliance of patients with therapy is the comfort and fit of the patient interface. It has been necessary to design a wide variety of masks to best treat and/or suit the user's needs. While there are a large number of patient interfaces, typically each cushion has been specially designed to be used with only a single frame, headgear, etc.

Puritan Bennett includes a mask commercially sold under the name of Breeze® that allows a cushion sold under the name of DreamSeal® to be retrofit to it. Further details of such mask are disclosed at the website http://www.puritan-bennett.com/prod/Product.aspx?S1=SPT&S2=&id=233.

BRIEF SUMMARY OF THE INVENTION

One aspect of the present invention is to provide a mask assembly including at least one main component that can be used with a variety of different styles or types of mask assemblies.

In one embodiment of the invention, there is provided a system of breathing arrangements for delivering breathable gas to a patient, comprising at least first and second cushion components that are different from one another in at least one aspect, and a common frame assembly configured to support each of the first and second cushion components.

In another embodiment of the invention, there is provided a mask assembly for a user comprising a frame having a main body and lateral connector portions; and a cushion component provided to the frame and defining a breathing cavity configured to accommodate at least a portion of the user's nose in use, said cushion component including a face contacting seal portion adapted to sealingly engage with at least a portion of the user's nose in use, said cushion component having an aperture to communicate pressurized gas from the breathing chamber to the user's airways in use, and a main wall portion, opposite from the aperture, extending upwardly away from the frame, said main wall portion including a stiffening portion.

In another embodiment of the invention, there is provided a mask assembly for a user comprising a frame having a main body and lateral connector portions; and a cushion component provided to the frame and defining a breathing cavity configured to accommodate at least a portion of the user's nose in use, said cushion component including a face contacting seal portion adapted to sealingly engage with at least a portion of the user's nose in use, said cushion component having an aperture to communicate pressurized gas from the breathing chamber to the user's airways in use, and a main wall portion, opposite from the aperture, extending upwardly away from the frame, said frame being configured for positioning beneath the nose and between the user's upper lip and nose in use.

In another embodiment of the invention, a mask assembly for a user comprising a frame having a main body and lateral connector portions; a cushion component provided to the frame and defining a breathing cavity configured to accommodate at least a portion of the user's nose in use, said cushion component including a face contacting seal portion adapted to sealingly engage with at least a portion of the user's nose in use, said cushion component having an aperture to communicate pressurized gas from the breathing chamber to the user's airways in use, and a main wall portion, opposite from the aperture, extending upwardly away from the frame, said cushion having an upper portion and a lower portion, wherein at least the upper portion includes a nose height adjusting member.

In another embodiment of the invention, there is provided a mask assembly for a user comprising a frame; a cushion component provided to the frame and defining a breathing cavity configured to accommodate at least a portion of the user's nose in use, said cushion component including a face contacting seal portion adapted to sealingly engage with at least a portion of the user's nose in use, said cushion component having an aperture to communicate pressurized gas from the breathing chamber to the user's airways in use, and a main wall portion, opposite from the aperture, extending upwardly away from the frame; and a frame adjustment member to adjust the position of the cushion component relative to the frame.

In another embodiment of the invention, there is provided a mask assembly for a user comprising a frame; a cushion component provided to the frame and defining a breathing cavity configured to accommodate at least a portion of the user's nose in use, said cushion component including a face contacting seal portion adapted to sealingly engage with at least a portion of the user's nose in use, said cushion component having an aperture to communicate pressurized gas from the breathing chamber to the user's airways in use and a main wall portion, opposite from the aperture, extending upwardly away from the frame; and a chin strap assembly including an extension member provided to each side of the frame and a chin strap having a main chin support portion and straps coupled to the extension members.

In another embodiment of the invention, there is provided a mask assembly for a user comprising a common frame; a cushion component provided to the frame and including a pair of nasal prongs or nozzles adapted to engage the user's nares in use; and a supplemental cushion component in the form of a nasal cushion or a full-face cushion, wherein the cushion component and the supplemental cushion component cooperatively seal with the user's face in use.

These and other aspects of the invention will be described in or apparent from the following detailed description of embodiments.

BRIEF DESCRIPTION OF THE DRAWINGS

Preferred embodiments of the invention will be described in relation to the following figures, in which.

DETAILED DESCRIPTION OF EMBODIMENTS

The following description is provided in relation to several embodiments which may share common characteristics and/or features. It is understood that one or more features of any one embodiment may be combinable with one or more features of the other embodiments which combinations form additional embodiments.

Figure 1:
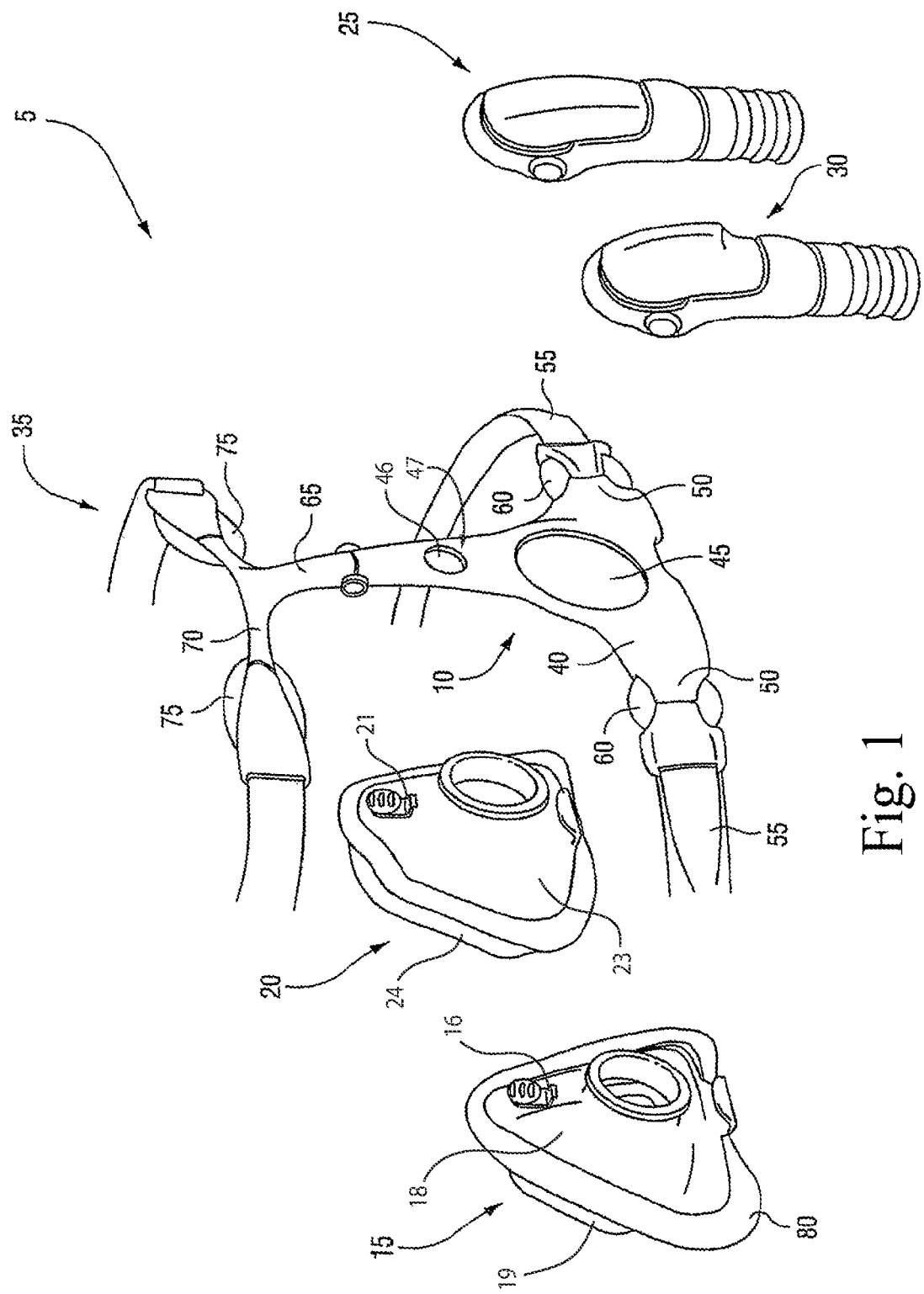
FIG. 1 is a schematic view of a mask assembly according to an embodiment of the present invention.

1.0 First Embodiment—Common Frame with Activa™ or UltraMirage™ Cushion Component FIG. 1 illustrates an interchangeable mask system 5 according to an embodiment of the present invention. Mask system includes a common frame component 10, one of two cushion components 15, 20, one of two elbow components 25, 30, and headgear 35. The mask system is intended for use in positive pressure therapy for users with obstructive sleep apnea (OSA) or another respiratory disorder.

The common frame 10 has a main body 40 defining a central or lower opening 45. The common frame 10 includes an upper opening 46 that is spaced apart and superior to the lower opening 45. Main body 40 includes at least two lateral arms 50, each of which can be coupled to a headgear strap 55 of headgear. The straps may be connected to the frame using a press-fit connector 60, as is known in the art. Common frame 10 may also include a forehead support 65 that has a bridge 70 provided with forehead pads 75 to rest against the user's forehead in use. Forehead support may be adjustably mounted to the common frame, in a manner known in the art.

Common frame 10 is configured to be selectively coupled to one of cushion components 15, 20 and to one of elbow components 25, 30. Each of the cushion components 15, 20 includes a sealing portion 19, 24 constructed and arranged to form a seal with a patient's face. A cushion retainer 18, 23 is configured to releasably couple each cushion component 15, 20 to the main body 40. The cushion component 15, 20 and the cushion retainer 18, 23 form at least a portion of a breathing chamber. Each cushion retainer 18, 23 includes a cushion retainer part 16, 21 structured and arranged to engage behind a retainer part 47 provided to the main body 40 to releasably couple each cushion retainer 18, 23 to the main body 40. Cushion components 15, 20 differ in at least one respect such that one may be more optimal or preferable for use with one user, while another may be more suitable or preferably for use with another user. For example, cushion component 15 may be an Activa™ component, while cushion component 20 may be an UltraMirage™ Series II cushion component, both available from ResMed. These cushion components can be significantly different from one another, e.g., the Activa™ includes a gusset portion 80 and a cushion clip assembly (not shown) which is not incorporated in the UltraMirage™ cushion design.

Common frame 10 is also configured for use with either elbow component 25, or elbow component 30. Elbow components differ in at least one respect, e.g., each may include gas washout vents that are configured for predetermined washout rates, noise, etc.

Common frame 10 is advantageous since it works with a plurality of different cushion components, elbow components, forehead supports, etc., thereby eliminating the need to specifically make the frame for a particular peripheral component, as is the standard.

Figure 2:
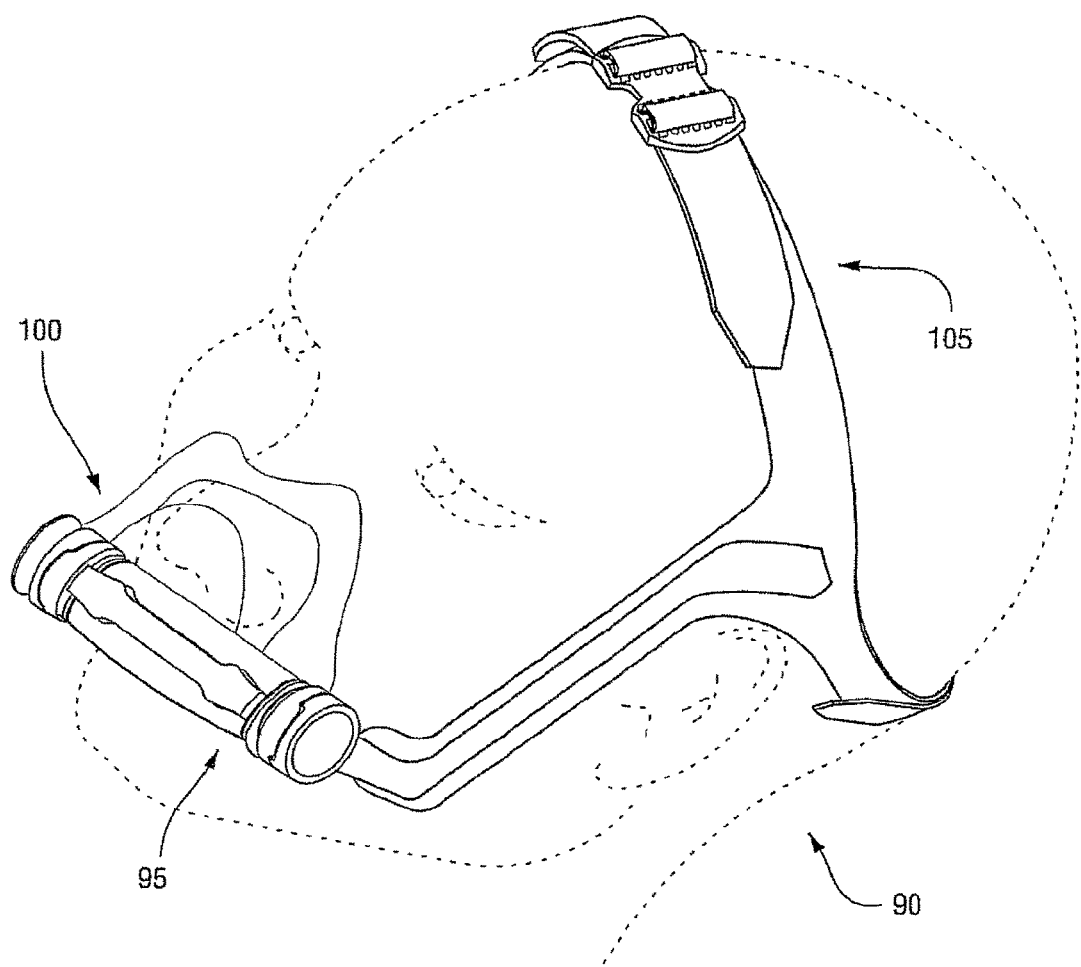
FIGS. 2-13 are views of a mask assembly according to another embodiment of the present invention.

2.0 Second Embodiment—Common SWIFT™ Frame with VISTA™ Cushion Component—Below the Nose FIGS. 2-13 show a mask system 90 according to another embodiment of the present invention. As shown in FIG. 2, mask system 90 includes a common frame 95, a cushion component 100 and a common headgear assembly 105.

Figure 3:
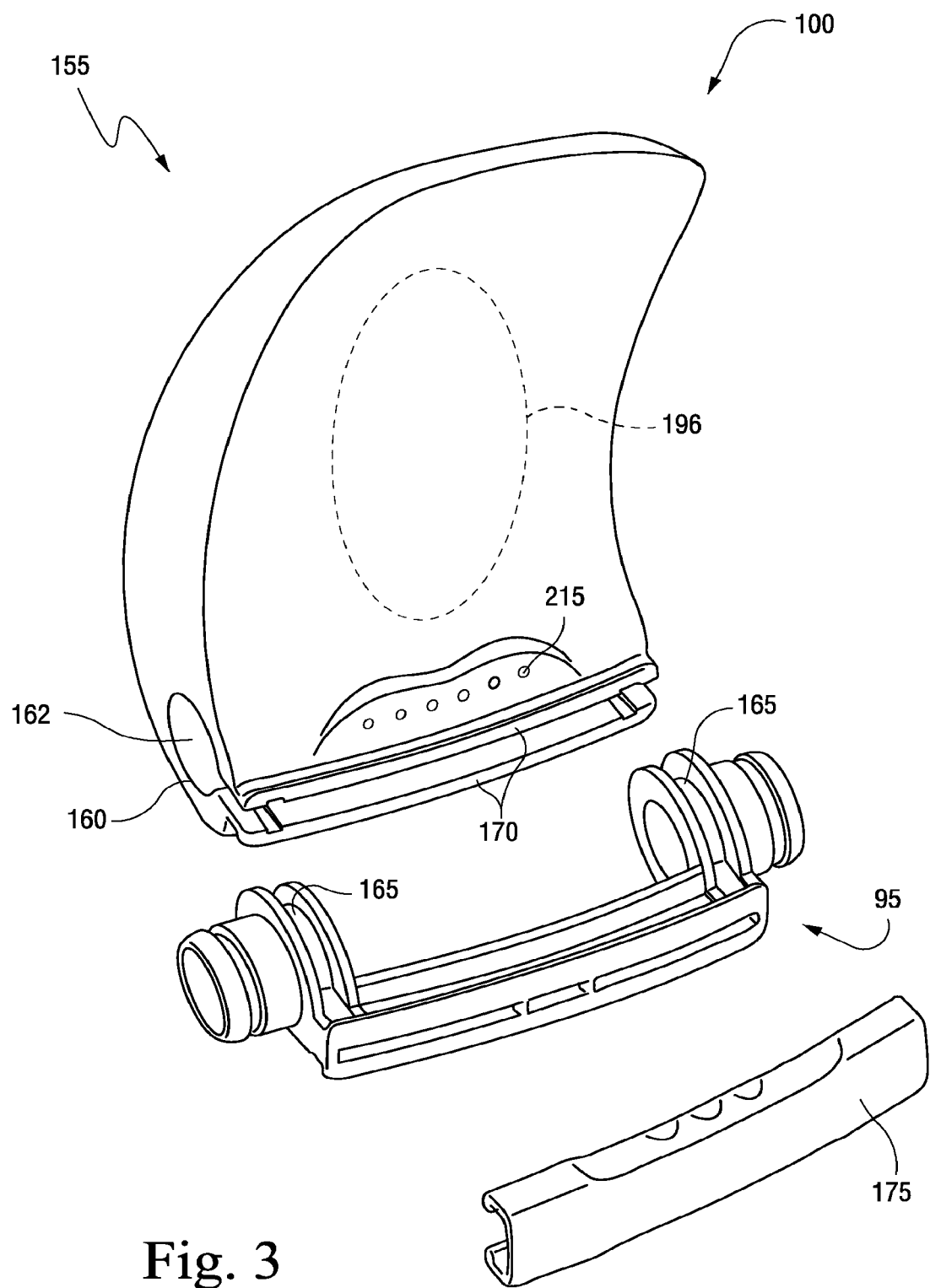
Figure 4:
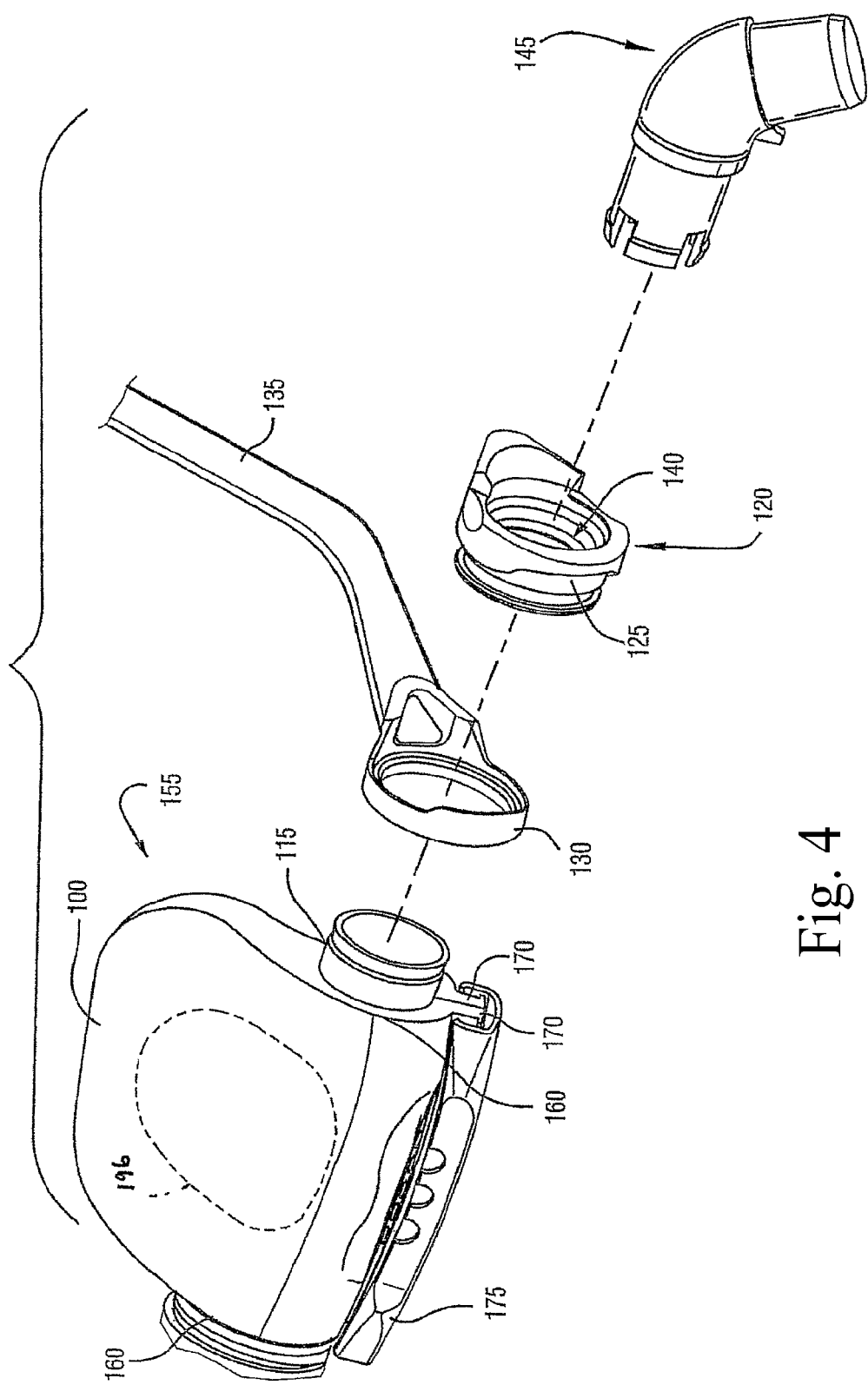

Common frame is similar to ResMed's SWIFT™ frame, described in more detail in relation to U.S. patent application Ser. No. 10/781,929, filed Feb. 20, 2004, incorporated herein by reference in its entirety. As shown in FIG. 3, common frame includes a main body 110 including two lateral connectors 115. Each lateral connector 115 is provided with a seal portion 120 (FIG. 4). Each seal portion 120 has a channel 125 structured to receive and support a ring shaped portion 130 of a yoke 135 of the headgear assembly 105. Each seal portion 120 also includes an aperture 140 to receive either an elbow 145 or a plug 150. In an alternative, each seal portion 120 may receive an elbow 145, i.e., receive two sources of gas (without the plug).

Figure 5:
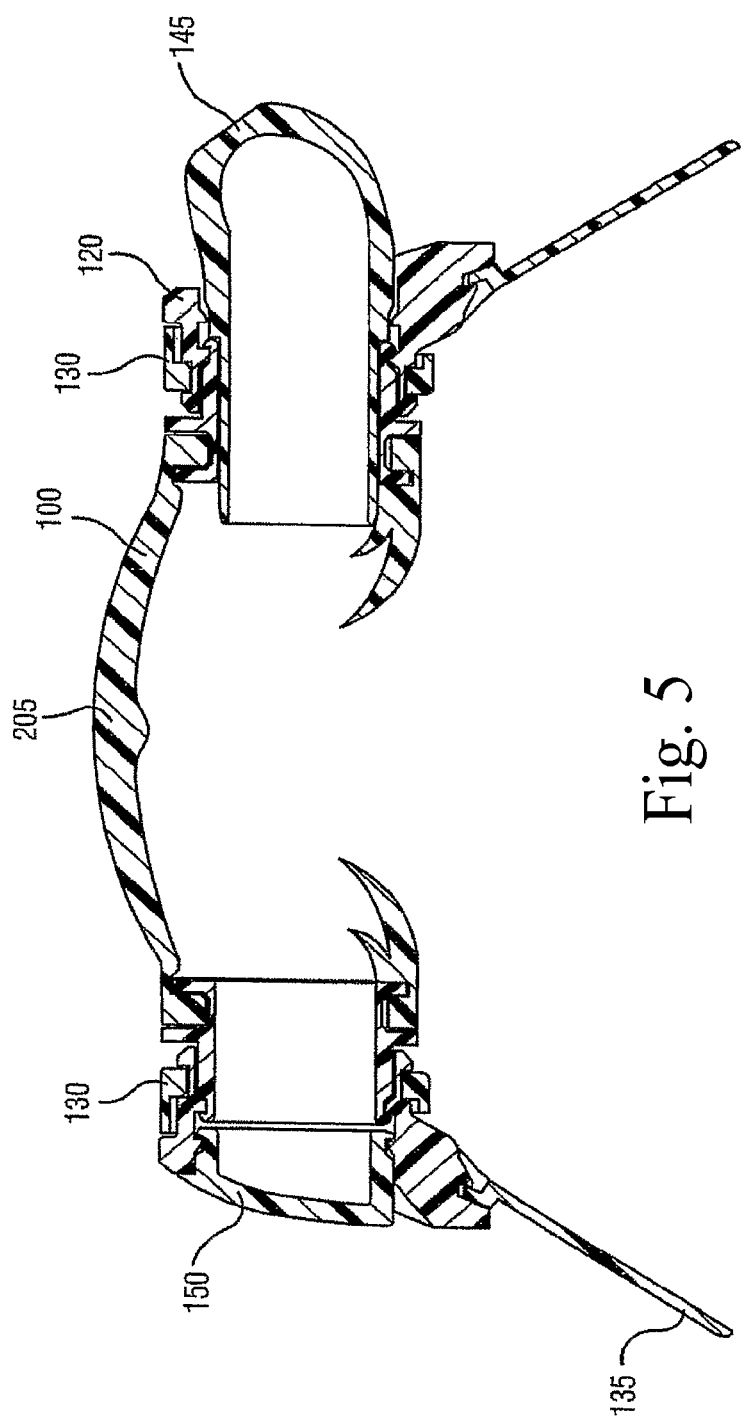
Figure 6:
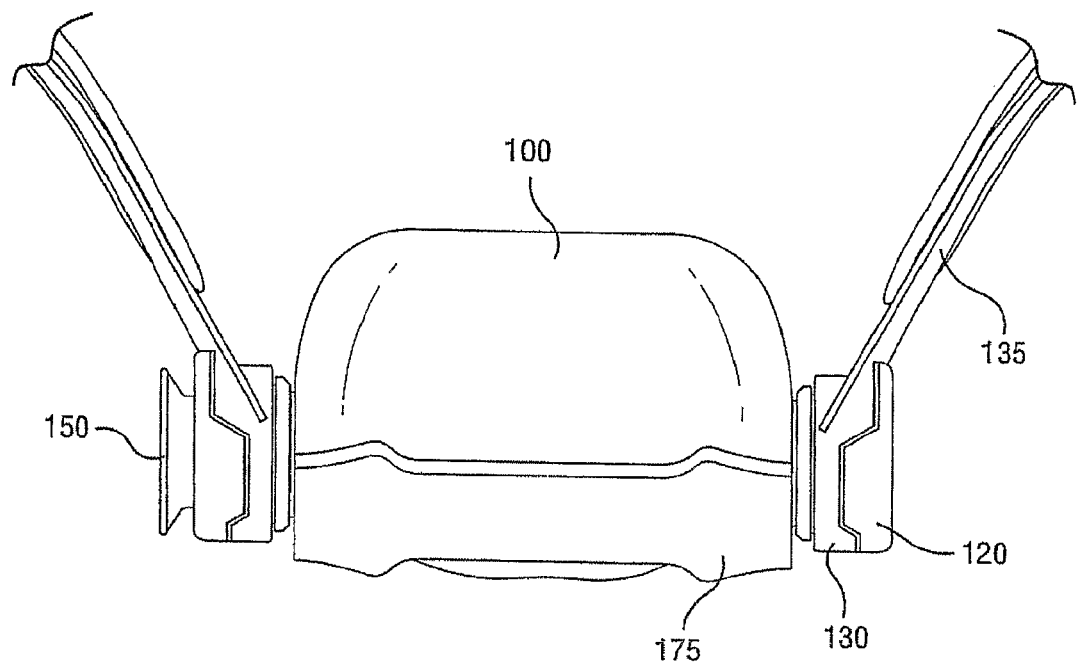
Figure 7:
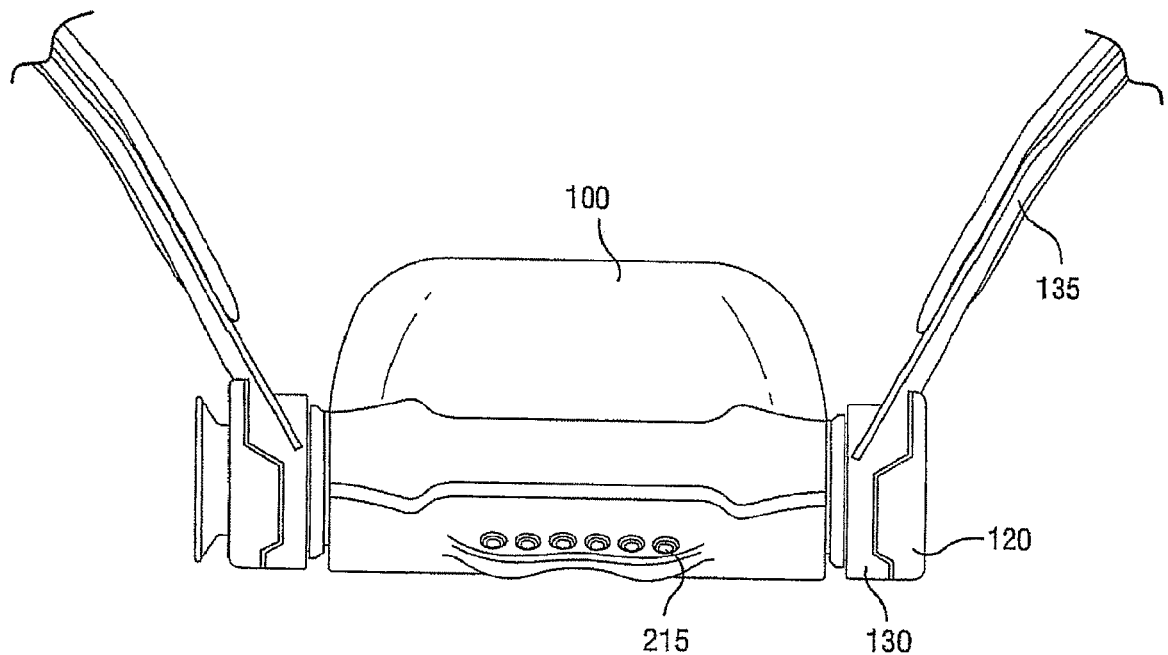

FIG. 3 is an exploded view of cushion component 100, frame 95 and a clip element 175, together defining a cushion sub-assembly 155. FIG. 4 shows the cushion sub-assembly 155 in the assembled condition, along with yoke 135, seal portion 120 and elbow 145. FIG. 5 is a cross sectional view of the assembly. FIGS. 6-10 are additional views of the cushion assembly as assembled with lateral headgear straps and associated yokes.

Figure 13:
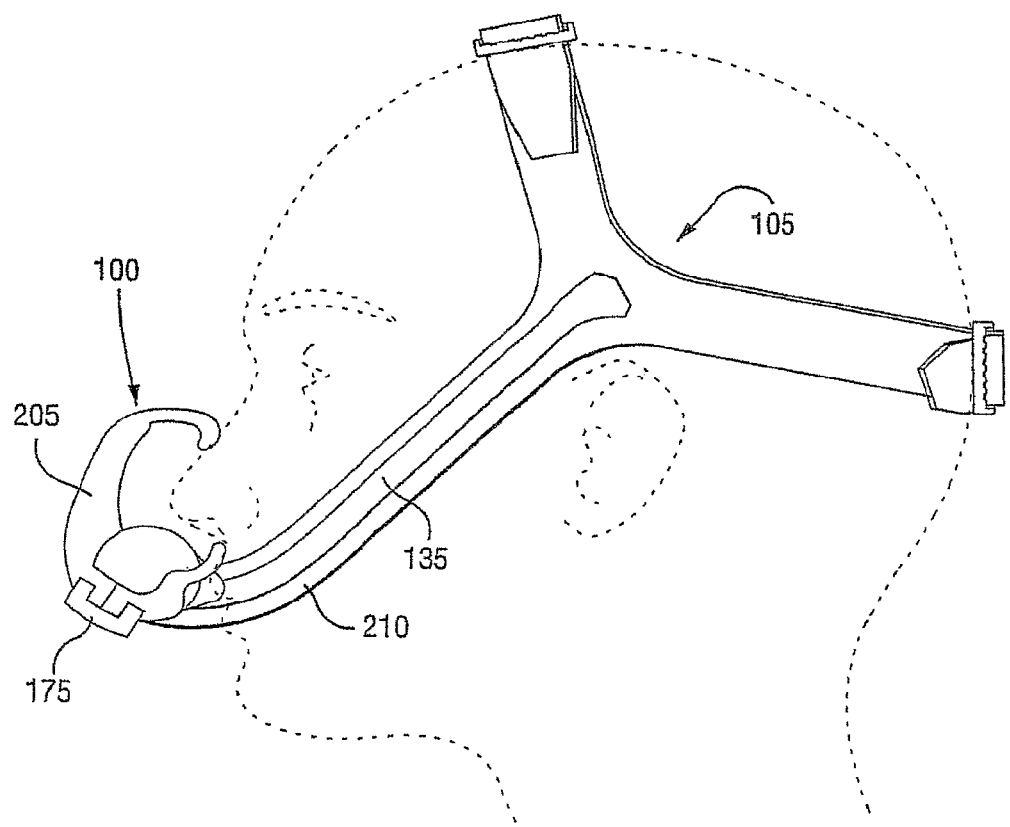

Cushion component 100 includes lateral sides 160 configured to engage with corresponding channels 165 formed in the frame 95. Cushion component 100 includes an aperture 196 (schematically illustrated) to receive the user's nose. End portions 170 of cushion component 100 are wrapped around frame 95, and clip element 175 is attached to the sub-assembly of the cushion component and the frame, by sliding the clip element over the combined cushion component and frame. FIGS. 4 and 13 are a cross-sectional view showing the sandwich-like connection between the lateral sides of the cushion 170, the frame 95 and the clip element 175.

Figure 11:
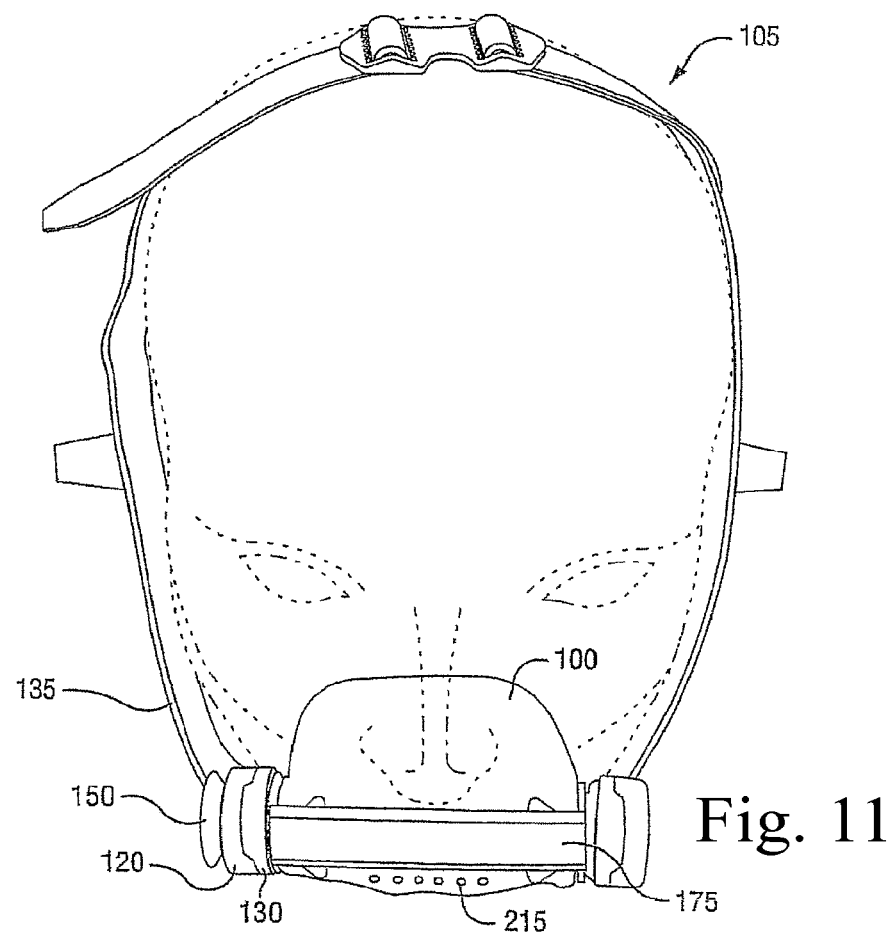
Figure 12:
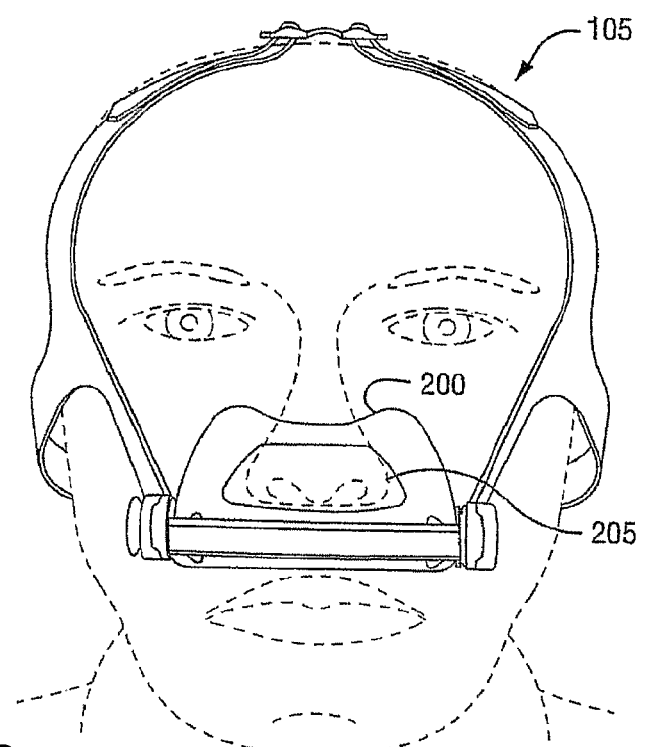

FIG. 11 is a top view of the mask assembly in use on a user's head, while FIG. 12 is a front view. As seen, common frame 95 is positioned just below and partially under the user's nose, and above the upper lip of the user. This positioning of the frame to cushion interface closer to the centroid of the mask assembly, which helps keep a low profile (non-obstructive) and reduces moments imposed on the mask assembly tending to pull the mask assembly away from the user's face.

In the embodiment described above, the cushion component 100 is bisected (see FIGS. 4 and 13) along the longitudinal axis of the frame to create later sides that wrap around the frame for insertion of the channel. In another embodiment, the cushion is not necessarily bisected. Instead, the apertures 162 in the lateral sides of the cushion are simply stretched over the connectors of the frame until a protruding portion of the cushion engages the respective channels of the frame.

Further, cushion component 100 has an upper portion 200 that is configured to contact the transition between the bony and cartilage portions of the user's nose. Generally, with regard to its footprint, the cushion component is similar to ResMed's VISTA™ cushion, as described in U.S. patent application Ser. No. 11/124,251, filed May 9, 2005, incorporated herein by reference.

Cushion component 100 has a thickened portion 205 that acts as a pseudo or "soft" frame to provide support for the rest of the membrane of the cushion. Effectively, the thickened portion 205 of the cushion enlarges the "frame" area of the common Swift™ frame. In this example, the thickened portion 205 has the shape of a semi-circle or trapezoid. See, e.g., FIGS. 2 and 12.

Common headgear assembly 105 is similar to the headgear assembly described in relation to ResMed's U.S. patent application Ser. No. 10/781,929. However, common headgear 105 has some differences. For example, as shown in FIG. 13, the vectors of the headgear straps 210 are changed.

Figure 8:
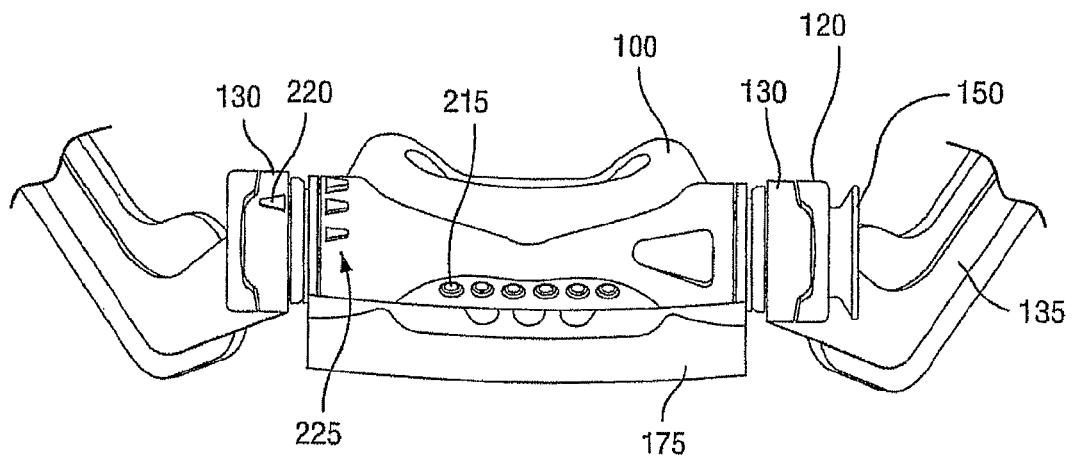
Figure 9:
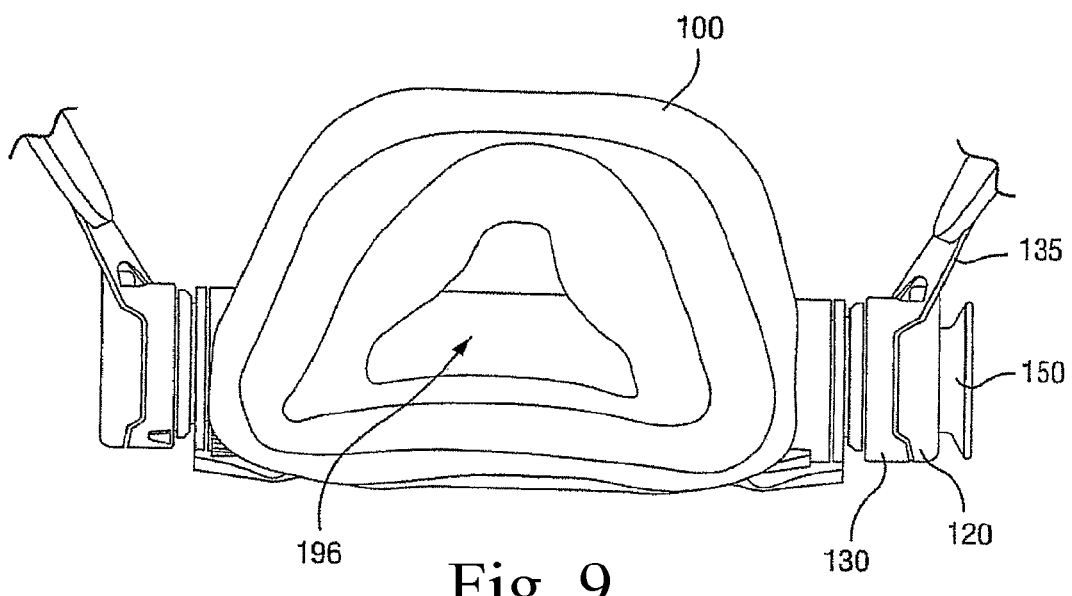
Figure 10:
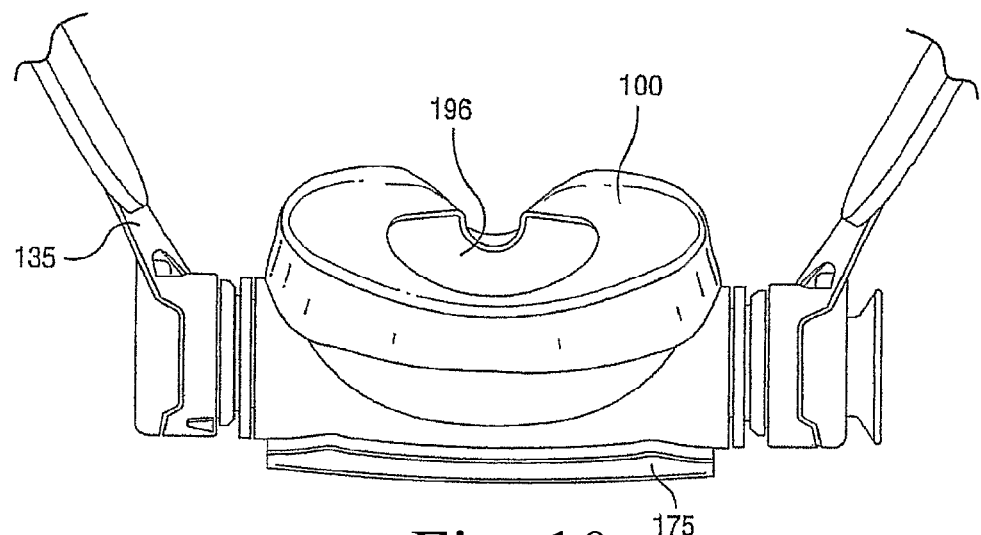

In FIGS. 6-13, the elbow 145 is omitted for clarity, although the plug 150 is illustrated. As shown in FIGS. 3, 7-8, and 11, the mask assembly includes a gas washout vent 215. The vent 215 could be on the frame and/or the cushion component. As shown in FIG. 8, the yoke 130 includes an alignment indicator 220 that aligns with one of a corresponding array of indicators 225 on the cushion/frame subassembly. The cushion/frame subassembly is rotatable relative to the headgear to ensure proper fit.

3.0 Third Embodiment—Common Swift™ Frame with Mirage™ Cushion Component

Figure 14:
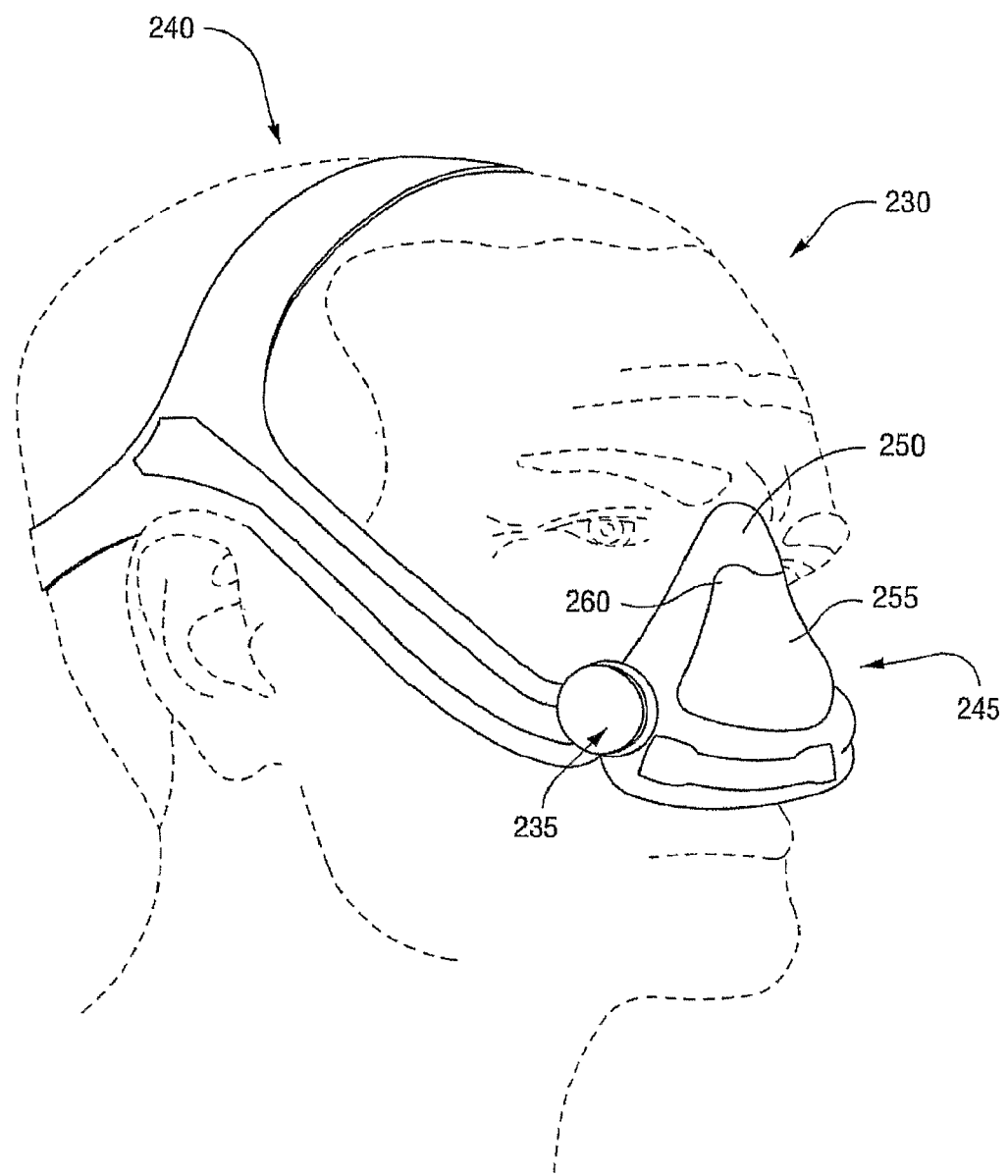
FIG. 14 is a perspective view of a mask assembly according to another embodiment of the present invention.

FIG. 14 illustrates a mask assembly 230 include a common frame 235, a headgear assembly 240 and a cushion component 245. This embodiment is similar to the prior embodiment, especially as the common frame is the same as described above in relation to FIGS. 2-13. The main difference is that the cushion component 245 takes the form of a nasal mask, e.g., ResMed's Mirage™ type cushion, as described in U.S. Pat. No. 6,112,746, incorporated herein by reference in its entirety. In this embodiment, the cushion component 245 is configured to form a breathing cavity that surrounds the nose of the user. The cushion component includes an upper apex portion 250 that makes contact with the bridge of the user's nose, between the eyes.

The cushion component 250 may include a thickened section 255 in order to help prevent flopping of the cushion away from the user's face. The thickened section 255 may include a cutout 260 in each corner to reduce force on the nasal bridge region.

Figure 15:
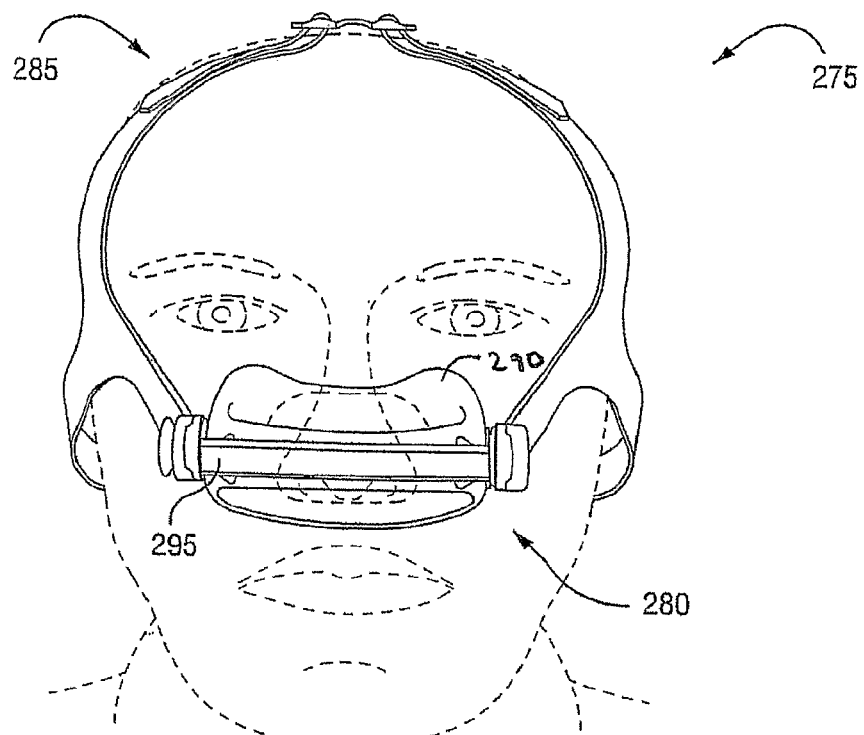
FIGS. 15-16 are views of a mask assembly according to yet another embodiment of the present invention.
Figure 16:
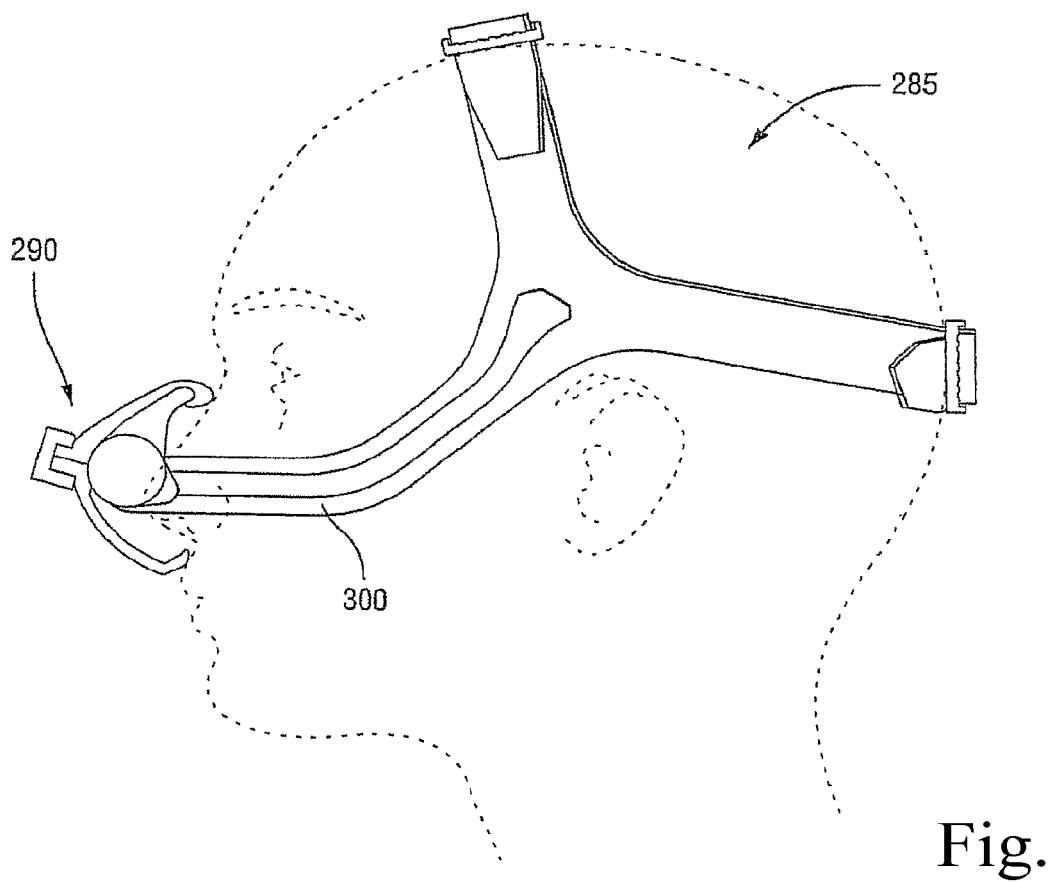

4.0 Fourth Embodiment—Common Swift™ Frame with Vista™ Cushion Component—Over the Nose FIGS. 15-16 show a mask assembly 275 according to another embodiment of the present invention. Mask assembly 275 includes a common frame 280, a headgear assembly 285, and a cushion component 290 like that described in relation to FIGS. 2-13 above. One difference in the present embodiment is the positioning of the common frame 280 relative to the user's face/nose. Specifically, the common frame 280 is positioned above the lower portion of the user's nose, such that the tip of the nose extends below the clip element 295. Further, as shown in FIG. 16, the vectors formed by the headgear straps 300 are slightly different than as shown in described in relation to FIG. 13. As a result of the positioning of the frame/cushion interface to more centrally locate the frame relative to the cushion, and/or because the vectors from the headgear straps act closer to the centroid of the mask on the face, this design may not necessarily include a thickened portion of the cushion.

5.0 Fifth Embodiment—Vista/Swift Prongs Combination

Figures 17, 18:
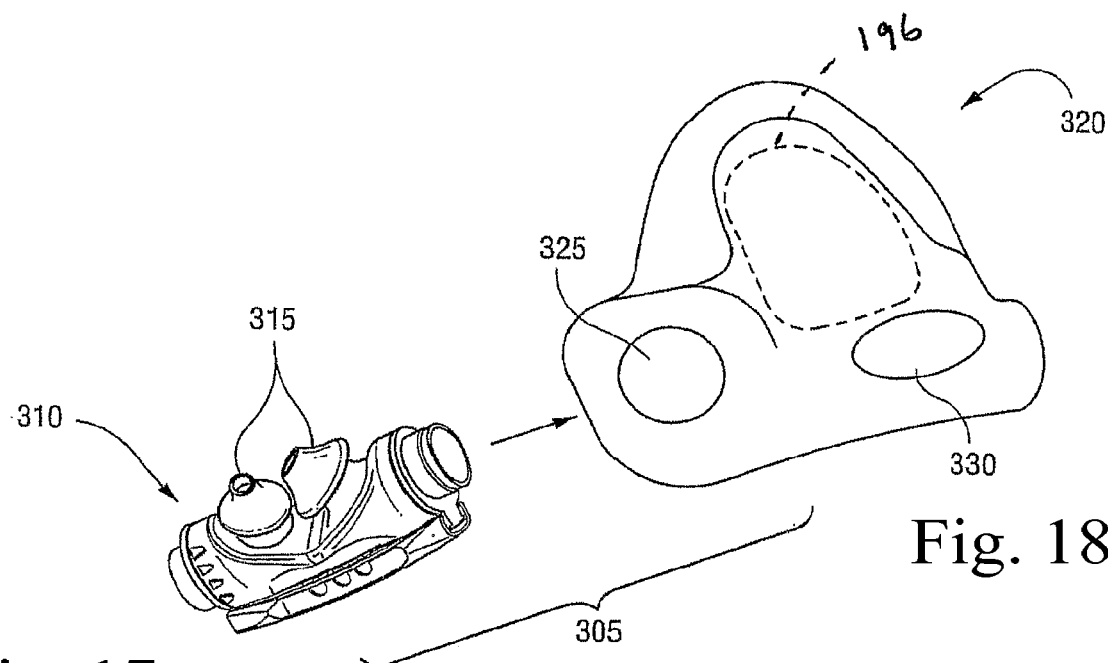
FIGS. 17-19 are views of a portion of a mask assembly according to still another embodiment of the present invention.
Figure 19:
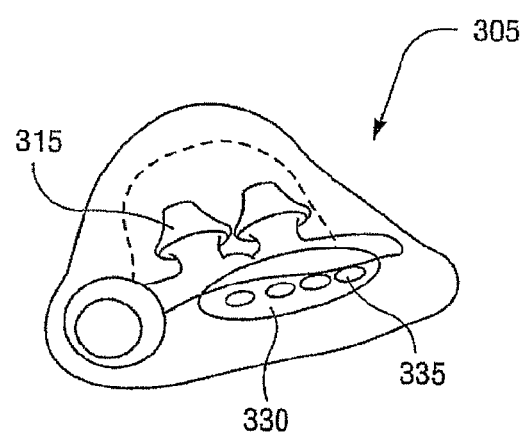

FIGS. 17-19 show a portion of another mask assembly 305 according to an embodiment of the present invention. FIG. 17 shows a common Swift™ frame and cushion assembly 310 in isolation, including prong elements 315 for engagement with the user's nares. FIG. 18 shows a supplemental Vista™ style cushion 320 adapted for use with the Swift™ cushion/frame assembly 310. The mask assembly is supported on the user's head using a headgear assembly as described above.

The supplemental cushion 320 includes at least one hole 325 provided on its lateral side for insertion over the frame/cushion assembly 310. Supplemental cushion 320 also includes a centrally located hole 330 that aligns with the gas washout vents 335 of the frame/cushion assembly 310. FIG. 19 shows the frame/cushion assembly 310 and the supplemental cushion 320 in assembled form. To assemble the supplemental cushion over the frame, each hole 325 of the supplemental cushion 320 is stretched over the connector of the frame, and the resiliency of the material of the supplemental cushion allows it to engage with the channels of the frame and/or to simply seal with an exposed surface of the frame cushion assembly. In this position, the prongs 315 seal with the nares, while the supplemental cushion includes a face contacting portion that seals with the user' face.

6.0 Additional Embodiments

As can be determined from the description above in relation to the embodiments of FIGS. 2-13 and the embodiment of FIGS. 15-16, one aspect of the invention is directed to the combination of a Swift™ frame with a Vista™ cushion component. As can be appreciated, the combination of these dissimilar mask systems required a number of adjustments, as can be derived from the above description and the drawings.

6.1 Locked Elbow

Furthermore, there are additional factors that may be considered when combining the various mask systems. For example, the force due to air pressure against the cushion may cause moments about the elbow. If these moments are not counteracted, the result may be the cushion rotating and losing seal. The elbow should be stiff enough to prevent rotation under pressure. A locking or ratcheting mechanism may be implemented to lock the rotation on the elbow when the desired angle is found. Locking may be achieved using an interference fit, and/or locking components, such as detents or a pin/groove arrangement. Generally, an approximation of the desired effect can be achieved by simply fixing the elbow in place relative to the frame. Otherwise, simply inhibiting rotation, e.g., by strapping the elbow to the adjacent headgear, can be effective as well.

6.2 Stiffening Member For Cushion Component

When the cushion is under pressure, moments about the cushion to frame interface are created. The force vector points which cause the moments may be shifted by introducing a non-flexible or stiffening member to the cushion. That is to say, in addition to having a moment about the elbow, there is also a moment about the interface of the stiff section of the cushion and the flexible part of the cushion.

6.2.1 Stiffening Ribs

Figure 20:
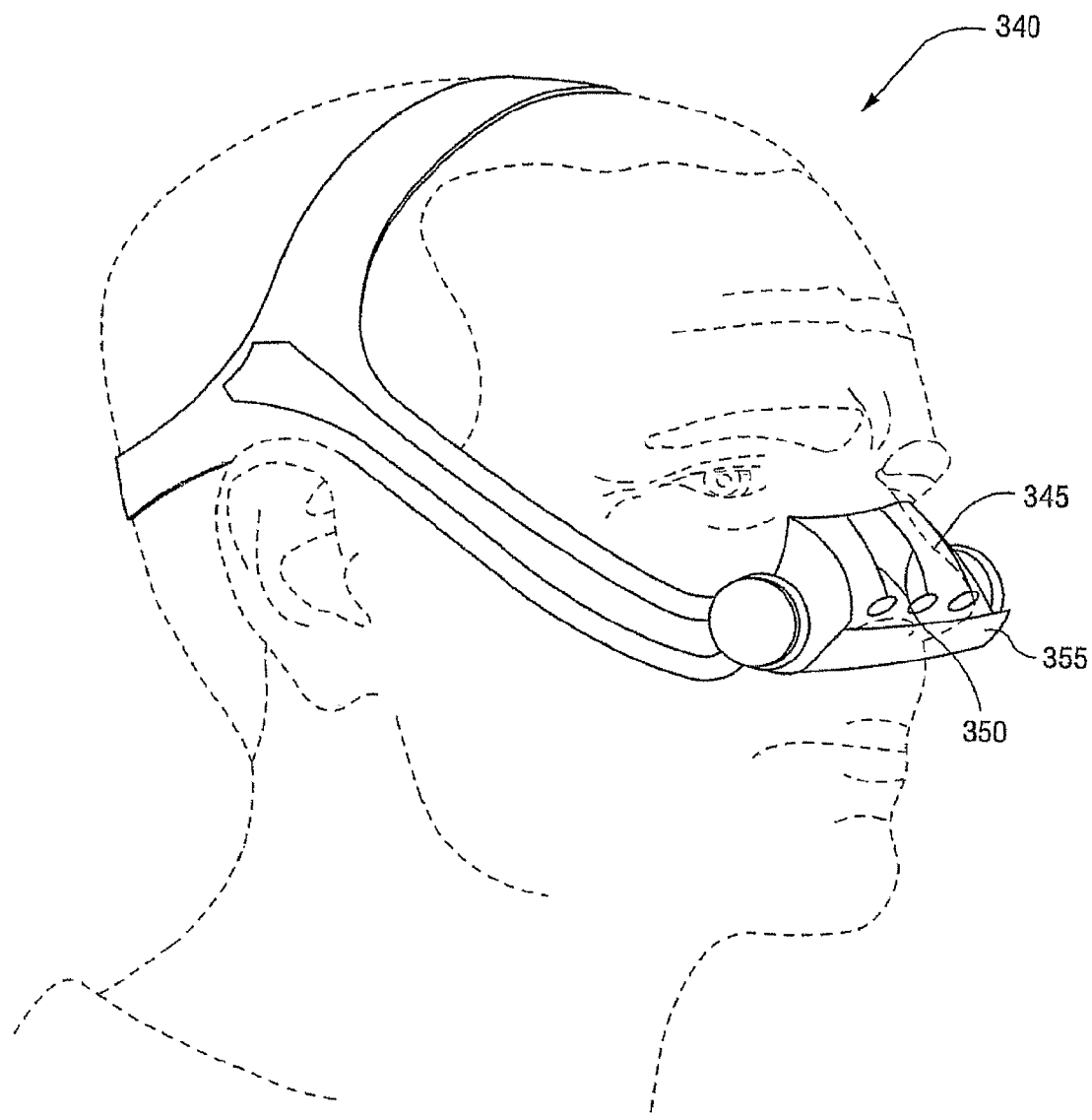
FIG. 20 is a perspective view of a mask assembly according to another embodiment of the present invention.

The mask assembly 340 in FIG. 20 includes a cushion component 345 that is similar in general shape to the Vista™ cushion in terms of its intended sealing footprint relative to the user's face, but it includes a plurality of ribs 350 that extend from the clip element 355 to the top of the cushion, to stop or help prevent the cushion from flexing about the elbow (or flopping off the face). The stiffening member (ribs in this example) will move this vector away from the elbow, and prevent the cushion from flopping off the face. The stiffening member should extend as close to the skin as possible without compromising comfort. The common frame is similar to that described above and may be, e.g., a Swift™ frame.

Figure 21:
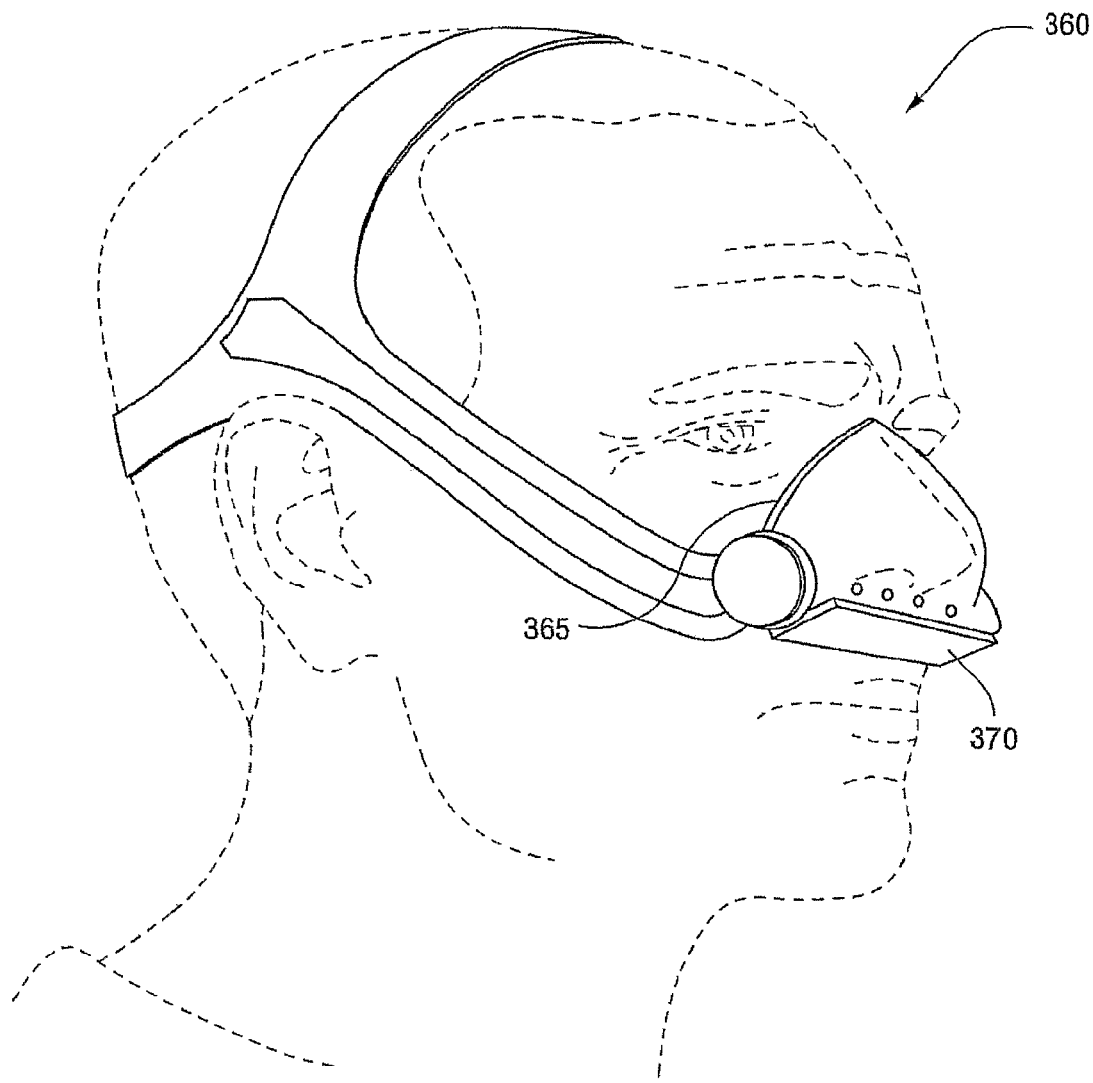
FIG. 21 is a perspective view of a mask assembly according to another embodiment of the present invention.

The mask assembly 360 in FIG. 21 includes a rib 365 along the perimeter of the cushion to help support and/or push the cushion onto the user's face. The rib 365 may be comolded with the cushion. The cushion forms a breathing cavity which receives the nose of the user, and the upper apex of the cushion extends across the bridge of the user, between the eyes. In this example, the cushion can be ResMed's Mirage™ cushion, adapted for assembly to common frame. Common frame is similar to that described above and may be, e.g., a Swift™ frame. However, the clip element 370 of the cushion assembly is slightly rotated such that it is positioned to face downwardly.

6.2.2 Thickened Cushion Portion

The stiffening member may take the form of one or more thickened elements, e.g., by thickening the cushion which will result in it being stiffer in sections. See, e.g., the relatively thickened portion of cushion component in FIG. 13. Ribs could be made in the cushions, extending from the frame to the highest point of the cushion. A pseudo frame could be implemented where a large portion of the cushion is thick silicone, only the areas in contact, or requiring flex (as in a "bubble" cushion or single walled membrane) will be thin.

6.3 Nose Tip Cushion Component

Figure 22:
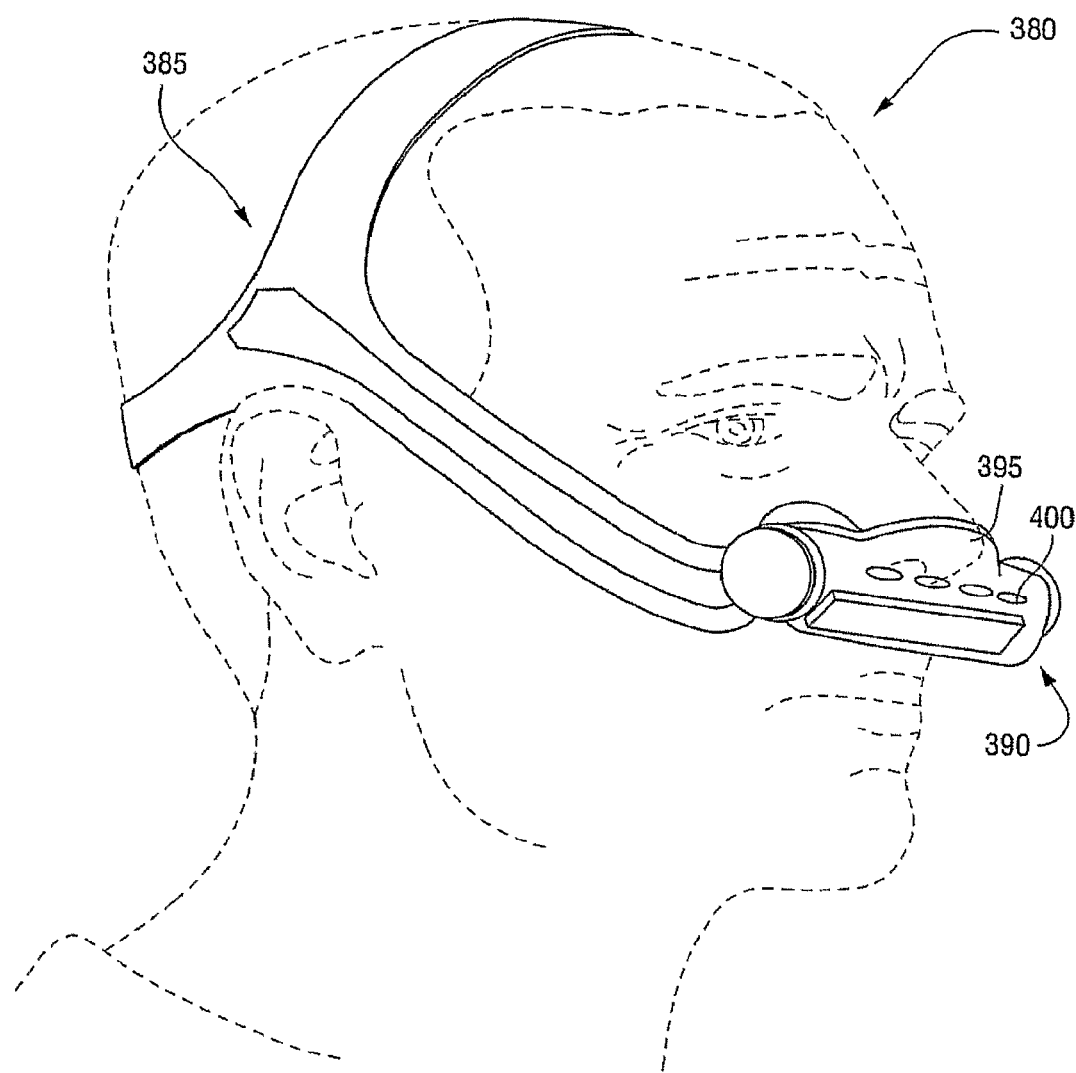
FIG. 22 is a perspective view of a mask assembly according to another embodiment of the present invention.

FIG. 22 shows a mask assembly 380 according to another embodiment of the invention having a headgear assembly 385 and a common Swift™ frame 390 as described above, as well as cushion component 395 in the form of a nose tip cushion. The cushion includes a membrane that extends up the side of the nose. The membrane could extend just over the tip of the nose. The cushion could incorporate a bubble style seal over the tip of the nose. The mask assembly includes one or more vent openings 400 provided in the frame/cushion component.

6.4 Full-Face Cushion

Figure 23:
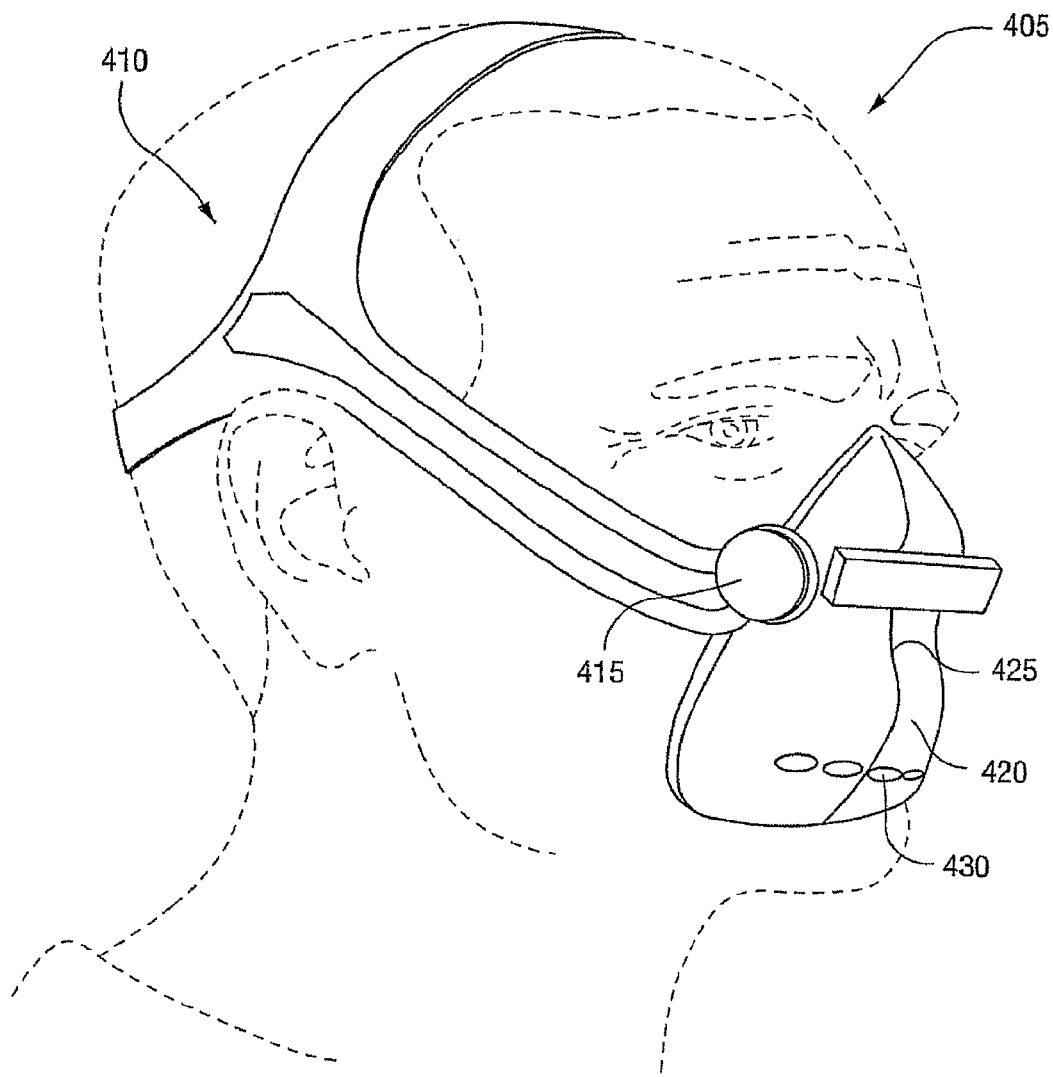
FIG. 23 is a perspective view of a mask assembly according to another embodiment of the present invention.

FIG. 23 shows a mask assembly 405 according to yet another embodiment of the present invention having a headgear assembly 410 and common Swift™ frame 415 as described above, as well as a cushion component 420 in the form of a full-face cushion, such as that available from ResMed under the name UltraMirage™ full-face cushion and described in U.S. Pat. No. 6,513,526, incorporated herein by reference in its entirety. The cushion component 420 would be adapted for use with a Swift™ type frame, as described above.

The cushion 420 may include a rib 425 that extends from the bottom to the top of the cushion. Furthermore, the frame 415 is positioned on the upper ½ to upper ⅓ of the cushion to support the cushion. The frame to cushion interface is positioned below the nose, although it may be above the nose. The cushion may include one or more gas washout vents 430.

7.0 Adjustable Positioning of the Cushion

7.1 Adjustable Nose Height

Figure 24:
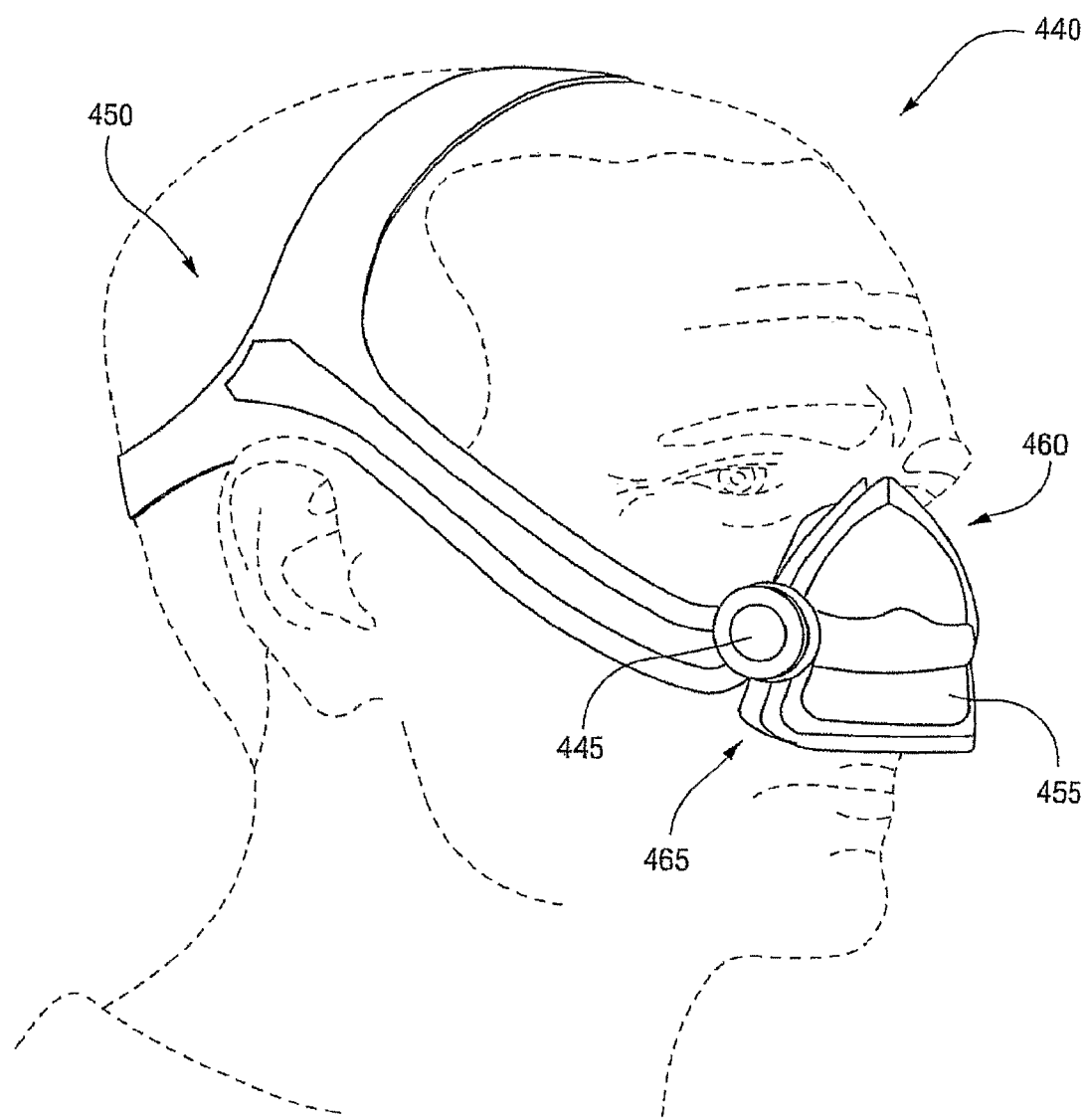
FIG. 24 is a perspective view of a mask assembly according to another embodiment of the present invention.

FIG. 24 shows a mask assembly 440 according to yet another embodiment of the present invention including a common Swift™ frame 445, a headgear assembly 450, and a Vista™-like cushion 455 supported by the frame.

The upper part 460 of the cushion may include a thin membrane (the lower cushion may be like a double wall Vista™ cushion). This has the advantage of reduced weight and subjectively feels light to wear. It may also allow deflection around contours of nose as it will be more flexible than a conventional thick cushion. This will help with fit and the range of patients suited to each size.

In an alternative, the upper part 460 of the cushion shown in FIG. 24 includes a bellows type arrangement around the cushion which may be inflated to help pressure and fit, like the ResMed Activa™ mask, described in U.S. Pat. No. 4,772,760 and U.S. application Ser. No. 10/655,622, filed Sep. 5, 2003, each incorporated herein by reference in its entirety. In the alternative, the cushion may include a stiff drinking straw-like structure, e.g., plastic corrugations that maintain shape in a variety of positions. The straw-like structure would click or fold into different positions to allow more or less nose height.

The lower part of the cushion 465 may include a gusset portion, a double gusset, or a solid silicon structure.

7.2 Adjustable Cushion Height

As described above, the position of the centroid of the cushion to frame interface (frame clip location) may be changed, depending on application. The closer the headgear vectors act to the centroid of the cushion the more stable the cushion will be on the face of the patient; this can reduce the rigidity required within the cushion to maintain support of the membrane. The frame location in FIGS. 2-13 is closer to the centroid as compared to the location of the centroid in FIGS. 15-16. In these embodiments, the positions of the cushions relative to the face remain generally constant.

However, it is also possible to change the position of the cushion relative to the face and frame, while maintaining the frame in a constant position. The mask assembly 500 in FIGS. 25-26 includes a common Swift™ frame 505 supported by Swift™-like headgear 510, in addition to a Vista™ like cushion 515 supported by the frame 505.

Figure 25:
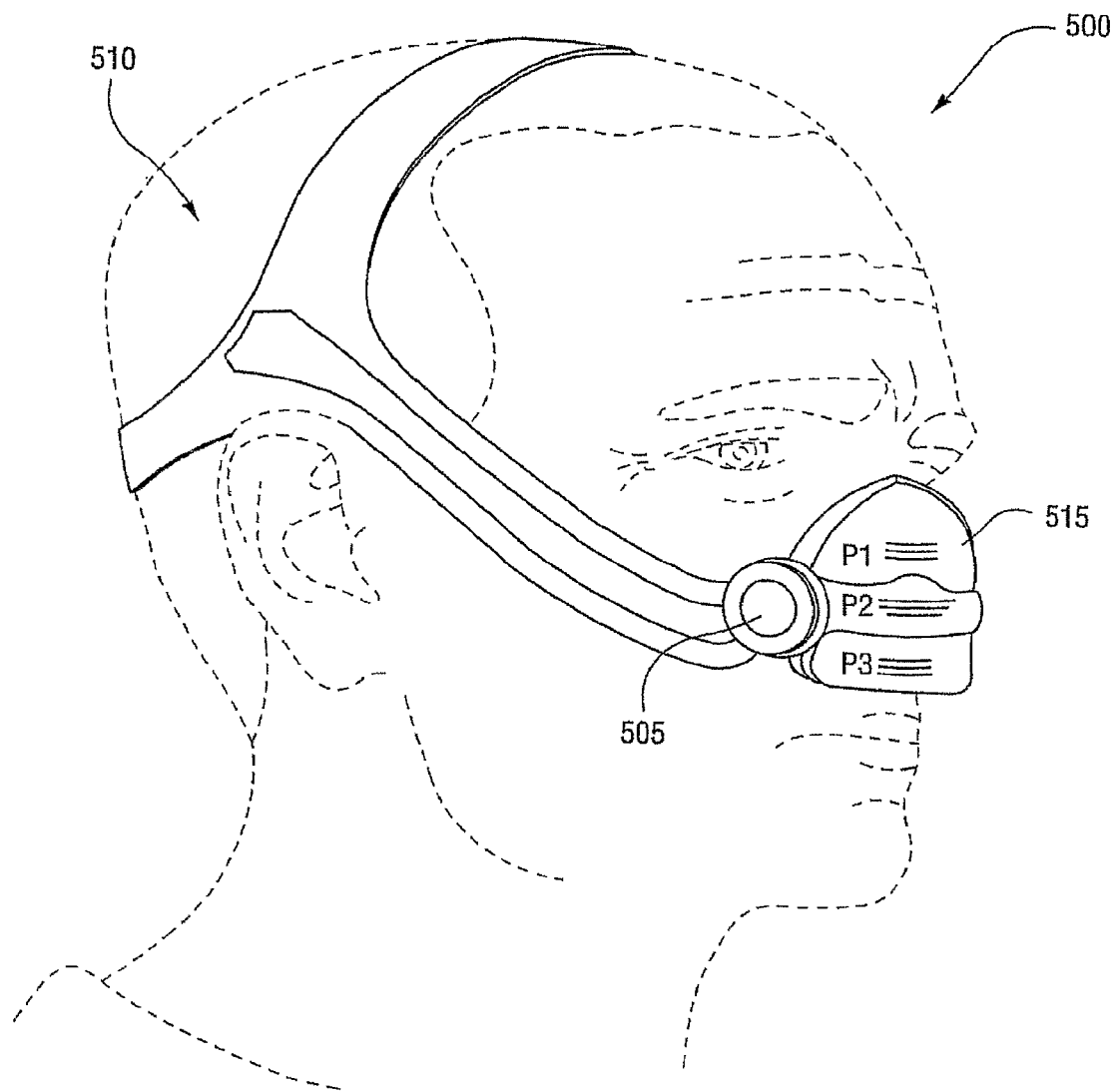
FIGS. 25-26 are views of a mask assembly according to another embodiment of the present invention.
Figure 26:
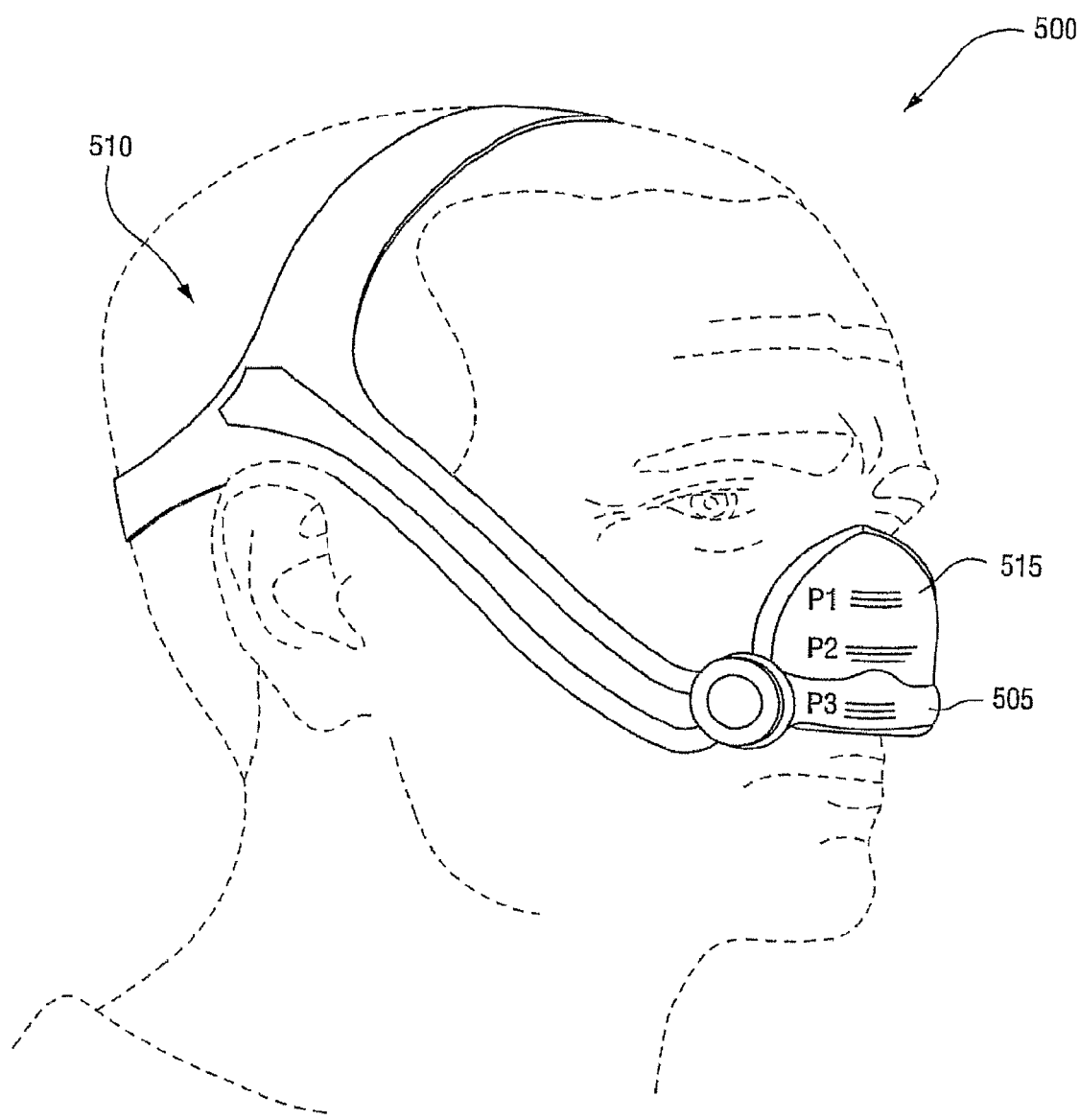

In FIGS. 25-26, the axis of location of the frame 505 is across the middle of the nose, although it could be higher or lower. As schematically shown, the axis of location of the frame onto the cushion may vary according to user preference (which will be influenced by head shape/headgear angles). In FIGS. 25-26, it can be seen that the headgear-frame angle remains constant and the frame is located at higher or lower cushion positions, position 2 in FIG. 25 and position 3 in FIG. 26. Adjustment can be effected using mechanical expedients such as a sliding arrangement. Holes in the sides of the cushion may allow stretching in to accommodate positioning of the cushion in the various positions.

Alternatively, the headgear and frame angle may rotate around the same cushion position. As a further alternative the headgear location point could be on a lobe or cam to move it relative to the cushion. A further embodiment is the use of weight to change the center of gravity of the cushion or frame/headgear system.

8.0 Chin Strap

FIGS. 27-31 illustrate a mask assembly 600 according to a further embodiment of the present invention. Mask assembly includes a frame 605 (e.g. polycarbonate shell), a headgear assembly 610, a cushion component 615, and a chin strap assembly 620 supported by the frame.

Figure 30:
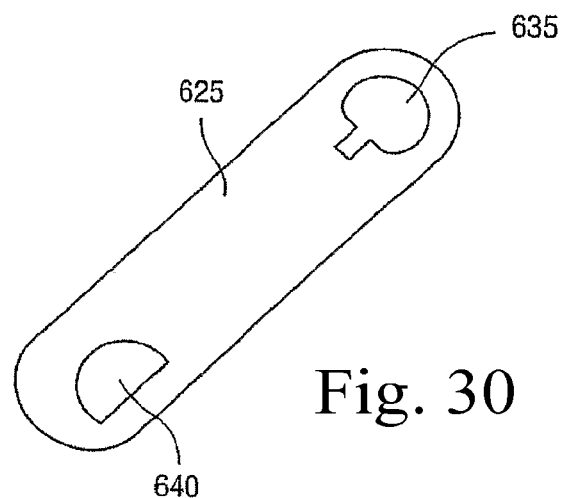

Chin strap assembly 620 includes an extender 625 and chin strap 630. Extender 625 is shown in FIG. 30 and is preferably made of a rigid material, e.g., polycarbonate or a rigid plastic backed with headgear foam material. Extender 625 includes an aperture 635 by which a bevel clip 640 (FIG. 29) may be used to selectively attach the extender 625 to the frame, e.g., using interference snap fit. Extender 625 includes a hole 640 for receiving a strap 645 of the chin strap. Each strap includes hook and loop fastening elements, e.g., Velcro®.

Figure 27:
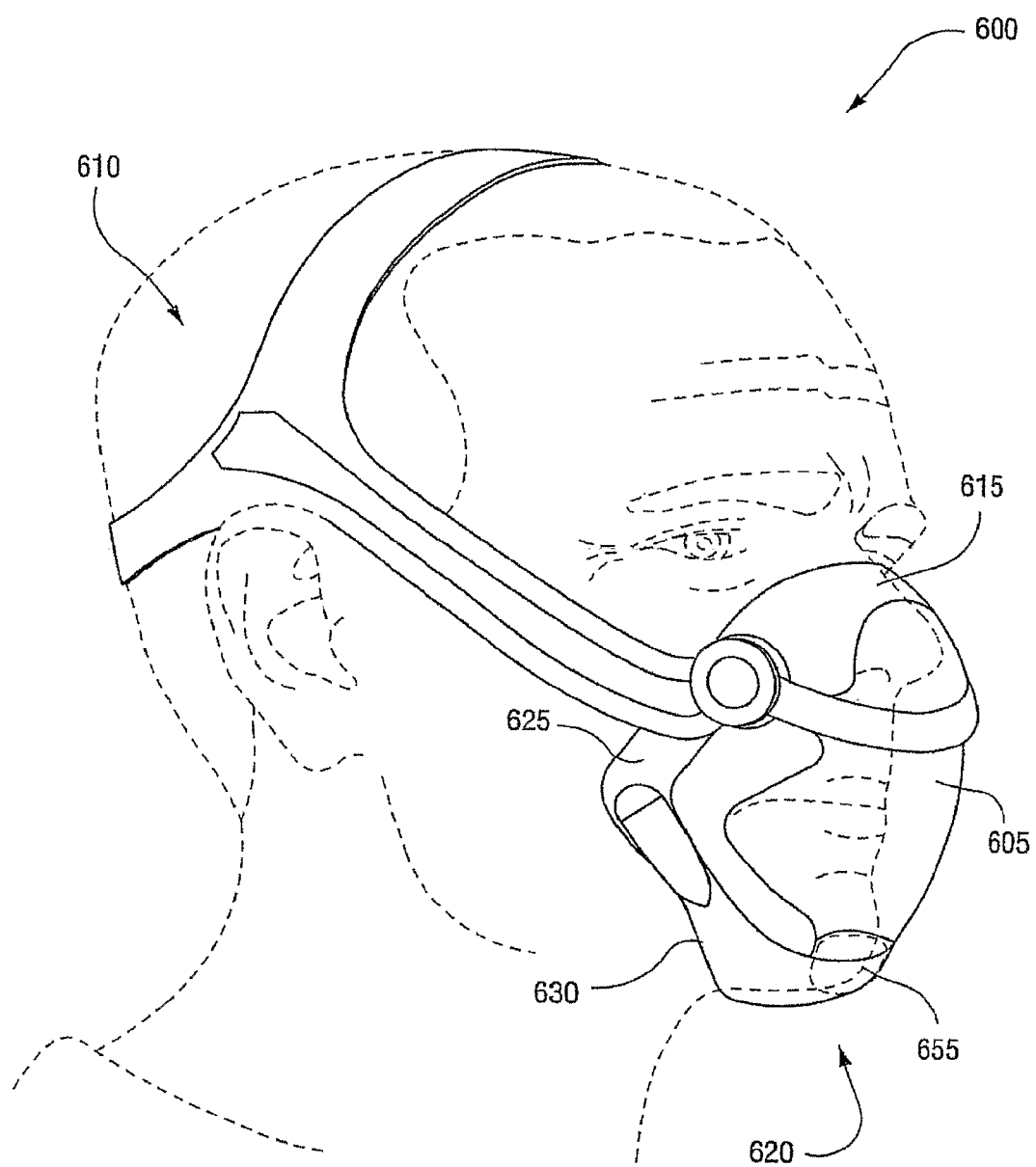
FIGS. 27-31 are views of a mask assembly according to still another embodiment of the present invention.
Figure 28:
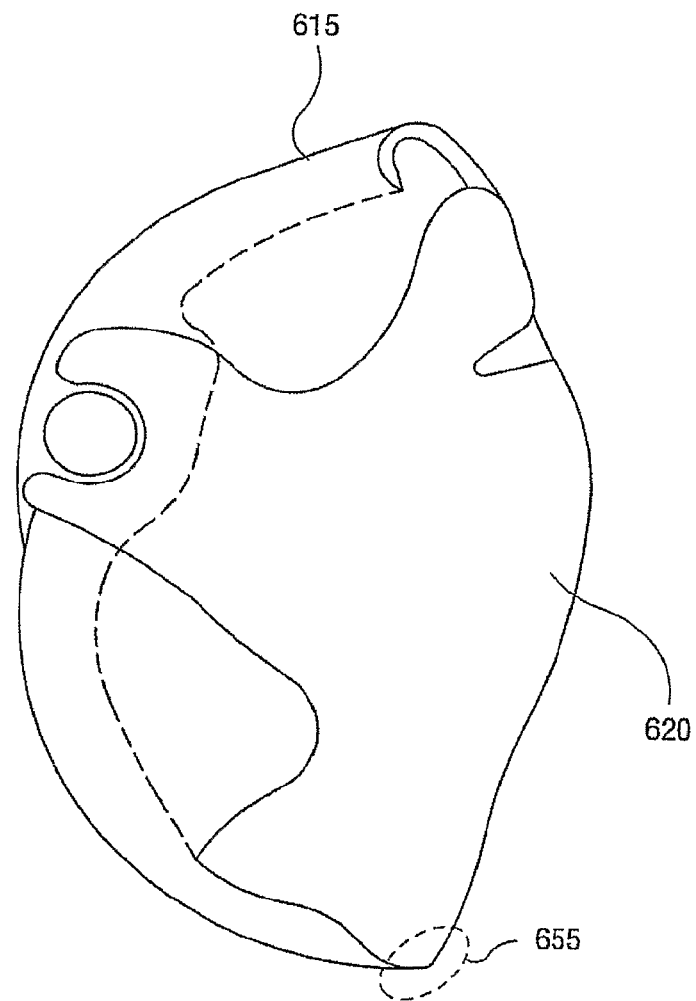
Figure 29:
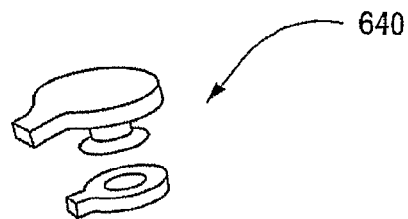
Figure 31:
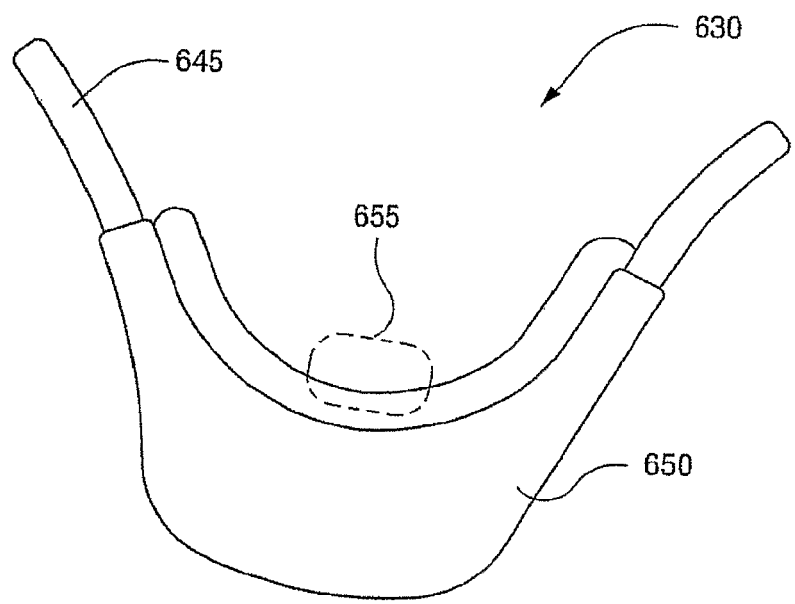

Chin strap 630 includes a cushion sealing area 650, and is made from a foamed headgear material. The chin strap is preferably elastic. The chin strap is bonded to the frame at a bond point or region 655, e.g., as shown in FIGS. 27, 28 and 31. Bonding may be achieved, e.g., via adhesive, plasma or lamination methods.

Another variant is to simply use only the extender and chin strap shown in FIGS. 30 and 31, respectively, along with another mask of choice, e.g., ResMed's Nightingale mask, more fully described in PCT Patent application no. PCT/AU04/01832, filed Dec. 24, 2004, incorporated by reference in its entirety. A further embodiment is the use of the Nightingale headgear with the chin strap assembly and the frame cushion.

A further embodiment is the combination the full-face seal as shown in FIG. 27, along with nasal prongs as shown in FIG. 19.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A respiratory mask assembly for providing respiratory therapy to a patient, the respiratory mask assembly comprising:
   a main body;
   a cushion component including a sealing portion, wherein the sealing portion is constructed and arranged to form a seal with a patient's nose;
   a cushion retainer configured to releasably couple the cushion component to the main body,
   wherein the cushion retainer comprises a separate and distinct peripheral component from the main body,
   wherein the cushion retainer is relatively harder than the cushion component,
   wherein the cushion retainer is attachable to the cushion component to form a unit that as a whole is subsequently releasably coupled to the main body,
   wherein the cushion retainer includes a cushion retainer part structured and arranged to engage behind a retainer part provided to the main body to releasably couple the cushion retainer to the main body, wherein the cushion retainer is releasably coupled to the main body in a substantially fixed, substantially non-adjustable position to resist adjustable movement between the cushion retainer and the main body when the cushion retainer is coupled to the main body, wherein the cushion component and the cushion retainer form at least a portion of a breathing chamber pressurizable to a therapeutic pressure,
   wherein the cushion retainer includes an opening structured to receive a flow of air at the therapeutic pressure for breathing by the patient, and
   wherein the cushion retainer is configured to releasably couple the cushion component to the main body while allowing the flow of air to the cushion component;
   a gas washout vent component configured to releasably couple with the main body, the gas washout vent component configured to washout gas from the breathing chamber to ambient atmosphere, wherein the main body includes a lower opening having a closed shape and an upper opening having a closed shape that is spaced apart and superior to the lower opening, wherein the upper opening is configured to receive the cushion retainer when the cushion retainer is releasably coupled with the main body, wherein the gas washout vent component is releasably coupled to the main body at the lower opening, and the lower opening is configured to allow the gas washout vent component to communicate with the breathing chamber when the gas washout vent component is releasably coupled to the main body, wherein the gas washout vent component comprises a separate and distinct peripheral component from the main body, the cushion component, and the cushion retainer, wherein the gas washout vent component is configured to engage the main body along an entire perimeter of the lower opening, and wherein, when the gas washout vent component is released from the main body, the gas washout vent component is thereby separated from the cushion component and the cushion retainer;

headgear to maintain the respiratory mask assembly in position on a patient's head, the headgear including upper side straps and lower side straps; and a pair of lower headgear connectors, each of the pair of lower headgear connectors configured to connect a respective one of the lower side straps to the main body.

2. The respiratory mask assembly according to claim 1, further comprising a pair of upper lateral members provided to the main body, each of the pair of upper lateral members including a respective one of a pair of upper headgear connectors, and the upper side straps are adapted to connect to a respective of the pair of upper headgear connectors.

3. The respiratory mask assembly according to claim 1, wherein the cushion retainer includes an inside surface exposed to said therapeutic pressure in use.

4. The respiratory mask assembly according to claim 1, wherein the cushion retainer comprises polycarbonate and the cushion component comprises silicone.

5. The respiratory mask assembly according to claim 1, wherein the cushion retainer part forms a space to receive the retainer part of the main body when the cushion retainer is releasably coupled with the main body.

6. A CPAP system for providing respiratory therapy to a patient, the CPAP system comprising:
   the respiratory mask assembly according to claim 1;
   a blower to supply a flow of air at a therapeutic pressure; and
   a conduit to pass the flow of air at the therapeutic pressure from the blower to the respiratory mask assembly.

7. The respiratory mask assembly according to claim 1, wherein the gas washout vent component includes an axis that is configured to align with an axis of the lower opening when the gas washout vent component is releasably coupled to the main body.

8. The respiratory mask assembly according to claim 1, wherein the cushion component is configured to remain coupled to the main body when the gas washout vent component is released from the main body.

9. The respiratory mask assembly according to claim 1, wherein at least a portion of the cushion component is arranged superior to the upper opening of the main body.

* * * * *